United States Patent
Kitano et al.

(10) Patent No.: US 12,281,083 B2
(45) Date of Patent: *Apr. 22, 2025

(54) 2-SUBSTITUTED AMINO-NAPHTH (1,2-D) IMIDAZOL-5-ONE COMPOUNDS OF PHARMACEUTICALLY ACCEPTABLE SALTS THEREOF

(71) Applicant: PTC Therapeutics, Inc., Warren, NJ (US)

(72) Inventors: Hiroyuki Kitano, Osaka (JP); Kazuto Mori, Osaka (JP)

(73) Assignee: PTC Therapeutics, Inc., Warren, NJ (US)

( * ) Notice: Subject to any disclaimer, the term of this patent is extended or adjusted under 35 U.S.C. 154(b) by 315 days.

This patent is subject to a terminal disclaimer.

(21) Appl. No.: 17/862,290

(22) Filed: Jul. 11, 2022

(65) Prior Publication Data
US 2023/0116786 A1    Apr. 13, 2023

Related U.S. Application Data

(63) Continuation of application No. 16/989,582, filed on Aug. 10, 2020, now Pat. No. 11,390,588, which is a
(Continued)

(30) Foreign Application Priority Data

Nov. 15, 2016  (JP) ................. 2016-222028
Dec. 26, 2016  (JP) ................. 2016-250981

(51) Int. Cl.
| | | |
|---|---|---|
| A61K 31/4184 | (2006.01) | |
| A61K 31/422 | (2006.01) | |
| A61K 31/427 | (2006.01) | |
| A61K 31/4439 | (2006.01) | |
| A61K 31/4709 | (2006.01) | |
| A61K 31/538 | (2006.01) | |
| A61P 3/10 | (2006.01) | |
| A61P 25/00 | (2006.01) | |

(Continued)

(52) U.S. Cl.
CPC ........ C07D 233/88 (2013.01); A61K 31/4184 (2013.01); A61K 31/422 (2013.01); A61K 31/427 (2013.01); A61K 31/4439 (2013.01); A61K 31/4709 (2013.01); A61K 31/538 (2013.01); A61P 3/10 (2018.01); A61P 25/00 (2018.01); A61P 25/16 (2018.01); C07D 235/02 (2013.01); C07D 401/04 (2013.01); C07D 401/14 (2013.01); C07D 403/04 (2013.01); C07D 403/10 (2013.01); C07D 403/14 (2013.01); C07D 405/04 (2013.01); C07D 407/04 (2013.01); C07D 413/04 (2013.01); C07D 413/10 (2013.01); C07D 413/14 (2013.01); C07D 417/04 (2013.01)

(58) Field of Classification Search
CPC ............ A61K 31/4184; A61K 31/4439; A61K 31/4709; A61K 31/422; A61K 31/538; A61K 31/427; A61P 25/00; A61P 25/16; A61P 3/10
See application file for complete search history.

(56) References Cited

U.S. PATENT DOCUMENTS

| | | | |
|---|---|---|---|
| 5,801,159 | A | 9/1998 | Miller et al. |
| 6,232,060 | B1 | 5/2001 | Miller et al. |

(Continued)

FOREIGN PATENT DOCUMENTS

| | | |
|---|---|---|
| EP | 0 240 047 A1 | 10/1987 |
| EP | 3091003 A1 | 11/2016 |

(Continued)

OTHER PUBLICATIONS

Golub et al., Science, vol. 286, Oct. 15, 1999, pp. 531-537. (Year: 1999).*

(Continued)

*Primary Examiner* — Laura L Stockton
(74) *Attorney, Agent, or Firm* — Squire Patton Boggs (US) LLP

(57) ABSTRACT

Provided herein are therapeutic and/or prophylactic compounds for mitochondrial or oxidative stress diseases such as cancer, amyotropic lateral sclerosis, Creutzfeldt-Jakob disease, Machado-Joseph disease, spinocerebellar ataxia, Huntington disease, Parkinson disease, Alzheimer disease, myocardial infarction, cerebral infarction, diseases related to aging, diabetes, alcoholic liver injury, chronic obstructive pulmonary disease, mitochondrial myopathy, encephalopathy, lactic acidosis, and stroke-like episodes (MELAS), and the like, wherein the compound is represented by formula (1), or reduced forms thereof, or pharmaceutically acceptable salts thereof.

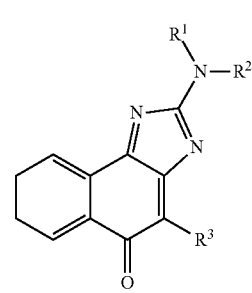

18 Claims, No Drawings

Related U.S. Application Data continuation of application No. 16/349,940, filed as application No. PCT/US2017/061879 on Nov. 15, 2017, now Pat. No. 10,738,014.

(51) Int. Cl.

| | | |
|---|---|---|
| *A61P 25/16* | (2006.01) | |
| *C07D 233/88* | (2006.01) | |
| *C07D 235/02* | (2006.01) | |
| *C07D 401/04* | (2006.01) | |
| *C07D 401/14* | (2006.01) | |
| *C07D 403/04* | (2006.01) | |
| *C07D 403/10* | (2006.01) | |
| *C07D 403/14* | (2006.01) | |
| *C07D 405/04* | (2006.01) | |
| *C07D 407/04* | (2006.01) | |
| *C07D 413/04* | (2006.01) | |
| *C07D 413/10* | (2006.01) | |
| *C07D 413/14* | (2006.01) | |
| *C07D 417/04* | (2006.01) | |

(56) References Cited

U.S. PATENT DOCUMENTS

| | | |
|---|---|---|
| 6,608,196 B2 | 8/2003 | Wang et al. |
| 6,653,346 B1 | 11/2003 | Wang et al. |
| 10,738,014 B2 | 8/2020 | Kitano et al. |
| 11,390,588 B2* | 7/2022 | Kitano ............ C07D 235/02 |
| 2002/0143049 A1 | 10/2002 | Miller et al. |
| 2003/0176361 A1 | 9/2003 | Wand et al. |
| 2004/0105817 A1 | 6/2004 | Gilat et al. |
| 2005/0065099 A1 | 3/2005 | Walkinshaw et al. |
| 2006/0051844 A1 | 3/2006 | Heavner et al. |
| 2006/0281809 A1 | 12/2006 | Miller et al. |
| 2007/0072943 A1 | 3/2007 | Miller et al. |
| 2007/0225261 A1 | 9/2007 | Miller et al. |
| 2009/0291092 A1 | 11/2009 | Miller et al. |
| 2010/0010100 A1 | 1/2010 | Hinman et al. |
| 2010/0029706 A1 | 2/2010 | Miller et al. |
| 2010/0029784 A1 | 2/2010 | Hinman et al. |
| 2010/0056429 A1 | 3/2010 | Miller et al. |
| 2010/0063161 A1 | 3/2010 | Miller et al. |
| 2010/0105930 A1 | 4/2010 | Wesson et al. |
| 2010/0266591 A1 | 10/2010 | Bugelski et al. |
| 2010/0273892 A1 | 10/2010 | Miller et al. |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0101169 A1 | 4/2012 | Hawi |
| 2012/0122934 A1 | 5/2012 | Jankowski et al. |
| 2012/0122969 A1 | 5/2012 | Miller et al. |
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0345312 A1 | 12/2013 | Jankowski et al. |
| 2014/0243424 A1 | 8/2014 | Mollard et al. |
| 2014/0249332 A1 | 9/2014 | Mollard |
| 2014/0256830 A1 | 9/2014 | Hinman et al. |
| 2014/0275045 A1 | 9/2014 | Hinman et al. |
| 2014/0275054 A1 | 9/2014 | Hinman et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2016/0024085 A1 | 1/2016 | Hinman et al. |
| 2016/0115141 A1 | 4/2016 | Hinman et al. |
| 2018/0000749 A1 | 1/2018 | Mollard et al. |
| 2018/0002247 A1 | 1/2018 | Mollard et al. |
| 2018/0333389 A1 | 11/2018 | Miller |
| 2018/0362492 A1 | 12/2018 | Giannousis et al. |
| 2018/0370892 A1 | 12/2018 | Hinman et al. |
| 2019/0029975 A1 | 1/2019 | Shrader |
| 2019/0241497 A1 | 8/2019 | Hinman |
| 2019/0330159 A1 | 10/2019 | Kitano et al. |

FOREIGN PATENT DOCUMENTS

| | | |
|---|---|---|
| JP | 01-193253 A | 8/1989 |
| WO | WO 2011/113018 | 9/2011 |
| WO | WO 2012/154613 | 11/2012 |
| WO | WO 2013/006736 | 1/2013 |
| WO | WO 2012/170773 | 12/2013 |
| WO | WO 2016/114860 | 7/2016 |
| WO | WO 2017/123823 | 7/2017 |
| WO | WO 2018/129411 | 7/2018 |

OTHER PUBLICATIONS

International Search Report and the Written Opinion of International Application No. PCT/US2017/061879 mailing date of Feb. 22, 2018; 10 pages.

Heesing et al., "Synthese und polarographisches Verhalten von offenkettigen sowie heterocyclischen chinoiden Guanidin- und Harnstoff-derivaten", 1976, vol. 12, pp. 2222-2239.

* cited by examiner

2-SUBSTITUTED AMINO-NAPHTH (1,2-D) IMIDAZOL-5-ONE COMPOUNDS OF PHARMACEUTICALLY ACCEPTABLE SALTS THEREOF

CROSS REFERENCE TO RELATED APPLICATIONS

This application is a continuation of U.S. patent application Ser. No. 16/989,582 (filed Aug. 10, 2020), which is a continuation of U.S. patent application Ser. No. 16/349,940 (filed May 14, 2019; now U.S. Pat. No. 10,738,014), which is a national-phase application under 35 U.S.C. § 371 of International Patent Application No. PCT/US2017/061879 (filed Nov. 15, 2017), which claims the priority benefit of Japanese Application No. 2016-222028 (filed Nov. 15, 2016); and Japanese Application No. 2016-250981 (filed Dec. 26, 2016). The entire contents of these applications are hereby incorporated by reference herein.

This disclosure relates to 2-substituted amino-naphth[1,2-d]imidazol-5-one compounds and pharmaceutically acceptable salts thereof useful as medicaments, or more particularly, as pharmaceutical compositions comprising a 2-substituted amino-naphth[1,2-d]imidazol-5-one compound or a pharmaceutically acceptable salt thereof. Alternatively, this disclosure is related to a therapeutic agent comprising a 2-substituted amino-naphth[1,2-d]imidazol-5-one compound or a pharmaceutically acceptable salt thereof.

BACKGROUND

Oxidative stress occurs when active oxygen generated by an external or internal factor overwhelms the processing capacity of a living body. Active oxygen species (e.g., hydrogen peroxide, superoxide radical, and the like) are produced as a main product or by-product of various enzymatic reactions in cells. Although the living body is exposed to many oxidative stresses even under normal conditions, various antioxidation systems are fully used to maintain the homeostasis of the redox condition. When an excess of active oxygen, peroxides, and the like, or the collapse of an antioxidation system causes imbalance in the redox condition, the proteins, lipids, and DNAs become disordered and thereby various intra cellular organs become disordered. Accordingly, oxidative stress is believed to be involved in many diseases, such as cancer, lifestyle-related disease, central nervous system disease, lung disease, heart disease, kidney disease, ischemic disease, diseases related to aging, and the like. Specific examples thereof include, without limitation, amyotrophic lateral sclerosis (ALS), Huntington disease, Parkinson disease, Alzheimer disease, Friedreich ataxia (FRDA), Creutzfeldt-Jakob disease, Machado-Joseph disease, spinocerebellar ataxia, multiple system atrophy (MS), atherosclerosis, myocardial infarction, cerebral infarction, senile cognition disorder, diabetes, alcoholic liver injury, non-alcoholic steatohepatitis (NASH), chronic obstructive pulmonary disease (COPD), pulmonary fibrosis, hearing loss, and spinal muscular atrophy (SMA).

Meanwhile, mitochondria are one of the cell organelles in eukaryotic cells, and their main function is to supply ATP (adenosine triphosphate), which is energy necessary for cells to live. Moreover, since mitochondria are physiologically active oxygen sources under normal conditions, when an abnormality occurs in a function of the mitochondria, it is believed that a supply balance of active oxygen is disrupted to generate or increase oxidative stress. As described above, there is believed to be a close relationship between the mitochondria and oxidative stress.

For the above reasons, there is a possibility that various diseases including diseases related to mitochondrial dysfunction, such as mitochondrial disease, neurodegenerative disease, diseases related to aging, and the like, in addition to the above-described diseases, can be treated by suppressing oxidative stress (i.e., returning the balance of active oxygen/antioxidation system to normal). In some embodiments, diseases related to mitochondrial dysfunction include diseases such as amyotrophic lateral sclerosis (ALS), Huntington disease, Parkinson disease, Alzheimer disease, Friedreich ataxia (FRDA), Leber's hereditary optic neuropathy (LHON), mitochondrial myopathy, encephalopathy, lactic acidosis, and stroke-like episodes (MELAS), Leigh encephalopathy (Leigh Syndrome), Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), Pearson's disease (pancytopenia, multiple organ dysfunction syndrome), and the like. See, e.g., Kevin J. Barnham et al. *Nature Drug Discovery* 2004, 3, 205-214; Michael T. Linl et al. *Nature* 2006, 443, 787-795; Bayani Uttara et al. *Current Neuropharmacology* 2009, 7, 65-74; Toren Finkel et al. *Nature* 2000, 408, 239-247; Jiang et al. *Translational Neurodegeneration* 2015, 4, 14-19; Edens B. M., Miller N., and Ma Y. C. *Front. Cell. Neurosci.*, 2016, 10, 44-59; and D. Simon et al. *Journal of Neuroscience* 2004, 24(8), 1987-1995.

SUMMARY OF THE INVENTION

The novel compounds represented by the following formula (1) strongly suppress cell death due to oxidative stress or mitochondrial dysfunction.

[Item 1]

Provided is a compound represented by formula (1):

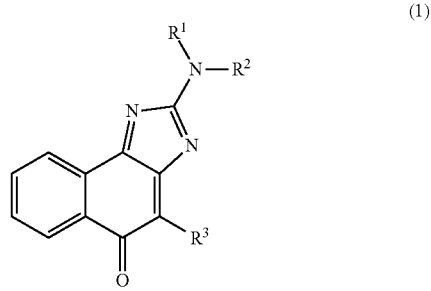

or a reduced form thereof, or a pharmaceutically acceptable salt thereof, wherein
$R^1$ and $R^2$ are each independently
(1) a hydrogen atom,
(2) an optionally substituted $C_{1-6}$alkyl group, an optionally substituted $C_{2-6}$alkenyl group, or an optionally substituted $C_{2-6}$alkynyl group,
(3) an optionally substituted $C_{3-10}$alicyclic hydrocarbon group (wherein the group may contain one or more unsaturated bonds),
(4) an optionally substituted, 3 to 8-membered heterocyclic group (wherein the group may contain one or more unsaturated bonds, and a carbon atom on the ring of the group is bonded with the nitrogen atom to which $R^1$ and $R^2$ are attached), (5) an optionally substituted $C_{6-10}$aryl group, or
(6) an optionally substituted, 5 to 12-membered monocyclic or polycyclic heteroaryl group (with the proviso that in the group, a carbon atom on its ring is bonded with the nitrogen atom to which $R^1$ and $R^2$ are attached), or $R^1$ and $R^2$ may be taken together with the nitrogen atom to which they are attached to form an optionally substituted, 3 to 8-membered, nitrogen-containing heterocycle (wherein the heterocycle may contain one or more unsaturated bonds); and $R^3$ is (1) an optionally substituted $C_{6-10}$aryl group, or
(2) an optionally substituted, 5 to 12-membered monocyclic or polycyclic heteroaryl group (with the proviso that in the group, a carbon atom on its ring is bonded with the carbon atom to which $R^3$ is attached).

[Item 2]

Provided is the compound according to item 1 or a reduced form thereof, or a pharmaceutically acceptable salt thereof, wherein $R^1$ and $R^2$ are each independently (1) a hydrogen atom,
(2) a $C_{1-6}$alkyl group, an optionally substituted $C_{2-6}$alkenyl group, or an optionally substituted $C_{2-6}$alkynyl group (wherein each group is optionally substituted with one to three substituents independently selected from the group consisting of a halogen atom, a $C_{1-6}$alkoxy group, a $C_{3-6}$cycloalkyl group, and a hydroxyl group),
(3) a $C_{3-10}$alicyclic hydrocarbon group (wherein the group may contain one or more unsaturated bonds and the group is optionally substituted with one to three substituents independently selected from the group consisting of a $C_{1-6}$alkyl group, a halogen atom, a $C_{1-6}$alkoxy group, a $C_{3-6}$cycloalkyl group, and a hydroxyl group),
(4) a 3 to 8-membered saturated heterocyclic group (wherein the group may contain one or more unsaturated bonds and the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups),
with the proviso that in the 3 to 8-membered saturated heterocyclic group, a carbon atom on its ring is bonded with the nitrogen atom to which $R^1$ and $R^2$ are attached),
(5) a $C_{6-10}$aryl group (wherein the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups)), or
(6) a 5 to 12-membered monocyclic or polycyclic heteroaryl group (wherein the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups),
with the proviso that in the 5 to 12-membered monocyclic or polycyclic heteroaryl group, a carbon atom on its ring is bonded with the nitrogen atom to which $R^1$ and $R^2$ are attached), or $R^1$ and $R^2$ may be taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a halogen atom, a $C_{1-6}$alkyl group, a $C_{1-6}$alkoxy group, and a hydroxyl group);

$R^3$ is (1) a $C_{6-10}$aryl group (wherein the group is optionally substituted with one to seven substituents independently selected from the group consisting of
(a) a halogen atom,
(b) a hydroxyl group,
(c) a cyano group,
(d) a $C_{1-6}$alkylsulfonyl group (wherein the group is optionally substituted with one to three substituents independently selected from the group consisting of a halogen atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(f) a $C_{1-6}$alkylcarbonyl group (wherein the group is optionally substituted with one to three substituents independently selected from the group consisting of a halogen atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(j) —N($R^4$)COR$^5$,
(k) —CONR$^6$R$^7$,
(l) —S(O)$_2$NR$^8$R$^9$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or two or more substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of (a) a halogen atom,
(b) a hydroxyl group,
(c) a cyano group,
(d) a $C_{1-6}$alkylsulfonyl group (wherein the group is optionally substituted with one to three substituents independently selected from the group consisting of a halogen atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(f) a $C_{1-6}$alkylcarbonyl group (wherein the group is optionally substituted with one to three substituents independently selected from the group consisting of a halogen atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(j) a $C_{6-10}$aryl group (wherein the group is optionally substituted with one to three substituents independently selected from the group consisting of a halogen atom, a $C_{1-6}$alkoxy group, a $C_{3-6}$cycloalkyl group, and a hydroxyl group),
(k) —N($R^{10}$)CO$R^{11}$,
(l) —CON$R^{12}R^{13}$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or two or more substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and R 9 and $R^{12}$ and $R^{13}$ each independently may be taken together to form a 4 to 10-membered, nitrogen-containing heterocycle.

[Item 3]
Provided is the compound according to item 1 or 2 or a reduced form thereof, or a pharmaceutically acceptable salt thereof, wherein $R^3$ is (1) a $C_{6-10}$aryl group (wherein the group is optionally substituted with one to seven substituents independently selected from the group consisting of (a) a halogen atom,
(b) a cyano group,
(c) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(e) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(f) —N($R^4$)CO$R^5$,
(g) —CON$R^6R^7$,
(h) —S(O)$_2$N$R^8R^9$,
(i) an amino group (wherein the group is optionally substituted with one or two $C_{1-6}$alkyl groups), and
(j) a 4 to 7-membered cyclic amino group (wherein the group is optionally substituted with one or two $C_{1-6}$alkyl groups), or two substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of (a) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(b) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(c) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{6-10}$aryl group (wherein the group is optionally substituted with one to three substituents independently selected from the group consisting of a halogen atom, a $C_{1-6}$alkoxy group, a $C_{3-6}$cycloalkyl group, and a hydroxyl group),
(e) —N($R^{10}$)CO$R^{11}$,
(f) —CON$R^{12}R^{13}$,
(g) an amino group (wherein the group is optionally substituted with one or two $C_{1-6}$alkyl groups), and
(h) a 4 to 7-membered cyclic amino group (wherein the group is optionally substituted with one or two $C_{1-6}$alkyl groups), or two substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$, and $R^{12}$ and $R^{13}$ each independently may be taken together to form a 4 to 10-membered, nitrogen-containing heterocycle.

[Item 4]

Provided is the compound according to any one of items 1 to 3 or a reduced form thereof, or a pharmaceutically acceptable salt thereof, wherein $R^3$ is (1) a $C_{6-10}$aryl group (wherein the group is optionally substituted with one to seven substituents independently selected from the group consisting of
(a) a halogen atom,
(b) a cyano group,
(c) a $C_{1-6}$alkyl group (wherein the group is optionally substituted with one to three substituents independently selected from the group consisting of a halogen atom and a $C_{1-6}$alkoxy group),
(d) a $C_{1-6}$alkoxy group (wherein the group is optionally substituted with one to three halogen atoms),
(e) —N($R^4$)CO$R^5$,
(f) —CON$R^6R^7$,
(g) —S(O)$_2$N$R^8R^9$
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or two substituents on the $C_{6-10}$aryl group may be joined to form a 5 to 8-membered non-aromatic heterocycle (wherein the 5 to 8-membered non-aromatic heterocycle is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of
(a) a $C_{1-6}$alkyl group,
(b) a $C_{1-6}$alkoxy group,
(c) a $C_{3-10}$cycloalkoxy group,
(d) a $C_{6-10}$aryl group,
(e) —N($R^{10}$)CO$R^{11}$,
(f) —CON$R^{12}R^{13}$,
(g) an amino group (wherein the group is optionally substituted with one or two $C_{1-6}$alkyl groups), and
(h) a 4 to 7-membered cyclic amino group (wherein the group is optionally substituted with one or two $C_{1-6}$alkyl groups), or two substituents on the 5 to 12-membered monocyclic or polycyclic heteroaryl group may be joined to form a 5 to 8-membered non-aromatic heterocycle (wherein the 5 to 8-membered non-aromatic heterocycle is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group, or $R^6$ and $R^7$, $R^8$ and $R^9$, and $R^{12}$ and $R^{13}$ each independently may be taken together to form a 4 to 10-membered, nitrogen-containing heterocycle.

[Item 5]

Provided is the compound according to any one of items 1 to 4 or a reduced form thereof, or a pharmaceutically acceptable salt thereof, wherein $R^1$ and $R^2$ are each independently (1) a hydrogen atom,
(2) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group), or
(3) a $C_{3-10}$alicyclic hydrocarbon group (wherein the group may contain one or more unsaturated bonds and the group is optionally substituted with one to three substituents independently selected from the group consisting of a halogen atom, a $C_{1-6}$alkyl group, a $C_{1-6}$alkoxy group, a $C_{3-6}$cycloalkyl group, and a hydroxyl group), or $R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a halogen atom, a $C_{1-6}$alkyl group, a $C_{1-6}$alkoxy group, and a hydroxyl group).

[Item 6]

Provided is the compound according to any one of items 1 to 5 or a reduced form thereof, or a pharmaceutically acceptable salt thereof, wherein $R^1$ and $R^2$ are each independently a hydrogen atom, or a $C_{1-6}$alkyl group (wherein the group is optionally substituted with one to three $C_{1-6}$alkoxy groups), or $R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a $C_{1-6}$alkyl group, a $C_{1-6}$alkoxy group, and a hydroxyl group).

[Item 7]

Provided is the compound according to any one of items 1 to 6 or a reduced form thereof, or a pharmaceutically acceptable salt thereof, wherein $R^1$ and $R^2$ are each independently an optionally substituted $C_{1-6}$alkyl group, or $R^1$ and $R^2$ may be taken together with the nitrogen atom to which they are attached to form an optionally substituted, 3 to 8-membered, nitrogen-containing heterocycle (the heterocycle may contain one or more unsaturated bonds), and $R^3$ is an optionally substituted $C_{6-10}$aryl group, or an optionally substituted, 5 to 12-membered monocyclic or polycyclic heteroaryl group (with the proviso that in the group, a carbon atom on its ring is bonded with the carbon atom to which $R^3$ is attached).

[Item 8]

Provided is the compound according to any one of items 1 to 7 or a reduced form thereof, or a pharmaceutically acceptable salt thereof, wherein $R^1$ and $R^2$ are each independently a $C_{1-6}$alkyl group (wherein the group is optionally substituted with one $C_{1-6}$alkoxy group), or $R^1$ and $R^2$ may be taken together with the nitrogen atom to which they are attached to form a 3 to 8-membered, nitrogen-containing heterocycle (wherein the heterocycle may contain one or more unsaturated bonds and the heterocycle is optionally substituted with one $C_{1-6}$alkyl group);

$R^3$ is (1) a $C_{6-10}$aryl group (wherein the group is optionally substituted with one to seven substituents independently selected from the group consisting of:
(a) halogen atom,
(b) cyano group,
(c) a $C_{1-6}$alkyl group (wherein the group is optionally substituted with one to three substituents independently selected from the group consisting of a halogen atom and a $C_{1-6}$alkoxy group),
(d) a $C_{1-6}$alkoxy group (wherein the group is optionally substituted with one to three halogen atoms),
(e) —N($R^4$)CO$R^5$,
(f) —CONR$^6$R$^7$,
(g) —S(O)$_2$NR$^8$R$^9$,
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or two substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of
(a) a $C_{1-6}$alkyl group,
(b) a $C_{1-6}$alkoxy group,
(c) a $C_{6-10}$aryl group, and
(d) a 4 to 7-membered cyclic amino group (wherein the group is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, and $R^7$ are each independently a hydrogen atom or a $C_{1-10}$alkyl group, and $R^8$ and $R^9$ may be taken together to form a 4 to 10-membered, nitrogen-containing heterocycle (wherein the heterocycle may contain one or more unsaturated bonds).

[Item 9]

Provided is the compound according to any one of items 1 to 8 or a reduced form thereof, or a pharmaceutically acceptable salt thereof, wherein $R^1$ and $R^2$ are each independently a hydrogen atom, an unsubstituted $C_{1-6}$alkyl group, or a $C_{1-6}$alkyl group substituted with one to three substituents independently selected from the group consisting of a halogen atom, a $C_{1-6}$alkoxy group, a $C_{3-6}$cycloalkyl group, and a hydroxyl group; or $R^1$ and $R^2$ may be taken together with the nitrogen atom to which they are attached to form a 3 to 8-membered, saturated nitrogen-containing heterocycle (wherein the heterocycle is optionally substituted with one or two groups independently selected from the group consisting of a halogen atom, a $C_{1-6}$alkyl group, a $C_{1-6}$alkoxy group, and a hydroxyl group).

[Item 10]

Provided is the compound according to any one of items 1 to 9 or a reduced form thereof, or a pharmaceutically acceptable salt thereof, wherein $R^3$ is (1) a $C_{6-10}$aryl group (wherein the group is optionally substituted with one to four substituents independently selected from the group consisting of
(a) a halogen atom,
(b) a cyano group,
(c) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(e) —N($R^4$)CO$R^5$,
(f) —CONR$^6$R$^7$,
(g) —S(O)$_2$NR$^8$R$^9$,
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or two or more substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of
(a) a halogen atom,
(b) a cyano group,
(c) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group), (e) a $C_{6-10}$aryl group (wherein the group is optionally substituted with one to three substituents independently selected from the group consisting of a halogen atom, a $C_{1-6}$alkoxy group, a $C_{3-6}$cycloalkyl group, and a hydroxyl group), (f) —N(R$^{10}$)COR$^{11}$, (g) —CONR$^{12}$R$^{13}$, (h) an amino group (wherein the group is optionally substituted with one or two $C_{1-6}$alkyl groups), and (i) a 4 to 7-membered cyclic amino group (wherein the group is optionally substituted with one or two $C_{1-6}$alkyl groups), or two or more substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups), with the proviso that in the 5 to 12-membered monocyclic or polycyclic heteroaryl group, a carbon atom on its ring is bonded with the carbon atom to which R$^3$ is attached).

[Item 11]

Provided is the compound according to any one of items 1 to 10 or a reduced form thereof, or a pharmaceutically acceptable salt thereof, wherein the compound is selected from the group consisting of the following compounds of formulas Example 1

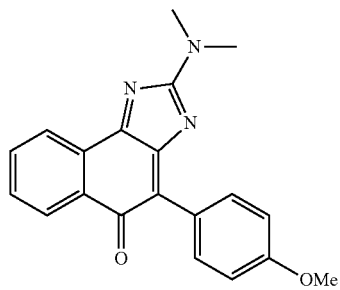

Example 2

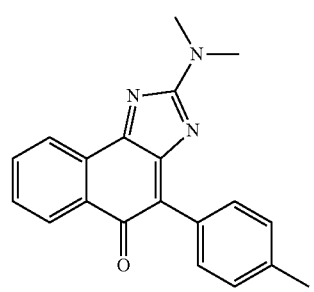

-continued

Example 3

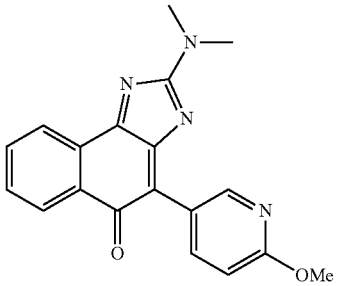

Example 4

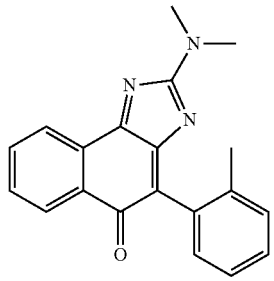

Example 5

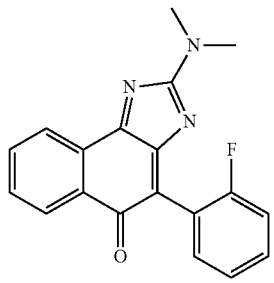

Example 6

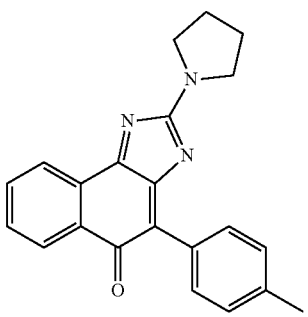

Example 7

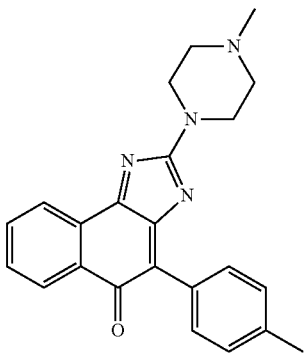

Example 8
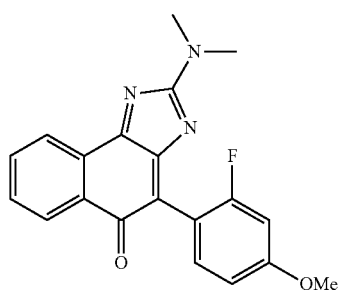
Example 9
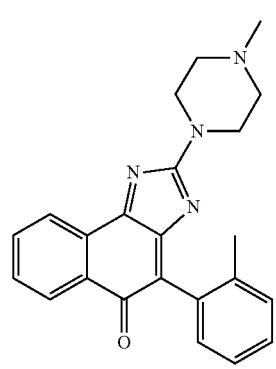
Example 10
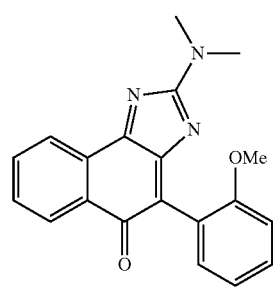
Example 11
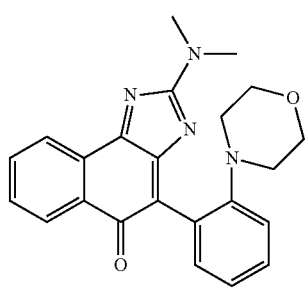
Example 12
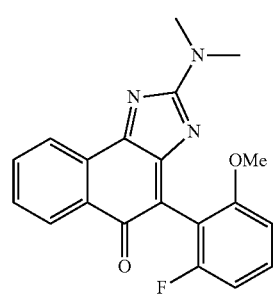
Example 13
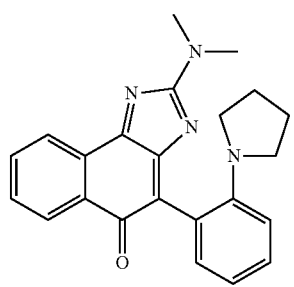
Example 14
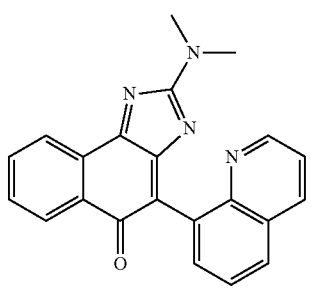
Example 15
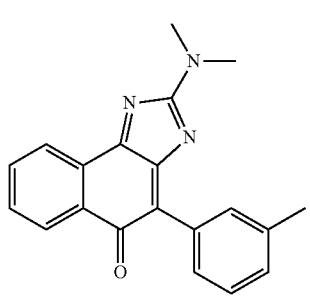
Example 16
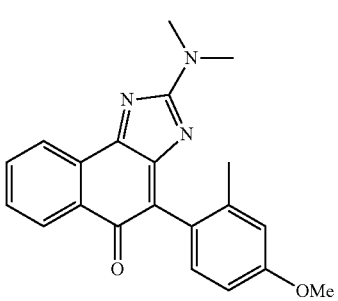
Example 17
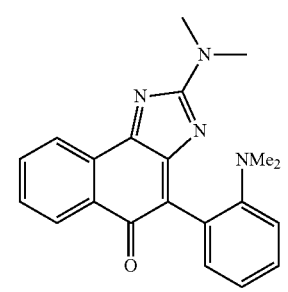

Example 18
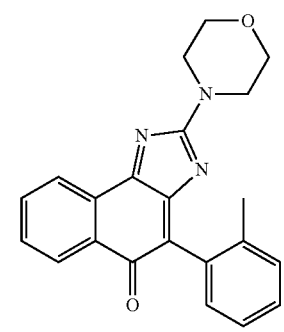
Example 19
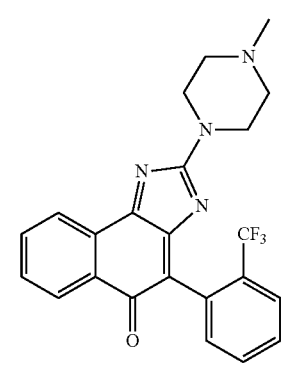
Example 20
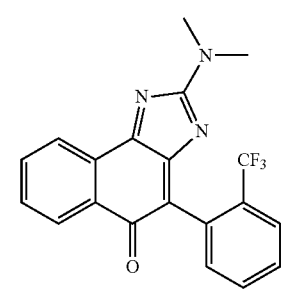
Example 21
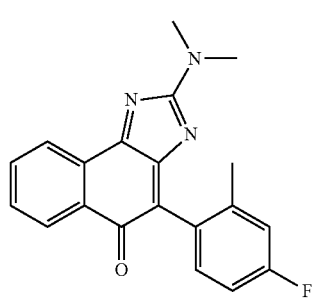
Example 22
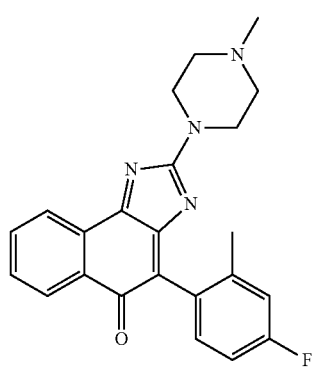
Example 23
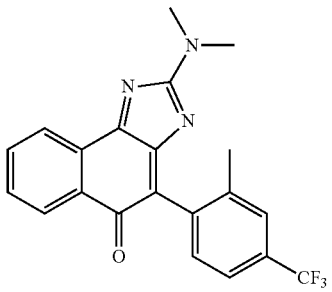
Example 24
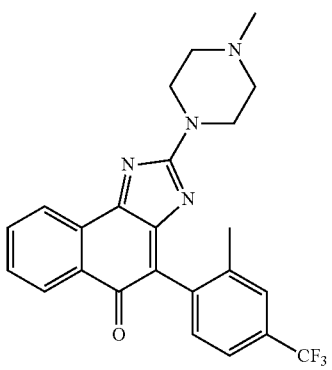
Example 25
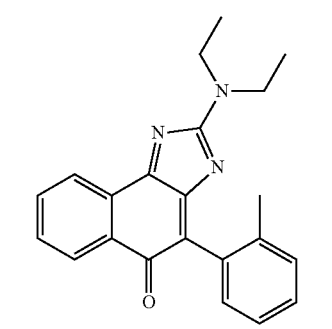
Example 26
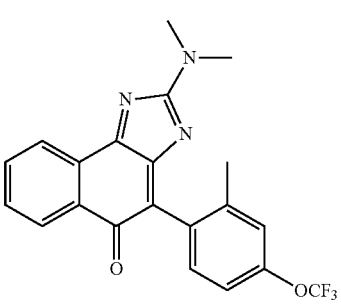
Example 27
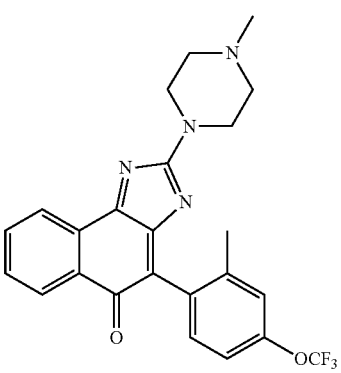

Example 28
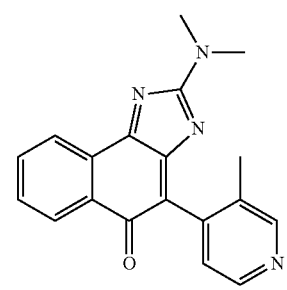
Example 29
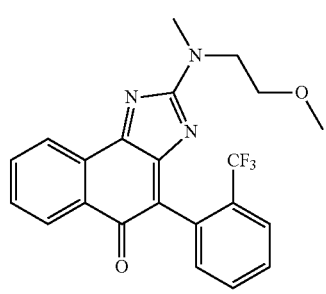
Example 30
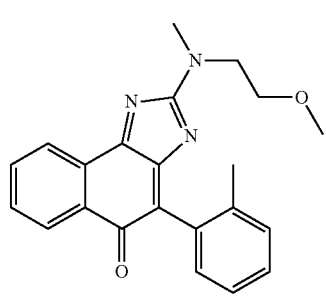
Example 31
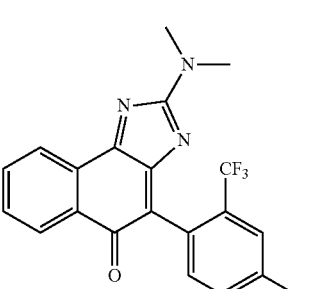
Example 32
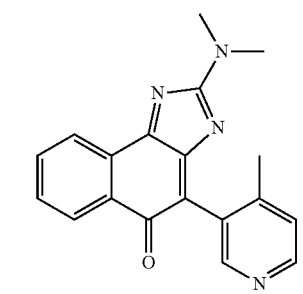
Example 33
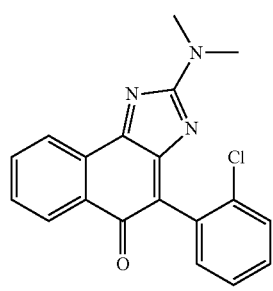
Example 34
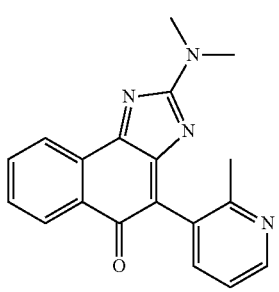
Example 35
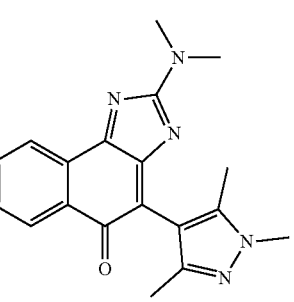
Example 36
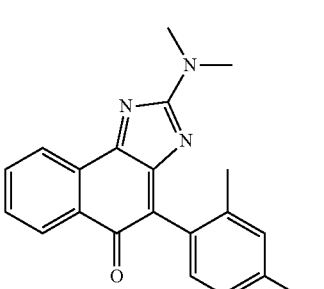
Example 37
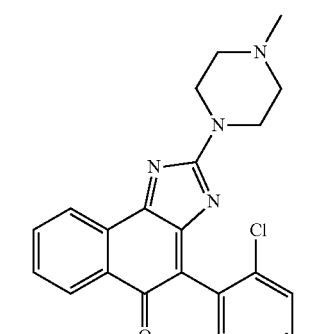

Example 38
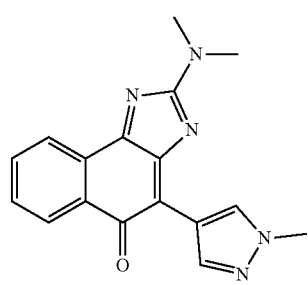
Example 39
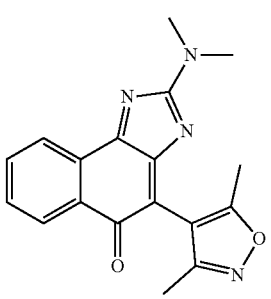
Example 40
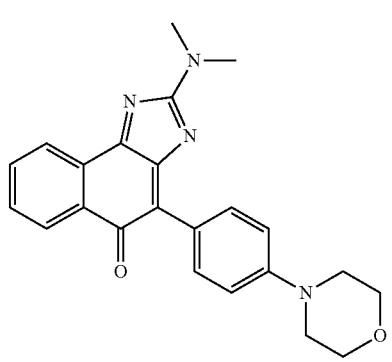
Example 41
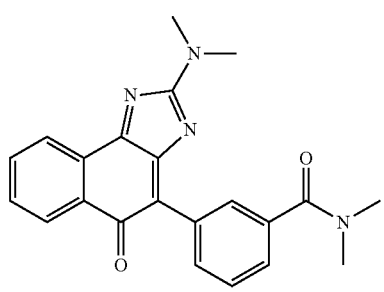
Example 42
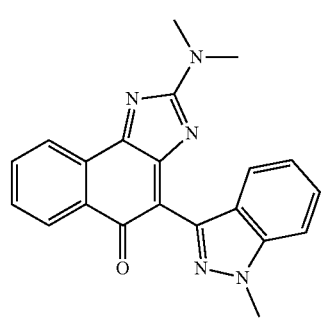
Example 43
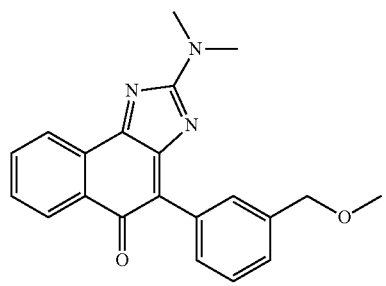
Example 44
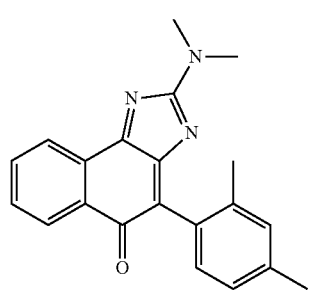
Example 45
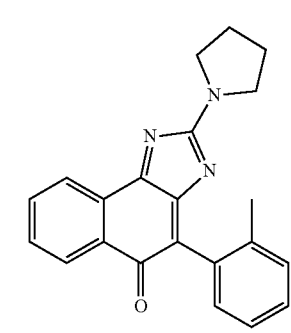
Example 46
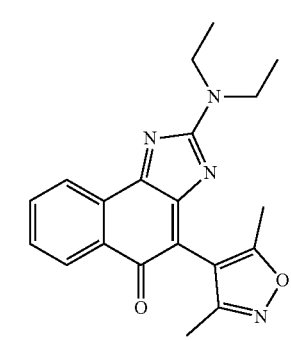
Example 47
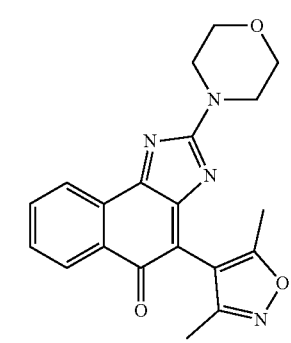

Example 48
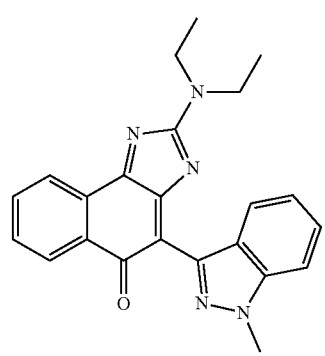
Example 49
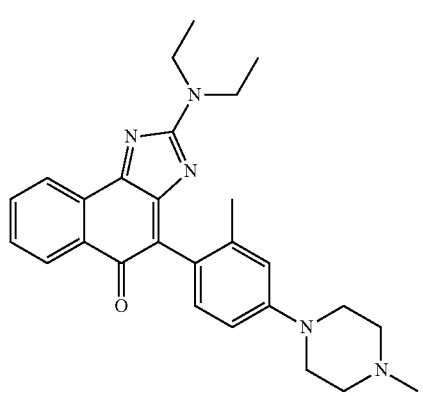
Example 50
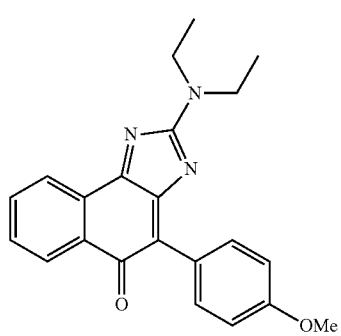
Example 51
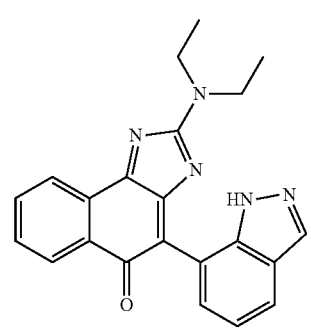
Example 52
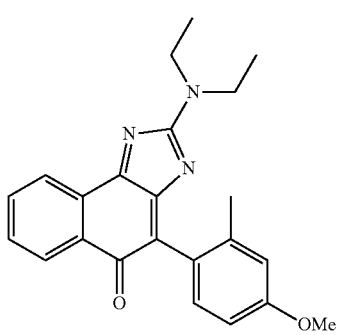
Example 53
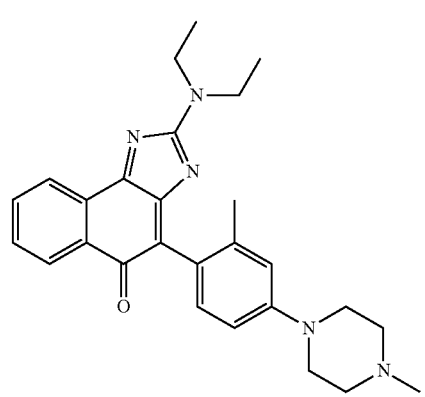
Example 54
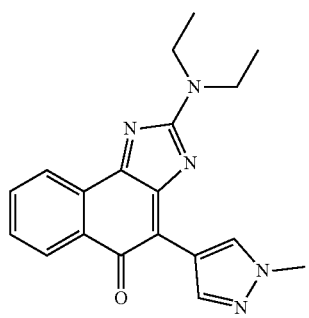
Example 55
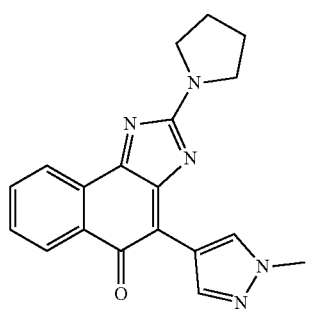

Example 56
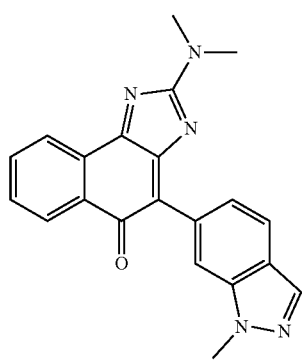
Example 57
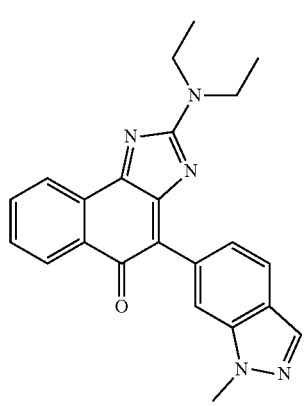
Example 58
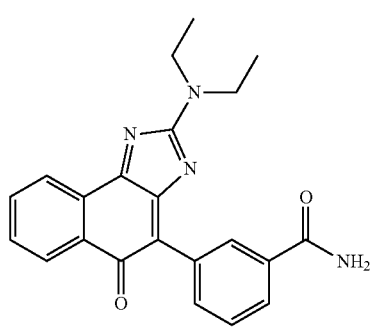
Example 59
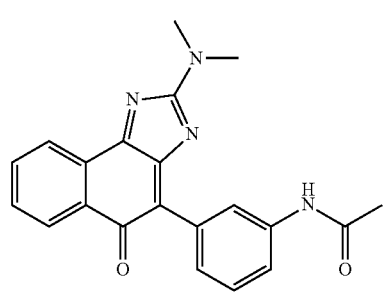
Example 60
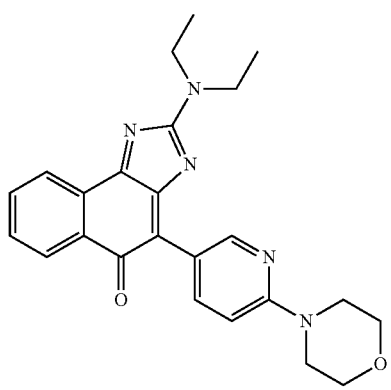
Example 61
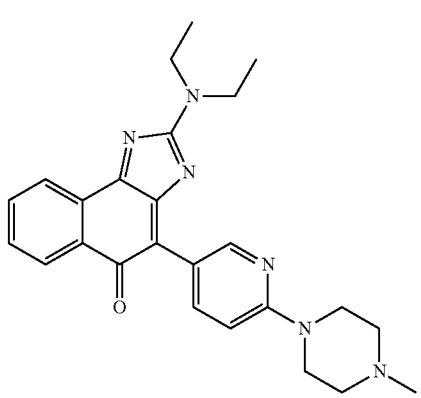
Example 62
Example 63
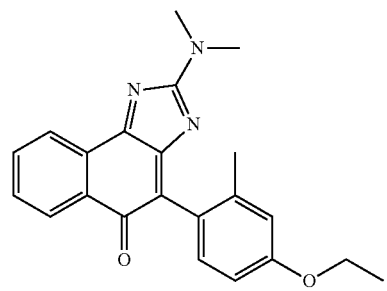

Example 64
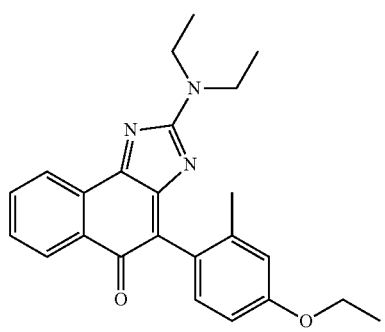
Example 65
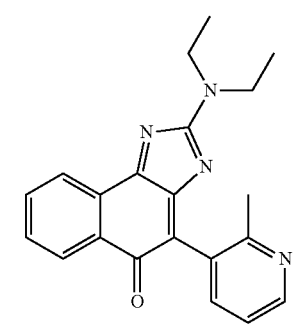
Example 66
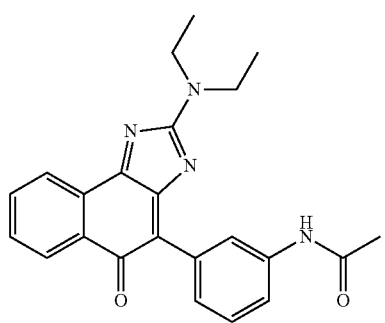
Example 67
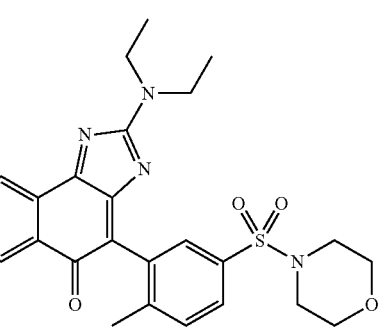
Example 68
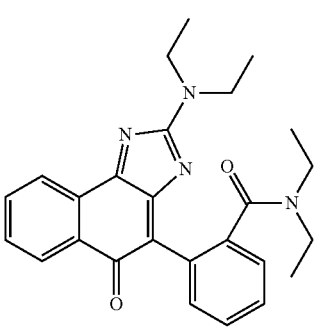
Example 69
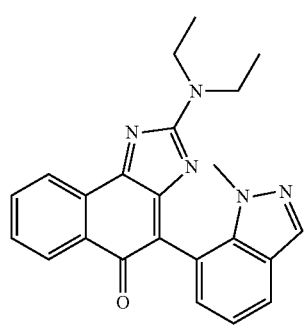
Example 70
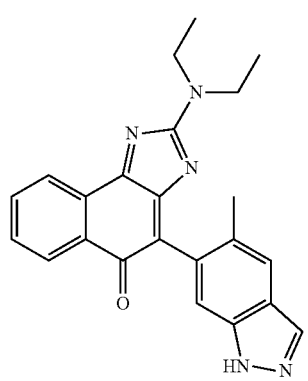
Example 71
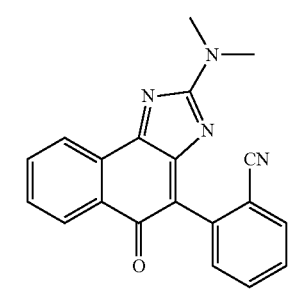
Example 72
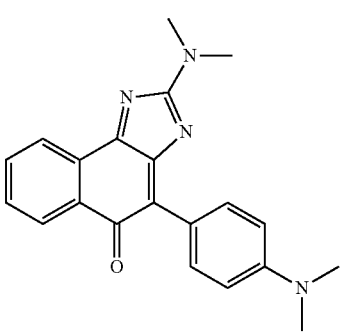
Example 73
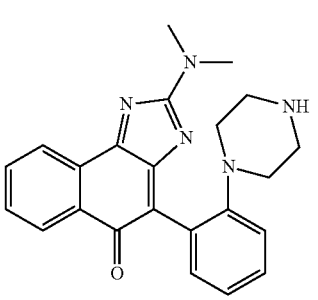

Example 74
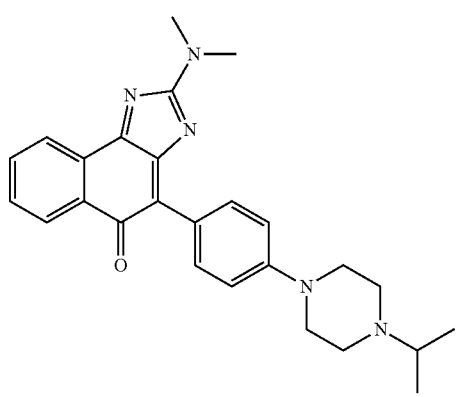
Example 75
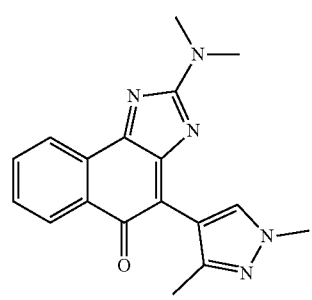
Example 76
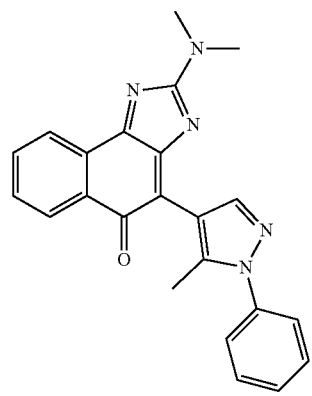
Example 77
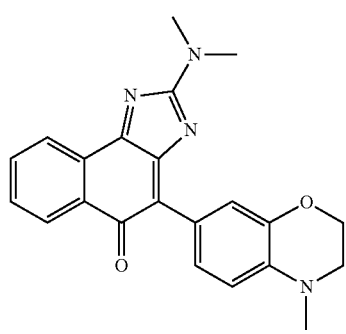
Example 78
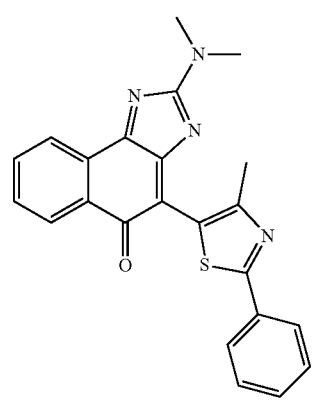
Example 79
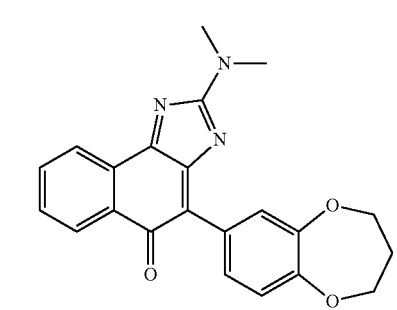
Example 80
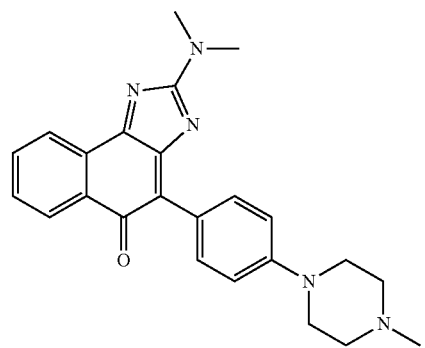
Example 81
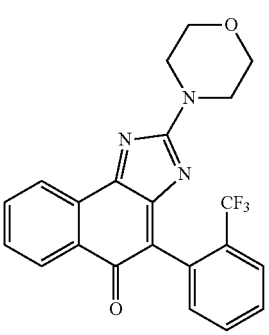

Example 82
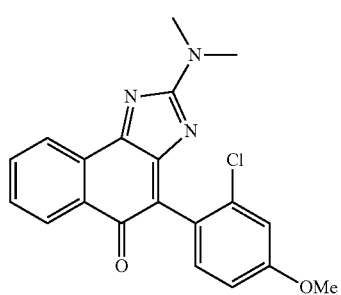
Example 83
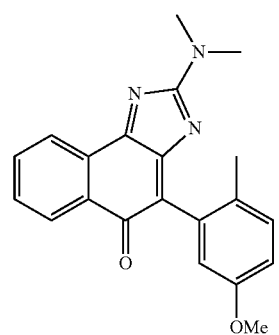
Example 84
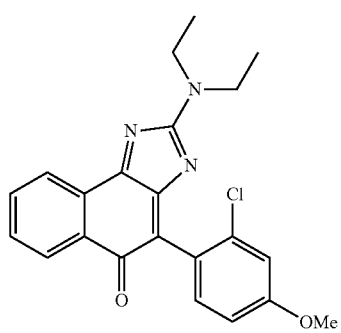
Example 85
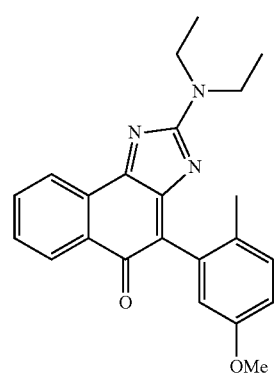
Example 86
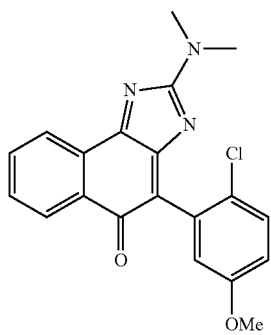
Example 87
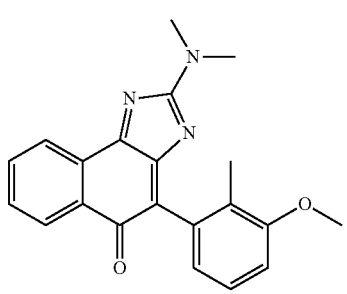
Example 88
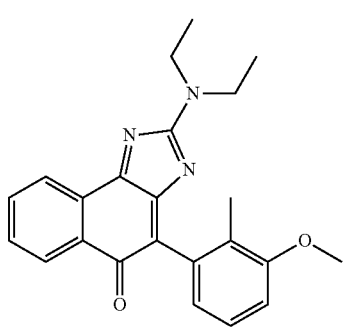
Example 89
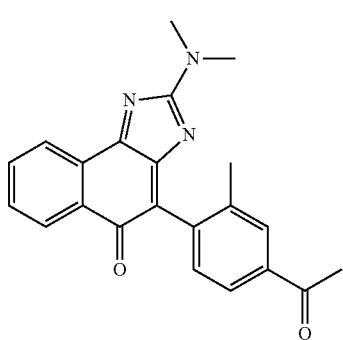
Example 90
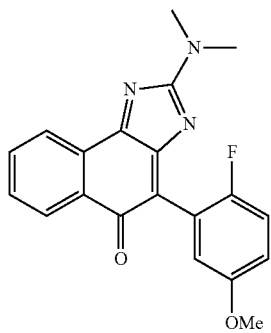

Example 91

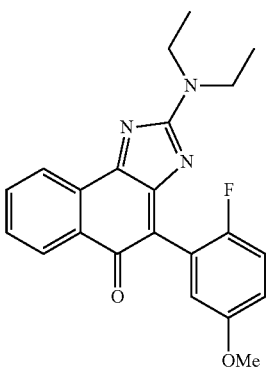

Example 92

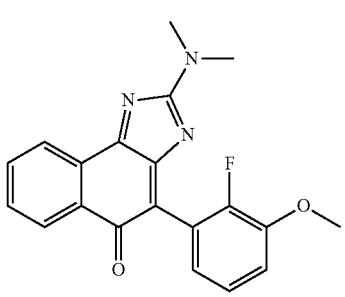

Example 93

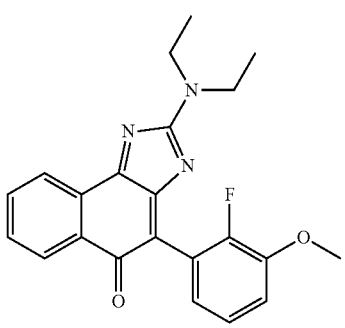

Example 94

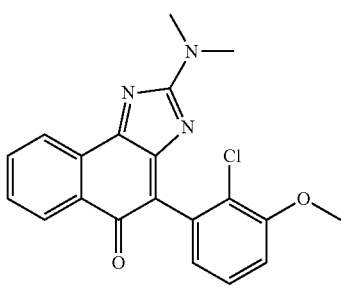

Example 95

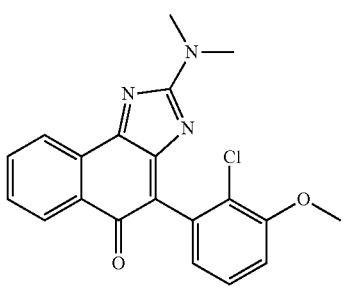

Example 96

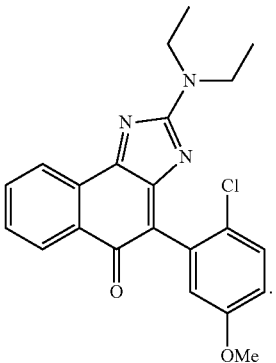

[Item 12]
Provided is the compound according to any one of items 1 to 11 or a reduced form thereof, or a pharmaceutically acceptable salt thereof, wherein the compound is selected from the group consisting of the following compounds:
2-(dimethylamino)-4-(4-methylphenyl)-5H-naphth[1,2-d]imidazol-5-one;
2-(dimethylamino)-4-(2-methylphenyl)-5H-naphth[1,2-d]imidazol-5-one;
4-(2-methylphenyl)-2-(4-methylpiperazin-1-yl)-5H-naphth[1,2-d]imidazol-5-one;
2-(dimethylamino)-4-[2-(morpholin-4-yl)phenyl]-5H-naphth[1,2-d]imidazol-5-one;
2-(dimethylamino)-4-[2-(trifluoromethyl)phenyl]-5H-naphth[1,2-d]imidazol-5-one;
2-(dimethylamino)-4-[2-methyl-4-(trifluoromethyl)phenyl]-5H-naphth[1,2-d]imidazol-5-one;
2-(diethylamino)-4-(2-methyl phenyl)-5H-naphth[1,2-d]imidazol-5-one;
2-(dimethylamino)-4-[2-methyl-4-(trifluoromethoxy)phenyl]-5H-naphth[1,2-d]imidazol-5-one;
4-(2-chlorophenyl)-2-(dimethylamino)-5H-naphth[1,2-d]imidazol-5-one;
2-(dimethylamino)-4-(1,3,5-trimethyl-1H-pyrazol-4-yl)-5H-naphth[1,2-d]imidazol-5-one;
2-[(2-dimethylamino)-5-oxo-5H-naphth[1,2-d]imidazol-4-yl]benzonitrile;
4-[(2-dimethylamino)-5-oxo-5H-naphth[1,2-d]imidazol-4-yl]-3-methylbenzonitrile; and
2-(dimethylamino)-4-(2-chloro-4-methoxyphenyl)-5H-naphth[1,2-d]imidazol-5-one.

[Item 13]
Provided is a pharmaceutical composition comprising a compound according to any one of items 1 to 12 or a reduced form thereof or a pharmaceutically acceptable salt thereof.

[Item 14]
Provided is a therapeutic agent and/or a prophylactic agent for a disease caused by or aggravated by oxidative stress or mitochondrial dysfunction, wherein the compound according to any one of items 1 to 12 or a reduced form thereof or a pharmaceutically acceptable salt thereof or the pharmaceutical composition according to item 13 is used as an active ingredient.

[Item 15]
Provided is a method of treating and/or preventing a disease caused by or aggravated by oxidative stress or mitochondrial dysfunction, characterized by administering to a patient in need of the treatment and/or prevention a therapeutically effective amount of a compound according to any one of items 1 to 12 or a reduced form thereof or a pharmaceutically acceptable salt thereof or a therapeutically effective amount of a pharmaceutical composition according to item 13.

[Item 16]

Provided is the compound according to any one of items 1 to 12 or a reduced form thereof or a pharmaceutically acceptable salt thereof or the pharmaceutical composition according to item 13 for use in treating and/or preventing a disease caused by or aggravated by oxidative stress or mitochondrial dysfunction.

[Item 17]

Provided is the therapeutic agent and/or the prophylactic agent according to item 14, wherein the disease caused by or aggravated by oxidative stress or mitochondrial dysfunction is amyotrophic lateral sclerosis (ALS), Huntington disease, Parkinson disease, Friedreich ataxia (FRDA), Alzheimer disease, Leber's hereditary optic neuropathy (LHON), mitochondrial myopathy, encephalopathy, lactic acidosis, and stroke-like episodes (MELAS), Leigh Syndrome, Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), or Pearson's disease (pancytopenia, multiple organ dysfunction syndrome).

[Item 18]

Provided is the method of treating and/or preventing according to item 15, wherein the disease caused by or aggravated by oxidative stress or mitochondrial dysfunction is amyotrophic lateral sclerosis (ALS), Huntington disease, Parkinson disease, Friedreich ataxia (FRDA), Alzheimer disease, Leber's hereditary optic neuropathy (LHON), mitochondrial myopathy, encephalopathy, lactic acidosis, and stroke-like episodes (MELAS), Leigh Syndrome, Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), or Pearson's disease (pancytopenia, multiple organ dysfunction syndrome).

[Item 19]

Provided is the compound according to item 16 or a reduced form thereof, or a pharmaceutically acceptable salt thereof, wherein the disease caused by or aggravated by oxidative stress or mitochondrial dysfunction is amyotrophic lateral sclerosis (ALS), Huntington disease, Parkinson disease, Friedreich ataxia (FRDA), Alzheimer disease, Leber's hereditary optic neuropathy (LHON), mitochondrial myopathy, encephalopathy, lactic acidosis, and stroke-like episodes (MELAS), Leigh Syndrome, Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), or Pearson's disease (pancytopenia, multiple organ dysfunction syndrome).

In another aspect, provided is the compound according to any one of items 1 to 12 or a reduced form thereof or a pharmaceutically acceptable salt thereof or the pharmaceutical composition of item 13 for the manufacture of a medicament for treating and/or preventing a disease caused by or aggravated by oxidative stress or mitochondrial dysfunction.

In the present disclosure, it is intended that one or a plurality of the above-mentioned aspects, items, embodiments, or characteristics can be further arbitrarily combined and provided in addition to clearly expressed combinations. Still further, embodiments and advantages of the present disclosure will be recognized by those skilled in the art from the following detailed descriptions.

The compounds of the present disclosure are useful as a novel therapeutic and/or prophylactic agent for a disease caused by or aggravated by oxidative stress or mitochondrial dysfunction (e.g., amyotrophic lateral sclerosis, Huntington disease, Parkinson disease, Friedreich ataxia (FRDA), Alzheimer disease, atherosclerosis, myocardial infarction, cerebral infarction, disease related to aging, diabetes, alcoholic liver injury, chronic obstructive pulmonary disease, Leber's hereditary optic neuropathy (LHON), mitochondrial myopathy, encephalopathy, lactic acidosis, and stroke-like episodes (MELAS), Leigh Syndrome, and Kearns-Sayre syndrome (KSS)).

DETAILED DESCRIPTION

The compounds of the present disclosure encompass, in addition to compounds of formula (1), compounds of formulae (2) and (3), which are the reduced forms thereof.

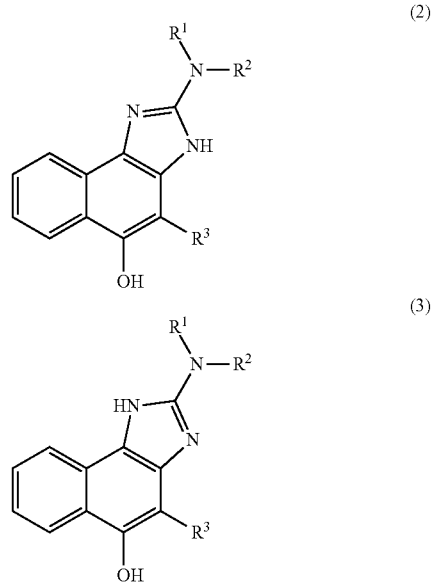

The compounds of the present disclosure may be present in the form of a hydrate and/or a solvate. These hydrates and/or solvates are also encompassed by the compounds of the present disclosure.

Since the compounds of formulae (1), (2), and (3) may have one, or optionally one or more, asymmetric carbon atom(s) and may result in geometrical isomerism or axial chirality, the compounds may be present as one or more of several types of stereoisomers. In the present disclosure, these individual stereoisomers, and mixtures and racemates thereof are also encompassed by the compounds represented by formulae (1), (2), and (3) of the present disclosure. Further, a deuterated form in which any one or more hydrogen atoms of a compound represented by the general formula (1), (2), or (3) has been converted to or is enriched (beyond naturally-occurring amounts) for a deuterium atom (D) is also encompassed by the compound represented by the general formula (1), (2), or (3).

Examples of a "pharmaceutically acceptable salt" of a compound represented by formulae (1), (2), or (3) include salts with an inorganic or organic acid. In some embodiments, salts with an inorganic acid include, without limitation, hydrochloride, hydrobromide, nitrate, sulfate, phosphate, and the like. In some embodiments, salts with an organic acid include, without limitation, formate, acetate, trifluoroacetate, propionate, lactate, tartrate, oxalate, ascorbate, fumarate, maleate, citrate, malonate, methanesulfonate, benzenesulfonate, p-toluenesulfonate, and the like.

The present disclosure also encompasses prodrugs of compounds herein or pharmaceutically acceptable salts thereof. In general, the prodrugs are functional derivatives of compounds herein that can be readily converted to an active compound in vivo.

As used herein, unless otherwise specified, the term "solvate" refers to a compound herein, or a salt thereof, that further comprises an amount of a solvent in a stoichiometric or non-stoichiometric ratio wherein the solvent is bound by noncovalent intermolecular forces. In the present disclosure, one or more types of the solvates can be used in combination. When the solvent is water, the solvate is a hydrate.

In the present specification, the number of substituents of a group defined by "optionally substituted" is not particularly limited if the group is substitutable, and the substitutents can be one or plural. In addition, unless otherwise indicated, the description for each group is also applied when the group is one part of or a substituent on other groups. The number of carbon atoms in the definition of "substituent" may be described as, for example, "$C_{1-6}$" or the like. Specifically, the description "$C_{1-6}$alkyl" is synonymous with an alkyl group having a carbon number from 1 to 6. In addition, in the present specification, a substituent for which the term "optionally substituted" is not clearly stated refers to an "unsubstituted" substituent.

A "halogen atom" as used herein refers to a fluorine atom, a chlorine atom, a bromine atom, or an iodine atom. Preferably, it is a fluorine atom or a chlorine atom.

An "alkyl group" as used herein refers to a linear or branched, saturated hydrocarbon group. For example, a "$C_{1-4}$alkyl group," a "$C_{1-6}$alkyl group," or a "$C_{1-10}$alkyl group" refers to an alkyl group having 1 to 4, 1 to 6, or 1 to 10 carbon atoms, respectively. In some embodiments, the "$C_{1-4}$alkyl group" includes a methyl group, an ethyl group, a propyl group, an isopropyl group, a butyl group, an isobutyl group, a sec-butyl group, a tert-butyl group, and the like. An alkyl group preferably includes a "$C_{1-6}$alkyl group" and more preferably a "$C_{1-4}$alkyl group." In some embodiments, the "$C_{1-6}$alkyl group" includes, in addition to those described above, a pentyl group, an isopentyl group, a neopentyl group, a hexyl group, and the like. In some embodiments, the "$C_{1-10}$alkyl group" further includes, in addition to those described above, a heptyl group, an octyl group, and the like.

An "alkenyl group" as used herein refers to a linear or branched, unsaturated hydrocarbon group that contains at least one double bond. For example, a "$C_{2-6}$ alkenyl group" refers to a linear or branched, unsaturated hydrocarbon group that has two to six carbon atoms and contains one to three double bonds. In some embodiments, the "$C_{2-6}$ alkenyl group" includes, for example, a vinyl group, a propenyl group, a methylpropenyl group, a butenyl group, a methylbutenyl group, a pentenyl group, a hexenyl group, and the like.

An "alkynyl group" as used herein refers to a linear or branched, unsaturated hydrocarbon group that contains at least one triple bond. For example, a "$C_{2-6}$ alkynyl group" refers to a linear or branched, unsaturated hydrocarbon group that has two to six carbon atoms and contains one or more triple bonds. In some embodiments, the "$C_{2-6}$ alkynyl group" includes, for example, a propynyl group, a methyl-propynyl group, a butynyl group, a methylbutynyl group, a pentynyl group, a hexynyl group, and the like.

An "alicyclic hydrocarbon group" as used herein refers to a monocyclic or polycyclic hydrocarbon group in which the ring is an aliphatic hydrocarbon ring. The ring may contain one or more unsaturated bonds, however, the ring is not aromatic. Examples of the "alicyclic hydrocarbon group" include a cycloalkyl group, a cycloalkenyl group, and a cycloalkynyl group. An "alicyclic hydrocarbon group" is optionally substituted. In some embodiments, an "alicyclic hydrocarbon group" may be fused to an aromatic ring (e.g., benzene, naphthalene, pyridine, or the like). For example, a "$C_{3-10}$alicyclic hydrocarbon group" refers to a group in which the alicyclic ring portion has 3 to 10 carbon atoms. In some embodiments, cases where an "alicyclic hydrocarbon group" is fused to an aromatic ring include groups represented by the following:

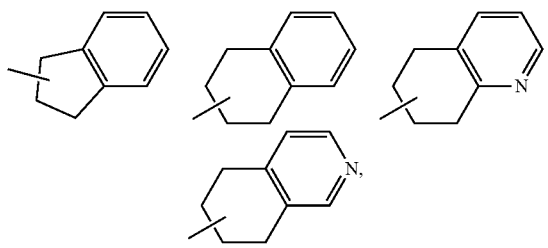

and the like. It should be noted that "$C_{3-10}$" indicates the number of carbon atoms of an alicyclic hydrocarbon group, and therefore, when it is fused, the total number of carbon atoms contained in such a group may be 10 or more.

A "cycloalkyl group" as used herein refers to a monocyclic or polycyclic saturated hydrocarbon group, and also includes fused, bridged, and spirocyclic structures. In some embodiments, a "$C_{3-10}$cycloalkyl group" refers to a cyclic alkyl group having 3 to 10 carbon atoms. For example, the "$C_{3-10}$cycloalkyl group" includes a cyclopropyl group, a cyclobutyl group, a cyclopentyl group, a cyclohexyl group, a cycloheptyl group, a cyclooctyl group, an adamantyl group, and the like. Preferably, it includes a "$C_{3-6}$cycloalkyl group."

A "cycloalkenyl group" as used herein refers to a monocyclic or polycyclic unsaturated hydrocarbon group that contains at least one double bond, and also includes fused, bridged, and spirocyclic structures. In some embodiments, the "$C_{3-10}$cycloalkenyl group" includes a cyclopropenyl group, a methylcyclopropenyl group, a cyclobutenyl group, a methylcyclobutenyl group, a cyclopentenyl group, a cyclohexenyl group, and the like.

A "cycloalkynyl group" as used herein refers to a monocyclic or polycyclic unsaturated hydrocarbon group that contains at least one triple bond, and also includes fused, bridged, and spirocyclic structures. In some embodiments, the "cycloalkynyl group" includes a cyclooctynyl group and the like.

An "alkoxy group" as used herein refers to a linear or branched, saturated hydrocarbon group that is attached to a main skeleton through an oxygen atom. For example, a "$C_{1-6}$alkoxy group" refers to an alkoxy group having 1 to 6 carbon atoms. In some embodiments, the "$C_{1-6}$alkoxy group" includes a methoxy group, an ethoxy group, a propoxy group, a 1-methylethoxy group, a butoxy group, a 2-methylpropoxy group, a 1-methylpropoxy group, a 1,1-dimethylethoxy group, a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, and the like. It preferably includes a "$C_{1-6}$alkoxy group" and more preferably a "$C_{1-3}$alkoxy group."

A "$C_{1-6}$ alkylsulfonyl group" as used herein refers to a —S(O)$_2$R group where R is "$C_{1-6}$ alkyl" as described for "$C_{1-6}$ alkyl group" above. Preferably, it includes a "$C_{1-4}$ alkylsulfonyl group." In some embodiments, the "$C_{1-6}$ alkylsulfonyl group" includes, without limitation, a methylsulfonyl group, an ethylsulfonyl group, a propylsulfonyl group, an isopropylsulfonyl group, a butylsulfonyl group, a pentylsulfonyl group, a hexylsulfonyl group, and the like.

A "$C_{1-6}$ alkylaminosulfonyl group" as used herein refers to a —S(O)$_2$NR($C_{1-6}$ alkyl) group where R is hydrogen or $C_{1-6}$ alkyl and each "$C_{1-6}$ alkyl" moiety in "$C_{1-6}$ alkylaminosulfonyl group" is defined as described in "$C_{1-6}$ alkyl group" above. Preferably, it includes a "$C_{1-4}$ alkylaminosulfonyl group." In some embodiments, the "$C_{1-6}$ alkylaminosulfonyl group" includes, without limitation, mono- or di-$C_{1-6}$alkylaminosulfonyl groups, such as a methylaminosulfonyl group, an ethylaminosulfonyl group, a propylaminosulfonyl group, a dimethylaminosulfonyl group, a diethylaminosulfonyl group, a methylethylaminosulfonyl group, and the like.

A "$C_{1-6}$alkylcarbonyl group" as used herein refers to a —C(O)R group where R is "$C_{1-6}$alkyl" as defined in "$C_{1-6}$alkyl group" above. The "$C_{1-6}$alkylcarbonyl group" includes, preferably, a "$C_{1-4}$alkylcarbonyl group." In some embodiments, the "$C_{1-6}$alkylcarbonyl group" includes, without limitation, a methylcarbonyl group, an ethylcarbonyl group, a propylcarbonyl group, a 1-methylethylcarbonyl group, a butylcarbonyl group, a 2-methylpropylcarbonyl group, a 1-methylpropylcarbonyl group, a 1,1-dimethylethylcarbonyl group, and the like.

A "$C_{3-10}$cycloalkoxy group" as used herein refers to an —OR group where R is "$C_{3-10}$cycloalkyl" as described for "$C_{3-10}$cycloalkyl group" above. Preferably, it includes a "$C_{3-7}$cycloalkoxy group." In some embodiments, the "$C_{3-10}$cycloalkoxy group" includes, without limitation, a cyclopropoxy group, a cyclobutoxy group, a cyclopentyloxy group, a cyclohexyloxy group, a cycloheptyloxy group, and the like.

A "$C_{6-10}$aryl group" as used herein refers to an aromatic hydrocarbon group having a carbon number from 6 to 10 carbon atoms. In some embodiments, the "$C_{6-10}$aryl group" includes, without limitation, a phenyl group, a 1-naphthyl group, a 2-naphthyl group, and the like.

When the term "optionally substituted $C_{6-10}$aryl group" is used, it includes, but is not limited to, $C_{6-10}$aryl where two or more substituents are joined to form a 5 to 8-membered non-aromatic carbocyclic or heterocyclic ring (and may be optionally substituted as further described herein).

A "5 to 8-membered non-aromatic carbocyclic or heterocyclic ring formed by joining two or more substituents on an aryl group or a heteroaryl group" as used herein refers to a 5 to 8-membered non-aromatic carbocyclic or heterocyclic ring having, together with the atoms of an aryl or heteroaryl group, three to six atoms which are independently selected from the group consisting of carbon atoms, nitrogen atoms, oxygen atoms, and sulfur atoms. It is preferably a 5 to 7-membered ring and more preferably a 5 or 6-membered ring. All the nitrogen atoms, oxygen atoms, and sulfur atoms described above are ring-constituting atoms. A 5 to 8-membered non-aromatic carbocyclic or heterocyclic ring, together with the atoms of an aryl or heteroaryl group also encompasses the case where two non-aromatic rings are fused to an aryl or heteroaryl group, and further the case where the two non-aromatic rings are fused to each other. In some embodiments, the "5 to 8-membered non-aromatic carbocyclic or heterocyclic ring (wherein the ring is optionally substituted with one or two $C_{1-6}$alkyl groups) formed by joining two or more substituents on an aryl group or a heteroaryl group" includes, without limitation, rings that are fused to an aryl or heteroaryl portion of a structure represented by the following:

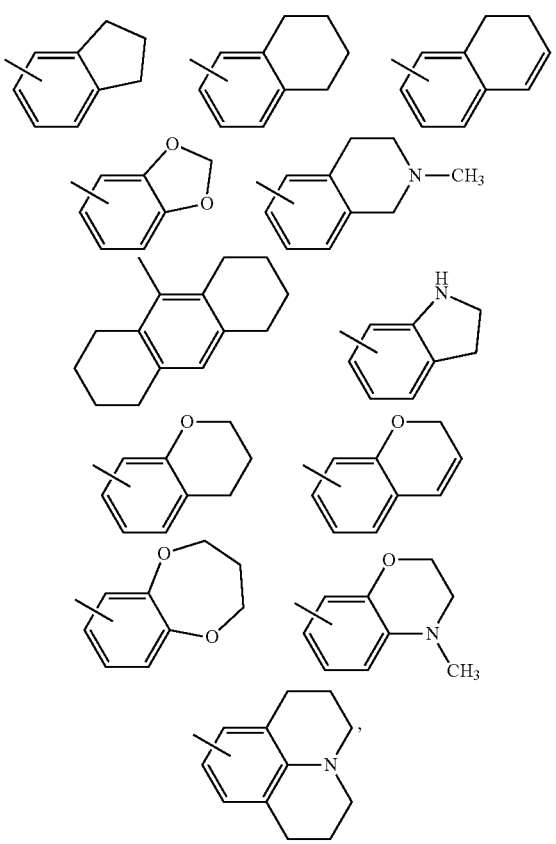

and the like, or by the following:

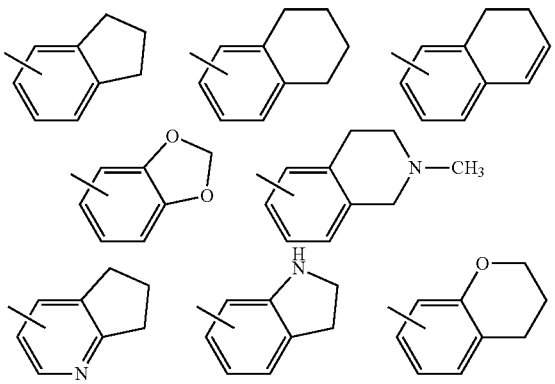

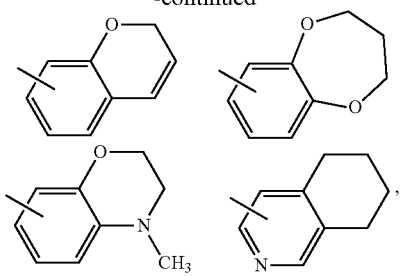

and the like.

A "5 to 8-membered non-aromatic heterocycle formed by joining two substituents on an aryl group or a heteroaryl group," as used herein, refers to a 5 to 8-membered non-aromatic heterocycle having, together with the atoms of an aryl or heteroaryl group, three to six atoms independently selected from the group consisting of carbon atoms, nitrogen atoms, oxygen atoms, and sulfur atoms, with the proviso that at least one or more of the atoms are heteroatom(s). It is preferably a 5 to 7-membered ring and more preferably a 5 or 6-membered ring. All the nitrogen atoms, oxygen atoms, and sulfur atoms described above are ring-constituting atoms. In some embodiments, the "5 to 8-membered non-aromatic heterocycle (wherein the heterocycle is optionally substituted with one or two $C_{1-6}$alkyl groups) formed by joining two substituents on an aryl group or a heteroaryl group" includes, without limitation, rings that are fused to an aryl or heteroaryl portion of a structure represented by the following:

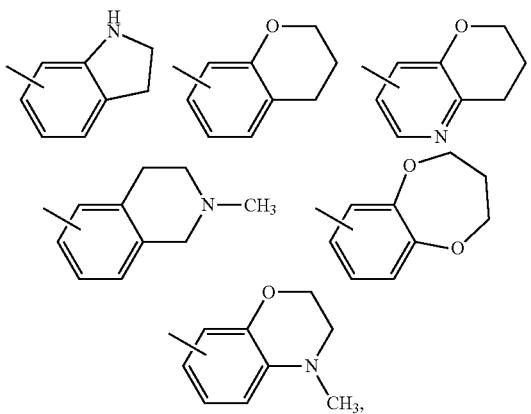

and the like.

A "heteroaryl group" as used herein refers to a 5 to 12-membered monocyclic or polycyclic heteroaryl group (aromatic). The heteroaryl group contains one or more (e.g., one to four) heteroatoms independently selected from the group consisting of nitrogen atoms, sulfur atoms, and oxygen atoms. It preferably includes a 5 to 10-membered monocyclic or polycyclic group and more preferably a 5 or 6-membered monocyclic heteroaryl group. In some embodiments, the "heteroaryl group" includes, without limitation, a pyrrolyl group, a thienyl group, a benzothienyl group, a benzofuranyl group, a benzoxazolyl group, a benzothiazolyl group, a furyl group, an oxazolyl group, a thiazolyl group, an isoxazolyl group, an isothiazolyl group, a benzisoxazolyl group, a benzisothiazolyl group, an imidazolyl group, a pyrazolyl group, a pyridyl group, a pyrazyl group, a pyrimidyl group, a pyridazyl group, a quinolyl group, an isoquinolyl group, a triazolyl group, a triazinyl group, a tetrazolyl group, an indolyl group, an imidazo[1,2-a]pyridyl group, a pyrazolo[1,5-a]pyridyl group, a [1,2,4]triazolo[1,5-a]pyridyl group, a benzimidazolyl group, a quinoxalyl group, a cinnolyl group, a quinazolyl group, an indazolyl group, a naphthyridyl group, a quinolinolyl group, an isoquinolinolyl group, and the like. In some embodiments, the "polycyclic heteroaryl group," wherein in some embodiments the polycyclic heteroaryl group is optionally substituted with a $C_{1-6}$alkyl groups, includes, without limitation, groups having the point of attachment at a position shown below:

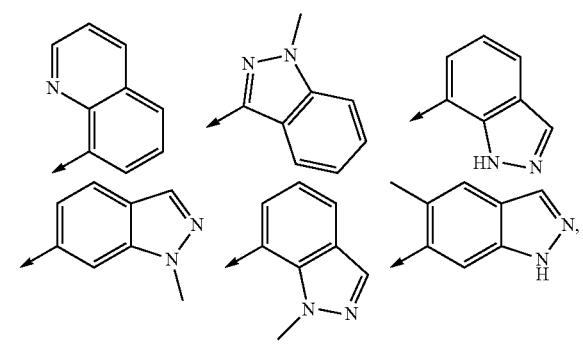

and the like. (The points of arrows represent the position of bonding with the main skeleton.)

A "3 to 8-membered heterocyclic group" as used herein refers to a 3 to 8-membered heterocyclic group having one to three heteroatoms independently selected from the group consisting of nitrogen atoms, oxygen atoms, and sulfur atoms. It is preferably a 4 to 7-membered group and more preferably 5 or 6-membered group. All the nitrogen atoms, oxygen atoms, and sulfur atoms described above are ring-constituting atoms. In some embodiments, the "3 to 8-membered heterocyclic group" includes a pyranyl group, a furyl group, a pyrrolidinyl group, an imidazolidinyl group, a piperidinyl group, a morpholinyl group, a thiomorpholinyl group, a hexamethyleneiminyl group, a thiazolidinyl group, a tetrahydrofuranyl group, a tetrahydropyridinyl group, an oxetanyl group, a tetrahydropyranyl group, and the like. It should be noted that the "3 to 8-membered heterocyclic group" also encompasses a fused, bridged, or spirocyclic heterocyclic groups.

The aforementioned "heterocyclic group" may form a fused ring with a 6-membered aromatic hydrocarbon or a 6-membered heteroaryl. For example, the heterocyclic group also encompasses the case where a 5 or 6-membered heterocyclic group is fused to a 6-membered aromatic hydrocarbon or a 6-membered heteroaryl. An example of a 6-membered aromatic hydrocarbon, to which the 5 or 6-membered heterocyclic group is fused, includes benzo. Examples of 6-membered heteroaryls, to which the 5 or 6-membered heterocyclic group is fused, include pyridine, pyrimidine, pyridazine, and the like. In some embodiments, a fused heterocyclic group includes a dihydroindolyl group, a dihydroisoindolyl group, a dihydropurinyl group, a dihydrobenzodioxinyl group, an indazolyl group, a tetrahydroquinolinyl group, a tetrahydroisoquinolinyl group, a tetrahydronaphthyridinyl group, and the like.

A "3 to 8-membered, nitrogen-containing heterocycle" as used herein refers to a 3 to 8-membered heterocyclic group having, in addition to the at least one nitrogen atom, 0 to 2 heteroatoms independently selected from the group consisting of nitrogen atoms, oxygen atoms, and sulfur atoms. It is preferably a 4 to 7-membered ring and more preferably a 5 or 6-membered ring. All the nitrogen atoms, oxygen atoms, and sulfur atoms described above are ring-constituting atoms. In some embodiments, the "3 to 8-membered, nitrogen-containing heterocycle" includes aziridine, azetidine, pyrrolidine, piperidine, piperazine, morpholine, azepane, homopiperazine, azocane, and the like. It should be noted that the "3 to 8-membered, nitrogen-containing heterocycle" group also encompasses nitrogen-containing fused, bridged, and spirocyclic heterocyclic groups.

A "4 to 10-membered, nitrogen-containing heterocycle" as used herein refers to a 4 to 10-membered heterocyclic group having, in addition to at least one nitrogen atom, 0 to 2 heteroatoms independently selected from the group consisting of nitrogen atoms, oxygen atoms, and sulfur atoms. It is preferably a 4 to 7-membered ring and more preferably a 5 or 6-membered ring. All the nitrogen atoms, oxygen atoms, and sulfur atoms described above are ring-constituting atoms. In some embodiments, the "4 to 10-membered, nitrogen-containing heterocycle" includes azetidine, pyrrolidine, piperidine, piperazine, morpholine, azepane, homopiperazine, azocane, octamethylenimine, and the like. It should be noted that the "4 to 10-membered, nitrogen-containing heterocycle" group also encompasses nitrogen-containing fused, bridged, and spirocyclic heterocyclic groups.

A "4 to 7-membered cyclic amino group" as used herein refers to a saturated or unsaturated 4 to 7-membered cyclic amino group and may further contain, in addition to at least one nitrogen atom, one or two heteroatoms, and/or a carbonyl carbon in the ring, where the heteroatoms are independently selected from the group consisting of nitrogen atoms, oxygen atoms, and sulfur atoms. It is preferably a 5 or 6-membered group. In some embodiments, the "4 to 7-membered cyclic amino group" includes an azetidinyl group, a pyrrolidinyl group, a pyrrolyl group, an imidazolyl group, a piperidinyl group, a piperazinyl group, a morpholinyl group, an azepanyl group, a homopiperazinyl group, and the like. It should be noted that the "4 to 7-membered cyclic amino group" also encompasses fused, bridged, and spirocyclic cyclic amino groups.

A compound of the present disclosure represented by formula (1) or formula (2) or (3), which are reduced forms thereof, include $R^1$, $R^2$, $R^3$, $R^4$, $R^5$, $R^6$, $R^7$, $R^8$, $R^9$, $R^{10}$, $R^{11}$, $R^{12}$, and $R^{13}$ and each are as described below. However, the technical scope of the present disclosure is not limited to the scope of compounds mentioned below.

In some embodiments, $R^1$ and $R^2$ are each independently
(1) a hydrogen atom,
(2) a $C_{1-6}$alkyl group, an optionally substituted $C_{2-6}$alkenyl group, or an optionally substituted $C_{2-6}$alkynyl group, (wherein each group is optionally substituted with one to three substituents independently selected from the group consisting of a fluorine atom, a $C_{1-6}$alkoxy group, a $C_{3-6}$cycloalkyl group, and a hydroxyl group),
(3) a $C_{3-10}$alicyclic hydrocarbon group (wherein the group may contain one or more unsaturated bonds and the group is optionally substituted with one to three substituents independently selected from the group consisting of a fluorine atom, a $C_{1-6}$alkyl group, a $C_{1-6}$alkoxy group, a $C_{3-6}$cycloalkyl group, and a hydroxyl group),
(4) a 3 to 8-membered saturated heterocyclic group (wherein the group may contain one or more unsaturated bonds and the group is optionally substituted with one to four groups independently selected from the group consisting of
(a) a halogen atom,
(b) a $C_{1-6}$alkyl group (wherein the group is optionally substituted with one to three fluorine atoms),
(c) a $C_{1-6}$alkoxy group (wherein the group is optionally substituted with one to three fluorine atoms), and
(d) an amino group (wherein the group is optionally substituted with one or two $C_{1-6}$alkyl groups),
with the proviso that in the 3 to 8-membered saturated heterocyclic group, a carbon atom on its ring is bonded with the nitrogen atom to which $R^1$ and $R^2$ are attached),
(5) a $C_{6-10}$aryl group (wherein the group is optionally substituted with one to four groups independently selected from the group consisting of
(a) a halogen atom,
(b) a $C_{1-6}$alkyl group (wherein the group is optionally substituted with one to three fluorine atoms),
(c) a $C_{1-6}$alkoxy group (wherein the group is optionally substituted with one to three fluorine atoms), and
(d) an amino group (wherein the group is optionally substituted with one or two $C_{1-6}$alkyl groups)), or
(6) a 5 to 12-membered monocyclic or polycyclic heteroaryl group (wherein the group is optionally substituted with one to four groups independently selected from the group consisting of
(a) a halogen atom,
(b) a $C_{1-6}$alkyl group (wherein the group is optionally substituted with one to three fluorine atoms),
(c) a $C_{1-6}$alkoxy group (wherein the group is optionally substituted with one to three fluorine atoms), and
(d) an amino group (wherein the group is optionally substituted with one or two $C_{1-6}$alkyl groups),
with the proviso that in the 5 to 12-membered monocyclic or polycyclic heteroaryl group, a carbon atom on its ring is bonded with the nitrogen atom to which $R^1$ and $R^2$ are attached); or $R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a fluorine atom, a $C_{1-6}$alkyl group, a $C_{1-6}$alkoxy group, and a hydroxyl group).

In some embodiments, $R^1$ and $R^2$ are each independently
(1) a hydrogen atom,
(2) a $C_{1-6}$alkyl group (wherein the group is optionally substituted with one to three substituents independently selected from the group consisting of a fluorine atom and a $C_{1-6}$alkoxy group),
(3) a $C_{3-10}$alicyclic hydrocarbon group (wherein the group may contain one or more unsaturated bonds and the group is optionally substituted with one to three substituents independently selected from the group consisting of a fluorine atom, a $C_{1-6}$alkyl group, and a $C_{1-6}$alkoxy group),
(4) a 3 to 8-membered saturated heterocyclic group (wherein the group may contain one or more unsaturated bonds and the group is optionally substituted with one to four groups independently selected from the group consisting of
(a) a fluorine atom,
(b) a $C_{1-6}$alkyl group (wherein the group is optionally substituted with one to three fluorine atoms), (c) a $C_{1-6}$alkoxy group (wherein the group is optionally substituted with one to three fluorine atoms), and
(d) an amino group (wherein the group is optionally substituted with one or two $C_{1-6}$alkyl groups),
with the proviso that in the 3 to 8-membered saturated heterocyclic group, a carbon atom on its ring is bonded with the nitrogen atom to which $R^1$ and $R^2$ are attached),
(5) a $C_{6-10}$aryl group (wherein the group is optionally substituted with one to four groups independently selected from the group consisting of
(a) a fluorine atom,
(b) a chlorine atom,
(c) a $C_{1-6}$alkyl group (wherein the group is optionally substituted with one to three fluorine atoms),
(d) a $C_{1-6}$alkoxy group (wherein the group is optionally substituted with one to three fluorine atoms), and
(e) an amino group (wherein the group is optionally substituted with one or two $C_{1-6}$alkyl groups)), or
(6) a 5 to 12-membered monocyclic or polycyclic heteroaryl group (wherein the group is optionally substituted with one to four groups independently selected from the group consisting of
(a) a fluorine atom,
(b) a chlorine atom,
(c) a $C_{1-6}$alkyl group (wherein the group is optionally substituted with one to three fluorine atoms),
(d) a $C_{1-6}$alkoxy group (wherein the group is optionally substituted with one to three fluorine atoms), and
(e) an amino group (wherein the group is optionally substituted with one or two $C_{1-6}$alkyl groups),
with the proviso that in the 5 to 12-membered monocyclic or polycyclic heteroaryl group, a carbon atom on its ring is bonded with the nitrogen atom to which $R^1$ and $R^2$ are attached); or $R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a fluorine atom, a $C_{1-6}$alkyl group, a $C_{1-6}$alkoxy group, and a hydroxyl group).
In some embodiments, $R^1$ and $R^2$ are each independently
(1) a hydrogen atom,
(2) a $C_{1-6}$alkyl group (wherein the group is optionally substituted with one to three substituents independently selected from the group consisting of a fluorine atom and a $C_{1-6}$alkoxy group),
(3) a $C_{3-10}$alicyclic hydrocarbon group (wherein the group may contain one or more unsaturated bonds and the group is optionally substituted with one to three substituents independently selected from the group consisting of a fluorine atom and a $C_{1-6}$alkoxy group); or
$R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a fluorine atom, a $C_{1-6}$alkyl group, a $C_{1-6}$alkoxy group, and a hydroxyl group).
In some embodiments, $R^1$ and $R^2$ are each independently
(1) a hydrogen atom,
(2) a $C_{1-6}$alkyl group, or
(3) a $C_{3-10}$alicyclic hydrocarbon group (wherein the group may contain one or more unsaturated bonds), or $R^1$ and $R^2$ are taken together with the nitrogen atom to which they are attached to form a 3 to 8-membered, nitrogen-containing heterocycle (wherein the heterocycle may contain one or more unsaturated bonds).
In some embodiments, $R^3$ is
(1) a $C_{6-10}$aryl group (wherein the group is optionally substituted with one to seven substituents independently selected from the group consisting of
(a) a halogen atom,
(b) a hydroxyl group,
(c) a cyano group,
(d) a $C_{1-6}$alkylsulfonyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a fluorine atom, a $C_{1-6}$alkoxy group, a $C_{3-6}$cycloalkyl group, and a hydroxyl group),
(f) a $C_{1-6}$alkylcarbonyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a fluorine atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a fluorine atom, a $C_{1-6}$alkoxy group, a $C_{3-6}$cycloalkyl group, and a hydroxyl group),
(j) —N($R^4$)CO$R^5$,
(k) —CON$R^6R^7$,
(l) —S(O)$_2$N$R^8R^9$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or
two or more substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or
(2) a 5 to 12-membered monocyclic or polycyclic heteroaryl group (wherein the group is optionally substituted with one to nine substituents independently selected from the group consisting of
(a) a halogen atom,
(b) a hydroxyl group,
(c) a cyano group,
(d) a $C_{1-6}$alkylsulfonyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a fluorine atom, a $C_{1-6}$alkoxy group, a $C_{3-6}$cycloalkyl group, and a hydroxyl group),
(f) a $C_{1-6}$alkylcarbonyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a fluorine atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a fluorine atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a fluorine atom, a $C_{1-6}$alkoxy group, a $C_{3-6}$cycloalkyl group, and a hydroxyl group),
(j) a $C_{6-10}$aryl group (wherein the group is optionally substituted with one to three substituents independently selected from the group consisting of a fluorine atom, a $C_{1-6}$alkoxy group, a $C_{3-6}$cycloalkyl group, and a hydroxyl group),
(k) —N($R^{10}$)COR$^{11}$,
(l) —CONR$^{12}$R$^{13}$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or
two or more substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups),
with the proviso that in the 5 to 12-membered monocyclic or polycyclic heteroaryl group, a carbon atom on its ring is bonded with the carbon atom to which $R^3$ is attached); and
$R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$, and $R^{12}$ and $R^{13}$ each independently may be taken together to form a 4 to 10-membered nitrogen-containing heterocycle.

In some embodiments, $R^3$ is
(1) a $C_{6-10}$aryl group (wherein the group is optionally substituted with one to seven substituents independently selected from the group consisting of
(a) a fluorine atom,
(b) a chlorine atom,
(c) a cyano group,
(d) a $C_{1-6}$alkylaminosulfonyl group (wherein each $C_{1-6}$alkyl group is optionally substituted with one to three substituents independently selected from the group consisting of a fluorine atom, a $C_{1-6}$alkoxy group, and a hydroxyl group),
(e) a $C_{1-6}$alkyl group (wherein the group is optionally substituted with one to three substituents independently selected from the group consisting of a fluorine atom, a $C_{1-6}$alkoxy group, and a hydroxyl group),
(f) a $C_{1-6}$alkoxy group (wherein the group is optionally substituted with one to three substituents independently selected from the group consisting of a fluorine atom, a $C_{1-6}$alkoxy group, and a hydroxyl group),
(g) a $C_{3-10}$cycloalkoxy group (wherein the group is optionally substituted with one to three substituents independently selected from the group consisting of a fluorine atom, a $C_{1-6}$alkoxy group, and a hydroxyl group),
(h) —N($R^4$)COR$^5$,
(i) —CONR$^6$R$^7$,
(j) —S(O)$_2$NR$^8$R$^9$,
(k) an amino group (wherein the group is optionally substituted with one or two $C_{1-6}$alkyl groups), and
(l) a 4 to 7-membered cyclic amino group (wherein the group is optionally substituted with one or two $C_{1-6}$alkyl groups), or
two substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or
(2) a 5 to 12-membered monocyclic or polycyclic heteroaryl group (wherein the group is optionally substituted with one to nine substituents independently selected from the group consisting of
(a) a fluorine atom,
(b) a chlorine atom,
(c) a cyano group,
(d) a $C_{1-6}$alkylaminosulfonyl group (wherein each $C_{1-6}$alkyl group is optionally substituted with one to three substituents independently selected from the group consisting of a fluorine atom, a $C_{1-6}$alkoxy group, and a hydroxyl group),
(e) a $C_{1-6}$alkyl group (wherein the group is optionally substituted with one to three substituents independently selected from the group consisting of a fluorine atom, a $C_{1-6}$alkoxy group, and a hydroxyl group),
(f) a $C_{1-6}$alkoxy group (wherein the group is optionally substituted with one to three substituents independently selected from the group consisting of a fluorine atom, a $C_{1-6}$alkoxy group, and a hydroxyl group),
(g) a $C_{3-10}$cycloalkoxy group (wherein the group is optionally substituted with one to three substituents independently selected from the group consisting of a fluorine atom, a $C_{1-6}$alkoxy group, and a hydroxyl group),
(h) a $C_{6-10}$aryl group (wherein the group is optionally substituted with one to three substituents independently selected from the group consisting of a fluorine atom, a $C_{1-6}$alkoxy group, and a hydroxyl group),
(i) —N($R^8$)COR$^9$,
(j) —CONR$^{10}$R$^{11}$,
(k) an amino group (wherein the group is optionally substituted with one or two $C_{1-6}$alkyl groups), and (l) a 4 to 7-membered cyclic amino group (wherein the group is optionally substituted with one or two $C_{1-6}$alkyl groups), or two substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R9$ and $R^{12}$ and $R^{13}$ each independently may be taken together to form a 4 to 10-membered nitrogen-containing heterocycle.

In some embodiments, $R^3$ is (1) a $C_{6-10}$aryl group (wherein the group is optionally substituted with one to seven substituents independently selected from the group consisting of
(a) a fluorine atom,
(b) a chlorine atom,
(c) a cyano group,
(d) a $C_{1-6}$alkylaminosulfonyl group (wherein each $C_{1-6}$alkyl group is optionally substituted with one to three fluorine atoms),
(e) a $C_{1-6}$alkyl group (wherein the group is optionally substituted with one to three fluorine atoms),
(f) a $C_{1-6}$alkoxy group (wherein the group is optionally substituted with one to three fluorine atoms),
(g) —N($R^4$)COR$^5$,
(h) —CONR$^6$R$^7$,
(i) —S(O)$_2$NR$^8$R$^9$,
(j) an amino group (wherein the group is optionally substituted with one or two $C_{1-6}$alkyl groups), and
(k) a 4 to 7-membered cyclic amino group (wherein the group is optionally substituted with one or two $C_{1-6}$alkyl groups), or
two substituents on the $C_{6-10}$aryl group may be joined to form a 5 to 8-membered non-aromatic carbocyclic or heterocyclic ring (wherein the 9 to 16-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups)), or
(2) a 5 to 12-membered monocyclic or polycyclic heteroaryl group (wherein the group is optionally substituted with one to nine substituents independently selected from the group consisting of
(a) a fluorine atom,
(b) a chlorine atom,
(c) a cyano group,
(d) a $C_{1-6}$alkylaminosulfonyl group (wherein each $C_{1-6}$alkyl group is optionally substituted with one to three fluorine atoms),
(e) a $C_{1-6}$alkyl group (wherein the group is optionally substituted with one to three fluorine atoms),
(f) a $C_{1-6}$alkoxy group (wherein the group is optionally substituted with one to three fluorine atoms),
(g) a $C_{6-10}$aryl group,
(h) —N($R^{10}$)COR$^{11}$,
(i) —CONR$^{12}$R$^{13}$,
(j) an amino group (wherein the group is optionally substituted with one or two $C_{1-6}$alkyl groups), and
(k) a 4 to 7-membered cyclic amino group (wherein the group is optionally substituted with one or two $C_{1-6}$alkyl groups), or
two substituents on the 5 to 12-membered monocyclic or polycyclic heteroaryl group may be joined to form a 5 to 8-membered non-aromatic carbocyclic or heterocyclic ring (wherein the 8 to 18-membered ring is optionally substituted with one or two $C_{1-6}$alkyl groups; or in some embodiments, the 5 to 8-membered non-aromatic carbocyclic or heterocyclic ring is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$, and $R^{12}$ and $R^{13}$ each independently may be taken together to form a 4 to 10-membered nitrogen-containing heterocycle.

In some embodiments, $R^3$ is (1) a $C_{6-10}$aryl group (wherein the group is optionally substituted with one to seven substituents independently selected from the group consisting of
(a) a fluorine atom,
(b) a chlorine atom,
(c) a cyano group,
(d) a $C_{1-6}$alkyl group (wherein the group is optionally substituted with one to three fluorine atoms),
(e) a $C_{1-6}$alkoxy group (wherein the group is optionally substituted with one to three fluorine atoms),
(f) —N($R^4$)COR$^5$,
(g) —CONR$^6$R$^7$,
(h) —S(O)$_2$NR$^8$R$^9$,
(i) an amino group (wherein the group is optionally substituted with one or two $C_{1-6}$alkyl groups), and
(j) a 4 to 7-membered cyclic amino group (wherein the group is optionally substituted with one or two $C_{1-6}$alkyl groups), or
two substituents on the $C_{6-10}$aryl group may be joined to form a 5 to 8-membered non-aromatic heterocycle (wherein the 5 to 8-membered non-aromatic heterocycle is optionally substituted with one or two $C_{1-6}$alkyl groups)), or
(2) a 5 to 12-membered monocyclic or polycyclic heteroaryl group (wherein the group is optionally substituted with one to nine substituents independently selected from the group consisting of
(a) a fluorine atom,
(b) a chlorine atom,
(c) a cyano group,
(d) a $C_{1-6}$alkyl group (wherein the group is optionally substituted with one to three fluorine atoms),
(e) a $C_{1-6}$alkoxy group (wherein the group is optionally substituted with one to three fluorine atoms),
(f) a $C_{6-10}$aryl group,
(g) —N($R^{10}$)COR$^{11}$,
(h) —CONR$^{12}$R$^{13}$,
(i) an amino group (wherein the group is optionally substituted with one or two $C_{1-6}$alkyl groups), and
(j) a 4 to 7-membered cyclic amino group (wherein the group is optionally substituted with one or two $C_{1-6}$alkyl groups), or two substituents on the 5 to 12-membered monocyclic or polycyclic heteroaryl group may be joined to form a 5 to 8-membered non-aromatic heterocycle (wherein the 5 to 8-membered non-aromatic heterocycle is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$, and $R^{12}$ and $R^{13}$ each independently may be taken together to form a 4 to 10-membered nitrogen-containing heterocycle.

The number of substituent(s) in $R^1$ and $R^2$ includes, without limitation, 1 to 4, 1 to 3, 1 to 2, 1, and the like; and, in $R^3$ includes, without limitation, 1 to 9, 1 to 8, 1 to 7, 1 to 6, 1 to 5, 1 to 4, 1 to 3, 1 to 2, 1, and the like.

In certain embodiments, methods of producing compounds of the present disclosure are illustrated by the following examples. However, the scope of the present disclosure is certainly not limited thereto. The following reactions are merely illustrations. The compounds of the present disclosure can be produced by appropriately combining known raw material compounds and conventional methods or production methods in accordance therewith based on knowledge of those skilled in the art of synthetic organic chemistry. If a raw material compound to be used is commercially available, such a commercially available compound also can be used.

In certain embodiments, a compound represented by formula (1) of the present disclosure is produced, for example, by the following production methods. It should be noted that a compound used in the following production methods may form a salt thereof as long as it does not interfere with a reaction.

Production Methods

In certain embodiments, compounds represented by formula (1) or salts thereof are produced, for example, by methods described below.

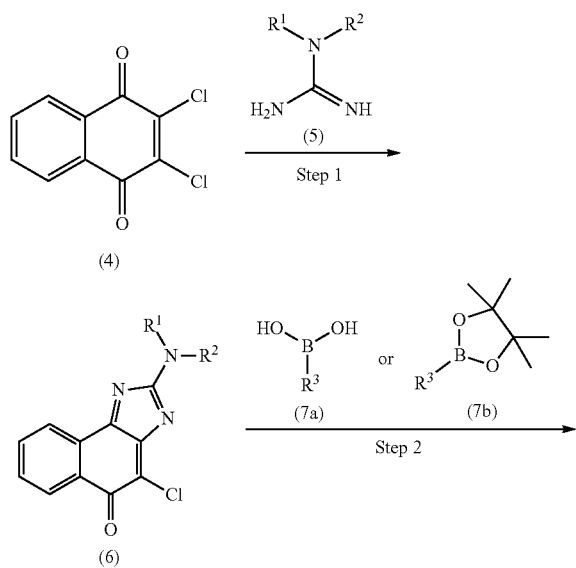

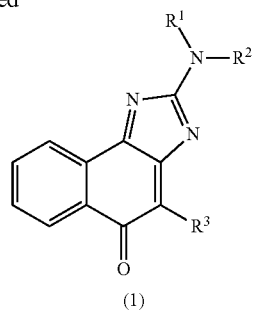

(1)

In one embodiment, Compound (4), a commercially available product or a substance produced according to a known synthesis method can be used. Compound (5), a commercially available product or a substance produced according to a known synthesis method (for example, International Publication No. 2005/070934 pamphlet) can be used. Compound (7a) and Compound (7b), commercially available products or substances produced according to a known synthesis method can be used. It should be noted that $R^1$, $R^2$, and $R^3$ in Compounds (5), (7a), and (7b) indicate groups as defined above.

Step 1: Production step of Compound (6)

Compound (6) is produced by treating Compound (4) with Compound (5). Specifically, treating Compound (4) with Compound (5) in the presence of a base to obtain Compound (6). The base is selected from bases and the like illustrated below. In one embodiment, the base is potassium carbonate. A solvent used in the synthesis of Compound (6) is selected from solvents and the like illustrated below. In one embodiment, the solvent is acetonitrile. In one embodiment, the temperature of this reaction is 0 to 150° C. In one embodiment, the time for this reaction is within a range of 0.5 to 24 hours.

Step 2: Production step of Compound (1)

Compound (1) is produced by treating Compound (6) with Compound (7a) or (7b). Specifically, coupling Compound (6) in the presence of a catalyst and a base with Compound (7a) or (7b) provides Compound (1). Examples of the catalyst include transition metals, such as palladium and the like, salts thereof, complexes thereof, and those provided on a solid support, such as polymers and the like. Bases used in the present step are selected from bases and the like illustrated below. In one embodiment the base includes potassium carbonate. In another embodiment, the base includes sodium carbonate. A solvent used in the present step is selected from solvents and the like illustrated below. In one embodiment, the solvent includes a mixed solvent of 1,2-dimethoxyethane and water. In one embodiment, the temperature of the reaction is 0 to 150° C. In another embodiment, the time for the reaction is within a range of 0.5 to 24 hours.

Bases used in the above steps 1 and 2 should be appropriately selected depending on the types of reactions and raw material compounds, and the like. Suitable bases include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium t-butoxide; organic metal bases such as butyl lithium and lithium diisopropylamide; and organic bases such as triethylamine, diisopropylethylamine, pyridine, 4-dimethylaminopyridine (DMAP), and 1,8-diazabicyclo[5.4.0]-7-undecene (DBU).

Solvents used in the above steps 1 and 2 should be appropriately selected depending on the types of reactions and raw material compounds, and the like. Suitable solvents include alcohols such as methanol, ethanol, and isopropanol; ketones such as acetone and ethyl methyl ketone; halogenated hydrocarbons such as methylene chloride and chloroform; ethers such as tetrahydrofuran (THF), dioxane, and 1,2-dimethoxyethane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethyl sulfoxide (DMSO); and nitriles such as acetonitrile. These solvents can be used alone or as a mixture of two or more thereof. In addition, depending on the type of reaction, organic bases may be used as solvent.

The compounds of the present disclosure represented by formulae (1), (2), or (3), or an intermediate thereof, can be separated and purified by known methods to those skilled in the art. Suitable purification methods include extraction, reprecipitation or trituration, column chromatography (e.g., silica gel column chromatography, ion exchange column chromatography, preparative liquid chromatography, and the like), recrystallization, and the like. The following can be used as recrystallization solvents: alcohol-based solvents such as methanol, ethanol, 2-propanol, and the like; ether-based solvents such as diethyl ether and the like; ester-based solvents such as ethyl acetate and the like; aromatic-hydrocarbon-based solvents such as benzene, toluene, and the like; ketone-based solvents such as acetone and the like; halogen-based solvents such as dichloromethane, chloroform, and the like; hydrocarbon-based solvents such as hexane and the like; polar aprotic solvents such as dimethylformamide, acetonitrile, and the like; polar protic solvents such as water; or mixed solvents of two or more selected from the above solvents. Other purification methods can be used, such as methods described in *Jikken Kagaku Koza* (The Chemical Society of Japan ed., Maruzen), vol. 1, or the like.

In the compounds of the present disclosure represented by formulae (1), (2), or (3), or pharmaceutically acceptable salts thereof, asymmetry may occur, or compounds of formulae (1), (2), or (3) may have an asymmetric carbon or a substituent having an asymmetric carbon. In such compounds, optical isomers, atropisomers, enantiomers, or diastereomers might be present. The compounds of the present disclosure also encompass mixtures of these atropisomers, enantiomers, or diastereomers, as well as isolated individual isomers. Compounds with an enantiomeric, diastereomeric, or atropisomeric excess can be produced according to a general production method. In some embodiments, asymmetric synthesis might employ starting materials having asymmetry (e.g., menthol, sugars, and amino acids), methods wherein asymmetry is introduced within a reaction sequence, methods employing optical resolution, or the like, at a suitable stage of a production step, and the like. Examples of optical resolution methods include diastereomeric salt formation, wherein the compound represented by formulae (1), (2), or (3) or intermediates therefor has a basic functional group, and in nonreactive solvent (e.g., alcohol-based solvent such as methanol, ethanol, 2-propanol, and the like; ether-based solvent such as diethyl ether and the like; ester-based solvent such as ethyl acetate and the like; hydrocarbon-based solvent such as aliphatic-hydrocarbon-based solvent such as hexane and the like; or aromatic-hydrocarbon-based solvent such as toluene and the like; aprotic solvent such as acetonitrile and the like; or mixed solvent of two or more selected from the above solvents) using an optically active acid (e.g., a monocarboxylic acid such as mandelic acid, N-benzyloxy-alanine, lactic acid, and the like, a dicarboxylic acid such as tartaric acid, o-diisopropylidene tartaric acid, malic acid, and the like, and a sulfonic acid such as camphor sulfonic acid, bromocamphor sulfonic acid, and the like) forms a diastereomeric salt. When an intermediate for the compound of the present disclosure represented by formulae (1), (2), or (3) has an acidic functional group such as a carboxylic acid group and the like, optical resolution also can be performed by diastereomeric salt formation using an optically active amine (e.g., organic amines such as 1-phenylethylamine, quinine, quinidine, cinchonidine, cinchonine, strychnine, and the like).

In certain embodiments, a temperature to form a diastereomeric salts as described aboce is selected from the range from −50° C. to the boiling point of solvent, the range from 0° C. to the boiling point, and the range from room temperature to the boiling point of solvent. In certain embodiments, to improve the optical purity, it may be desirable to increase a temperature to the vicinity of the boiling point of a solvent once. In certain embodiments thereafter, when a precipitated salt is collected by filtration, as necessary, the temperature can be cooled to improve the yield. Regarding the amount of an optically active acid or amine used, in certain embodiments the range from about 0.5 to about 2.0 equivalents, and the range of approximately 1 equivalent, relative to a substrate is suitable. As necessary, recrystallization can be performed in a nonreactive solvent (e.g., alcohol-based solvent such as methanol, ethanol, 2-propanol, and the like; ether-based solvent such as diethyl ether and the like; ester-based solvent such as ethyl acetate and the like; hydrocarbon-based solvent such as toluene and the like; aprotic solvent such as acetonitrile and the like; or mixed solvent of two or more selected from the above solvents) to obtain an optically active or enriched salt in high purity. In addition, in certain embodiments, a salt that is optically resolved as necessary can be treated with an acid or a base by a general method to obtain corresponding free form.

Compounds represented by formula (1) are readily reduced and converted to a compound represented by formula (2) or (3). For example, in an LC-MS measurement described in the Examples below, when Solution A containing formic acid is used as solvent, the existence of a compound of formula (2) or (3), which is a reduced form of a compound of formula (1), can be confirmed. These reduced form compounds of formulae (2) and (3) are also believed to exhibit an effect to suppress cell death due to oxidative stress, similar to compounds of formula (1). Therefore, the compounds of the present disclosure encompass, in addition to a compound of formula (1), compounds of formulae (2) and (3), which are reduced forms thereof.

Among the starting materials and intermediates in respective production methods described above, those not amenable to the production methods described above are commercially available compounds or can be synthesized from a commercially available compound and a known method to those skilled in the art or a method in accordance therewith.

In certain embodiments, the compounds of the present disclosure and pharmaceutically acceptable salts thereof are useful as novel therapeutic and/or prophylactic agents for a disease caused by or aggravated by oxidative stress or mitochondrial dysfunction (e.g., amyotrophic lateral sclerosis (ALS), Huntington disease, Parkinson disease, Friedreich ataxia (FRDA), Alzheimer disease, multiple system atrophy (MS), Creutzfeldt-Jakob disease, Machado-Joseph disease, spinocerebellar ataxia, atherosclerosis, myocardial infarction, cerebral infarction, diseases related to aging, diabetes, alcoholic liver injury, non-alcoholic steatohepatitis (NASH), pulmonary fibrosis, hearing loss, spinal muscular atrophy (SMA), chronic obstructive pulmonary disease, Leber's hereditary optic neuropathy (LHON), mitochondrial myopathy, encephalopathy, lactic acidosis, and stroke-like episodes (MELAS), Leigh Syndrome and Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), or Pearson's disease (pancytopenia, multiple organ dysfunction syndrome)). In some embodiments, they are useful against amyotrophic lateral sclerosis (ALS), Huntington disease, Parkinson disease, and Alzheimer disease (see, e.g., the references cited in the BACKGROUND section herein; G. Nagesh Babu, Neurochemistry International (2008), 52: 1284-1289; Matthias L. Jauslin (2002) Human Molecular Genetics, 11(24): 3055-3063; Luis H. Barbeito (2004) Brain Research Reviews, 47: 263-274; Siân C. Barber (2006) Biochimica et Biophysica Acta, 1762: 1051-1067). It should be noted that in the present disclosure, "prevention (preventing)" or "prophylaxis" is an action to administer an active ingredient of the present disclosure to a healthy person that does not show symptoms of a disease, where in certain embodiments the purpose thereof is, for example, to prevent the onset of a disease. It should be noted that in the present disclosure, "Treatment (treating)" is an action to administer an active ingredient of the present disclosure to a person (e.g., a patient) diagnosed as having a disease by a medical doctor.

In certain embodiments, the compounds of the present disclosure and pharmaceutically acceptable salts thereof can be used in combination with a brain protection drug (free radical scavenger), such as edaravone, for a purpose of enhancing effects. In addition, compounds described herein also can be used in combination with a pharmaceutical agent, such as an anticancer agent, a therapeutic drug for amyotrophic lateral sclerosis, a therapeutic drug for Creutzfeldt-Jakob disease, a therapeutic drug for Machado-Joseph disease, a therapeutic drug for spinocerebellar ataxia, a therapeutic drug for multiple system atrophy (MS), a therapeutic drug for spinal muscular atrophy (SMA), a therapeutic drug for Huntington disease, a therapeutic drug for Parkinson disease, a therapeutic drug for Friedreich ataxia (FRDA), a therapeutic drug for Alzheimer disease, a therapeutic drug for atherosclerosis, a therapeutic drug for myocardial infarction, a therapeutic drug for cerebral infarction, a therapeutic drug for senile cognition disorder, a therapeutic drug for disease related to aging, a therapeutic drug for diabetes, a therapeutic drug for alcoholic liver injury, a therapeutic drug for non-alcoholic steatohepatitis (NASH), a therapeutic drug for chronic obstructive pulmonary disease, a therapeutic drug for pulmonary fibrosis, a therapeutic drug for hearing loss, a therapeutic drug for Leber's hereditary optic neuropathy (LHON), a therapeutic drug for mitochondrial myopathy, encephalopathy, lactic acidosis, and stroke-like episodes (MELAS), a therapeutic drug for Leigh Syndrome, a therapeutic drug for Kearns-Sayre syndrome (KSS), a therapeutic drug for chronic progressive external ophthalmoplegia (CPEO), a therapeutic drug for myoclonic epilepsy with ragged-red fibers (Fukuhara disease, MERRF, myoclonic epilepsy, myoclonic epilepsy syndrome), a therapeutic drug for Pearson's disease (pancytopenia, multiple organ dysfunction syndrome), and the like. In addition, for a purpose of suppressing pharmaceutical agent side effects, compounds described herein can be used in combination with a pharmaceutical agent such as an antiemetic, a sleep-inducing drug, an anticonvulsant, a vasopressor, an anticoagulant agent, and the like.

The usefulness as a pharmaceutical product of the compounds of the present disclosure is verified by a pharmacological test that can confirm a pharmacological effect, a pharmacokinetic test that can confirm in vivo kinetics, and a safety test that can confirm safety, or the like. For example, the pharmaceutical product is verified by tests as described below. These tests can be generally carried out with mice, rats, dogs, monkeys, and the like. In addition, tests can be carried out while conscious or under anesthesia as necessary.

These tests are without limitation as long as they can confirm physiological activity and safety. For example, physiological activity and safety may be verified by the following tests.

Examples of the pharmacological test include a cell death suppression test that induces various oxidative stresses using a nerve cell or a fibroblast, and the like. Specific examples thereof include, without limitation, a cell viability evaluation test using human dermal fibroblasts derived from Friedreich ataxia patients, a cell viability evaluation test using human dermal fibroblasts derived from ALS patients where oxidative stress induced cell death is induced with nitric oxide (NO), an ALS animal model test, each of which are described in test examples, and the like.

Examples of the pharmacokinetic test include, without limitation, a blood concentration evaluation test, a brain transferability evaluation test, a P-glycoprotein substrate recognition test, a drug interaction test, a drug metabolism pathway identification test, a dansyl glutathione addition test, a cyano addition test, and the like. Examples of a preferable compound include a compound exhibiting high intracerebral transferability.

Examples of the safety test include a measurement test of blood pressure and heart rate, an electrocardiogram measurement test, general symptom observations, a general toxicity test, and the like, in addition to in vitro tests such as a hERG inhibition test, a cytotoxicity test, the Ames test, and the like.

After a pharmaceutical product compound is taken into a living body, its chemical structure may be changed by undergoing metabolism where a highly reactive intermediate, i.e., a reactive metabolite may be produced that expresses toxicity (e.g., hepatotoxicity, allergy, necrosis of tissue, mutagenicity, carcinogenicity, and the like). Certain compounds disclosed herein were tested for stability (CLint intrinsic clearance) in a cyanide trapping assay, and were found to be stable. In general, compounds with higher CLint values may have higher risks of hepatotoxicity. Since the tested compounds were stable in the cyanide trapping assay, they may be less likely to form protein adducts that could be hepatotoxic, and thus may have improved safety risk over longer periods The compounds of the present invention can be directly administered or formulated using a suitable dosage form for oral administration or parenteral administration. Examples of the dosage form include, but are not limited to, a tablet, a capsule, powder, granules, a solution, a suspension, an injection, a patch, a poultice, and the like. A formulation is produced by a known method using a pharmaceutically acceptable additive.

The following can be used as an additive, including pharmaceutically acceptable additives, such as, without limitation, an excipient, disintegrator, binder, fluidizer, lubricant, coating agent, solvent, solubilizing agent, thickener, dispersing agent, stabilizing agent, sweetener, flavoring agent, and the like. In certain embodiments, pharmaceutically acceptable additives include lactose, mannitol, crystalline cellulose, hydroxypropyl cellulose having low substitution degree, corn starch, partially pregelatinized starch, carmellose calcium, croscarmellose sodium, hydroxypropyl cellulose, hydroxypropylmethyl cellulose, polyvinyl alcohol, magnesium stearate, sodium stearyl fumarate, polyethylene glycol, propylene glycol, titanium oxide, talc, and the like.

In some embodiments is the use of a compound of the present disclosure or a reduced form thereof or a pharmaceutically acceptable salt thereof or the use of a pharmaceutical composition of the present disclosure for the manufacture of a medicament for treating and/or preventing a disease caused by or aggravated by oxidative stress or mitochondrial dysfunction.

Suitable administration routes for the compounds of the present disclosure include, without limitation, oral, parenteral, topical, ocular, or rectal administration. In certain embodiments, the daily dose thereof varies according to the type of compound, administration method, the condition/age of a patient, and the like. For example, in the case of oral administration, in certain embodiments, about 0.01 to 1000 mg, or about 0.1 to 500 mg, can be administered per kg of body weight of a human or mammal ranging from one to several times. In the case of parenteral administration such as intravenous injection and the like, in certain embodiments, for example, about 0.01 mg to 300 mg, or about 1 mg to 100 mg can be administered per kg of body weight of a human or mammal.

The period of administration of the compound of the present disclosure in combination with a pharmaceutical agent is not limited, and these may be administered to a subject concurrently or at intervals. In addition, mixtures of the compound of the present disclosure in combination with a pharmaceutical agent may be made. The dosage of a combination pharmaceutical agent can be appropriately selected using clinically appropriate dosages. In addition, the mixing ratio of the compound of the present disclosure and a combination pharmaceutical agent can be appropriately selected depending on a subject to be administered, an administration route, target disease, symptoms, combinations, and the like. For example, in one embodiments, when a subject to be administered is a human, 0.1 to 1000 parts by weight of a combination pharmaceutical agent may be used relative to one part by weight of the compound of the present disclosure.

EXAMPLES

Hereinafter, the compounds of the disclosure are more specifically described with reference examples, Examples, and test examples. However, the scope of the present disclosure is certainly not limited to these examples. It should be noted that compound names shown in the following reference examples and Examples do not always follow the IUPAC nomenclature.

The following abbreviations are sometimes used throughout the present specification to simplify a description.
Me: methyl
tert: tertiary
Boc: tert-butoxycarbonyl
s: singlet
brs: broad singlet
d: doublet
t: triplet
q: quartet
dd: doubled doublet
m: multiplet
J: coupling constant
Hz: Hertz
THF: tetrahydrofuran
TFA: trifluoroacetic acid
$CDCl_3$: deuterated chloroform
Acetone-$d_6$: deuterated acetone For silica gel column chromatography and amino silica gel column chromatography used in reference examples and Examples, a silica gel column and an amino silica gel column produced by Yamazen Corporation were used. Measurement by LC-MS was carried out using various conditions shown below in Table 1. A retention time (R.T.) represents a time when a mass spectrum peak appeared in LC-MS measurements.

TABLE 1

| Analysis condition | |
|---|---|
| Analyzer | Waters ACQUITY UPLC (Registered trademark) equipment |
| Column | ACQUITY UPLC (Registered trademark) BEH C18 Column, 130 Å, 1.7 µm, 2.1 mm X 150 mm |
| Solvent | Solution A: 0.05% formic acid in $H_2O$ Solution B: acetonitrile |
| Gradient condition | 0.0 min to 1.3 min; A/B 90:10~1:99 1.3 min to 1.5 min; A/B 1:99 1.5 min to 2.0 min; A/B 90:10 |
| Flow rate | 0.75 mL/min |
| Wavelength (UV) | 220 nm, 254 nm |
| Column temperature | 40° C. |

Unless otherwise specified, for raw material compounds, reaction reagents, and solvents, those commercially available were used.

Reference Example 1

4-Chloro-2-(dimethylamino)-5H-naphth[1,2-d]imidazol-5-one

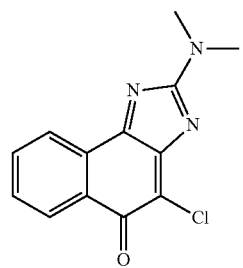 [SMILES: CN(C)C1=NC2=C(Cl)C(=O)c3ccccc3C2=N1]

2,3-Dichloro-1,4-naphthoquinone (50 g), 1,1-dimethylguanidine sulfate salt (30 g), and potassium carbonate (46 g) were dissolved in acetonitrile (500 mL) and then the reaction mixture was heated at reflux for 4 hours. The reaction solution was cooled to room temperature, and then chloroform was added thereto and the reaction solution was filtered. The resulting filtrate was concentrated under reduced pressure, and then chloroform and water were added to the residue and the target substance was extracted into the organic layer. The resulting organic layer was washed with saturated brine and then dried over anhydrous sodium sulfate. The organic layer was then concentrated under reduced pressure. Ethyl acetate was added to the residue and the target substance was recrystallized to yield Reference example 1 (32 g). $^1$H-NMR (CDCl$_3$) δ: 8.12 (1H, dd, J=7.3, 1.8 Hz), 8.05 (1H, dd, J=7.6, 1.6 Hz), 7.64-7.55 (2H, m), 3.60 (3H, s), 3.50 (3H, s).

LC-MS: R.T. 0.82, 260.6 (M+1)

Reference Examples 2 to 6

According to a similar method to Reference example 1, compounds of Reference examples 2 to 6 shown in the following table were obtained using corresponding raw materials.

TABLE 2

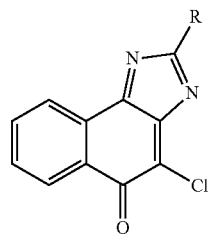

| Reference example | R | NMR, LCMS |
|---|---|---|
| 2 | ![ethyl-N-ethyl] | $^1$H-NMR (CDCl$_3$) δ: 8.13-8.10 (1H, m), 8.06-8.04 (1H, m), 7.63-7.54 (2H, m), 3.99 (2H, q, J = 7.3 Hz), 3.91 (2H, q, J = 7.3 Hz), 1.40 (3H, t, J = 7.3 Hz), 1.37 (3H, t, J = 7.3 Hz). R.T. 1.04 min, m/z 288 (M + 1). |
| 3 | ![pyrrolidine] | $^1$H-NMR (CDCl$_3$) δ: 8.13-8.10 (1H, m), 8.05-8.03 (1H, m), 7.63-7.54 (2H, m), 4.10-4.07 (2H, m), 3.96-3.94 (2H, m), 2.14-2.06 (4H, m). R.T. 0.86 min, m/z 286 (M + 1) |
| 4 | ![morpholine] | $^1$H-NMR (CDCl$_3$) δ: 8.13 (1H, dd, J = 7.3, 1.8 Hz), 8.03 (1H, dd, J = 7.3, 1.4 Hz), 7.65-7.57 (2H, m), 4.22 (2H, t, J = 4.8 Hz), 4.11 (2H, t, J = 4.8 Hz), 3.891-3.87 (4H, m). R.T. 0.84 min, m/z 302 (M + 1). |
| 5 | ![N-methylpiperazine] | $^1$H-NMR (CDCl$_3$) δ: 8.12 (1H, dd, J = 7.8, 1.4 Hz), 8.03 (1H, dd, J = 7.3, 1.8 Hz), 7.64-7.56 (2H, m), 4.23 (2H, t, J = 5.0 Hz), 4.12 (2H, t, J = 5.0 Hz), 2.63-2.59 (4H, m), 2.38 (3H, s). R.T. 0.51 min, m/z 315 (M + 1) |
| 6 | ![methoxyethyl-methylamino] | $^1$H-NMR (CDCl$_3$) δ: 8.14-8.09 (1.55H, m), 8.06-8.01 (1.55H, m), 7.64-7.54 (3.1H, m), 4.13 (2H, t, J = 5.3 Hz), 4.04 (1.1H, t, J = 5.0 Hz), 3.79 (1.1H, t, J = 5.0 Hz), 3.70 (2H, t, J = 5.3 Hz), 3.67 (1.65H, s), 3.55 (3H, s), 3.39 (1.65H, s), 3.38 (3H, s). R.T. 0.88 min, m/z 305 (M + 1) |

The points of the arrows represent the position of bonding with the main skeleton.

Example 1

2-(Dimethylamino)-4-(4-methoxyphenyl)-5H-naphth[1,2-d]imidazol-5-one

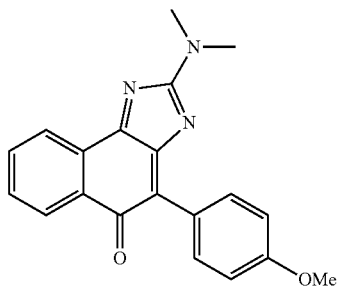 [SMILES: COc1ccc(C2=C3N=C(N(C)C)N=C3c3ccccc3C2=O)cc1]

4-Chloro-2-(dimethylamino)-5H-naphth[1,2-d]imidazol-5-one (2.0 g), 4-methoxyphenylboronic acid (1.7 g), potassium carbonate (3.1 g), and tetrakis(triphenylphosphine)palladium (0) (444 mg) were added to a mixed solution of 1,2-dimethoxyethane (200 mL) and water (40 mL), and the reaction mixture was heated at reflux for 3 hours. The reaction solution was cooled to room temperature and then filtered through Celite. The resulting filtrate was then concentrated under reduced pressure. Chloroform and water were added to the resulting residue, and then the target substance was extracted into the organic layer. The resulting organic layer was washed with saturated brine, and then dried over anhydrous sodium sulfate and concentrated under reduced pressure. The residue was purified by silica gel column chromatography and the resulting solid was washed with methanol to yield the compound of Example 1 (2.1 g). $^1$H-NMR (CDCl$_3$) δ: 8.11 (1H, dd, J=7.3, 1.4 Hz), 8.04 (1H, dd, J=7.1, 1.6 Hz), 7.89 (2H, d, J=9.2 Hz), 7.58-7.56 (2H, m), 6.97 (2H, d, J=9.2 Hz), 3.85 (3H, s), 3.56 (3H, s), 3.43 (3H, s).

LC-MS: R.T. 0.98, 332.6 (M+1)

Examples 2 to 70

In accordance with the method described in Example 1, compounds of Examples 2 to 70 shown in the following table were obtained using the compounds of Reference examples 1 to 6 and corresponding raw materials.

TABLE 3

| Example | R | R' | NMR, LCMS |
|---|---|---|---|
| 2 | 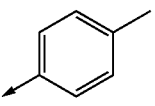 |  | $^1$H-NMR (CDCl$_3$) δ: 8.13-8.11 (1H, m), 8.06-8.04 (1H, m), 7.74 (2H, d, J = 8.3 Hz), 7.62-7.54 (2H, m), 7.24 (2H, d, J = 7.8 Hz), 3.56 (3H, s), 3.42 (3H, s), 2.38 (3H, s). R.T. 1.04 min, m/z 316 (M + 1) |
| 3 | 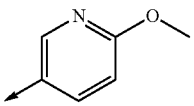 |  | $^1$H-NMR (CDCl$_3$) δ: 8.78 (1H, d, J = 2.3 Hz), 8.14-8.09 (2H, m), 8.03 (1H, dd, J = 8.7, 2.3 Hz), 7.60-7.53 (2H, m), 6.79 (1H, d, J = 8.7 Hz), 3.97 (3H, s), 3.55 (3H, s), 3.41 (3H, s). R.T. 0.95 min, m/z 333 (M + 1) |
| 4 | 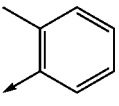 |  | $^1$H-NMR (CDCl$_3$) δ: 8.10-8.08 (2H, m), 7.63-7.56 (2H, m), 7.30-7.21 (4H, m), 3.55 (3H, s), 3.34 (3H, s), 2.23 (3H, s). R.T. 1.09 min, m/z 316 (M + 1) |
| 5 | 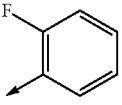 | 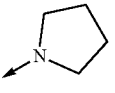 | $^1$H-NMR (CDCl$_3$) δ: 8.15-8.08 (2H, m), 7.64-7.56 (2H, m), 7.52-7.48 (1H, m), 7.38-7.33 (1H, m), 7.20 (1H, t, J = 7.6 Hz), 7.14 (1H, t, J = 9.2 Hz), 3.57 (3H, s), 3.39 (3H, s). R.T. 0.98 min, m/z 320 (M + 1) |
| 6 | 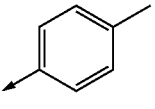 | 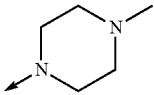 | $^1$H-NMR (CDCl$_3$) δ: 8.13-8.10 (1H, m), 8.06-8.03 (1H, m), 7.74 (2H, d, J = 7.8 Hz), 7.61-7.52 (2H, m), 7.23 (2H, d, J = 7.8 Hz), 4.05 (2H, t, J = 6.9 Hz), 3.86 (2H, t, J = 7.1 Hz), 2.38 (3H, s), 2.08-2.04 (4H, m). R.T. 1.04 min, m/z 342 (M + 1) |
| 7 | 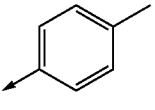 |  | $^1$H-NMR (CDCl$_3$) δ: 8.13-8.11 (1H, m), 8.05-8.02 (1H, m), 7.73 (2H, d, J = 8.3 Hz), 7.63-7.54 (2H, m), 7.24 (2H, d, J = 7.8 Hz), 4.23-4.18 (2H, m), 4.07-4.02 (2H, m), 2.61-2.54 (4H, m), 2.38 (3H, s), 2.37 (3H, s). R.T. 0.87 min, m/z 371 (M + 1) |
| 8 |  | 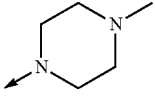 | $^1$H-NMR (CDCl$_3$) δ: 8.14-8.10 (1H, m), 8.09-8.05 (1H, m), 7.63-7.54 (2H, m), 7.45 (1H, t, J = 8.3 Hz), 6.77 (1H, dd, J = 8.5, 2.5 Hz), 6.70 (1H, dd, J = 11.7, 2.5 Hz), 3.83 (3H, s), 3.57 (3H, s), 3.40 (3H, s). R.T. 0.97 min, m/z 350 (M + 1) |
| 9 | 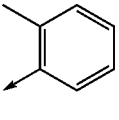 | | $^1$H-NMR (CDCl$_3$) δ: 8.13-8.09 (1H, m), 8.09-8.06 (1H, m), 7.65-7.56 (2H, m), 7.29-7.21 (4H, m), 4.20 (2H, t, J = 5.0 Hz), 3.96 (2H, t, J = 5.0 Hz), 2.58 (2H, t, J = 5.3 Hz), 2.51 (2H, t, J = 5.0 Hz), 2.35 (3H, s), 2.23 (3H, s). R.T. 0.91 min, m/z 371 (M + 1) |

TABLE 3-continued

| Example | R | R' | NMR, LCMS |
|---|---|---|---|
| 10 | -N(CH₃)₂ | 2-methoxyphenyl | ¹H-NMR (CDCl₃) δ: 8.12-8.06 (2H, m), 7.62-7.53 (2H, m), 7.39-7.32 (2H, m), 7.05-6.96 (2H, m), 3.77 (3H, s), 3.54 (3H, s), 3.35 (3H, s).<br>R.T. 0.81 min, m/z 332 (M + 1) |
| 11 | -N(CH₃)₂ | 2-(morpholin-4-yl)phenyl | ¹H-NMR (CDCl₃) δ: 8.11-8.07 (2H, m), 7.65-7.55 (2H, m), 7.41-7.34 (2H, m), 7.19-7.14 (2H, m), 3.55 (3H, s), 3.50 (4H, t, J = 4.4 Hz), 3.34 (3H, s), 2.96-2.91 (2H, m), 2.84-2.79 (2H, m).<br>R.T. 0.79 min, m/z 387 (M + 1) |
| 12 | -N(CH₃)₂ | 2-fluoro-6-methoxyphenyl | ¹H-NMR (CDCl₃) δ: 8.14-8.07 (2H, m), 7.65-7.54 (2H, m), 7.37-7.28 (1H, m), 6.82-6.76 (2H, m), 3.78 (3H, s), 3.56 (3H, s), 3.38 (3H, s).<br>R.T. 0.89 min, m/z 350 (M + 1) |
| 13 | -N(CH₃)₂ | 2-(pyrrolidin-1-yl)phenyl | ¹H-NMR (CDCl₃) δ: 8.11-8.03 (2H, m), 7.60-7.54 (2H, m), 7.25-7.16 (2H, m), 6.82-6.73 (2H, m), 3.55 (3H, s), 3.35 (3H, s), 3.31-3.23 (2H, m), 3.16-3.09 (2H, m), 1.85-1.70 (4H, m).<br>R.T. 0.75 min, m/z 371 (M + 1) |
| 14 | -N(CH₃)₂ | quinolin-8-yl | ¹H-NMR (CDCl₃) δ: 8.84 (1H, dd, J = 4.1, 1.8 Hz), 8.16 (1H, dd, J = 8.3, 1.4 Hz), 8.13-8.10 (2H, m), 7.87 (1H, dd, J = 8.0, 1.6 Hz), 7.81 (1H, dd, J = 7.3, 1.6 Hz), 7.64-7.58 (3H, m), 7.36 (1H, dd, J = 8.3, 4.6 Hz), 3.55 (3H, s), 3.29 (3H, s).<br>R.T. 0.67 min, m/z 353 (M + 1) |
| 15 | -N(CH₃)₂ | 2,6-dimethylphenyl | ¹H-NMR (CDCl₃) δ: 8.14-8.11 (1H, m), 8.08-8.04 (1H, m), 7.63-7.54 (4H, m), 7.31 (1H, t, J = 8.0 Hz), 7.15 (1H, d, J = 8.3 Hz), 3.57 (3H, s), 3.42 (3H, s), 2.40 (3H, s).<br>R.T. 1.08 min, m/z 316 (M + 1) |
| 16 | -N(CH₃)₂ | 5-methoxy-2-methylphenyl | ¹H-NMR (CDCl₃) δ: 8.12-8.05 (2H, m), 7.63-7.54 (2H, m), 7.21 (1H, d, J = 8.3 Hz), 6.84-6.77 (2H, m), 3.83 (3H, s), 3.55 (3H, s), 3.35 (3H, s), 2.22 (3H, s).<br>R.T. 0.94 min, m/z 346 (M + 1) |
| 17 | -N(CH₃)₂ | 2-(dimethylamino)phenyl | ¹H-NMR (CDCl₃) δ: 8.08 (2H, tt, J = 6.6, 2.4 Hz), 7.61-7.54 (2H, m), 7.34-7.29 (1H, m), 7.26-7.25 (1H, m), 7.12-7.10 (1H, m), 7.03-7.01 (1H, m), 3.54 (3H, s), 3.33 (3H, s), 2.65 (6H, s).<br>R.T. 0.62 min, m/z 345 (M + 1) |

TABLE 3-continued

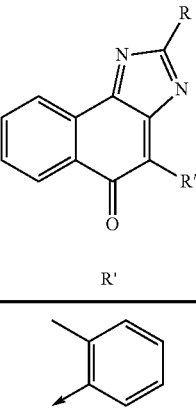

| Example | R | R' | NMR, LCMS |
|---|---|---|---|
| 18 | 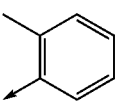 | 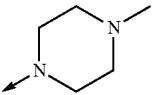 | ¹H-NMR (CDCl₃) δ: 8.12-8.11 (1H, m), 8.08-8.06 (1H, m), 7.62-7.60 (2H, m), 7.29-7.23 (4H, m), 4.19-4.18 (2H, m), 3.95-3.94 (2H, m), 3.85 (2H, t, J = 4.6 Hz), 3.79 (2H, t, J = 5.0 Hz), 2.22 (3H, s). R.T. 0.69 min, m/z 358 (M + 1) |
| 19 | 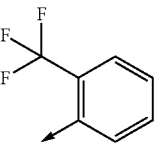 |  | ¹H-NMR (CDCl₃) δ: 8.12-8.07 (2H, m), 7.75 (1H, d, J = 7.8 Hz), 7.63-7.58 (3H, m), 7.50 (1H, t, J = 7.6 Hz), 7.36 (1H, d, J = 7.3 Hz), 4.26-4.25 (1H, m), 4.16-4.12 (1H, m), 4.00-3.96 (1H, m), 3.92-3.87 (1H, m), 2.63-2.45 (4H, m), 2.35 (3H, s). R.T. 0.72 min, m/z 425 (M + 1) |
| 20 | 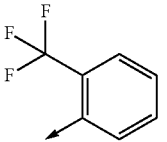 |  | ¹H-NMR (CDCl₃) δ: 8.11-8.10 (2H, m), 7.75 (1H, d, J = 7.3 Hz), 7.65-7.57 (3H, m), 7.50 (1H, t, J = 7.6 Hz), 7.36 (1H, d, J = 7.8 Hz), 3.56 (3H, s), 3.32 (3H, s). R.T. 1.01 min, m/z 370 (M + 1) |
| 21 | 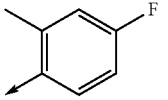 | 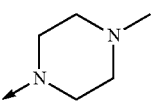 | ¹H-NMR (CDCl₃) δ: 8.12-8.08 (2H, m), 7.62-7.58 (2H, m), 7.23 (1H, dd, J = 8.5, 6.2 Hz), 6.97-6.94 (2H, m), 3.57 (3H, s), 3.36 (3H, s), 2.22 (3H, s). R.T. 1.00 min, m/z 334 (M + 1) |
| 22 | 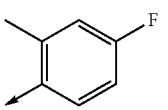 |  | ¹H-NMR (CDCl₃) δ: 8.13-8.05 (2H, m), 7.65-7.56 (2H, m), 7.23 (1H, dd, J = 8.7, 6.0 Hz), 7.00-6.90 (2H, m), 4.23-4.18 (2H, m), 3.99-3.94 (2H, m), 2.58 (2H, t, J = 5.0 Hz), 2.53 (2H, t, J = 5.0 Hz), 2.36 (3H, s), 2.22 (3H, s). R.T. 0.71 min, m/z 389 (M + 1) |
| 23 | 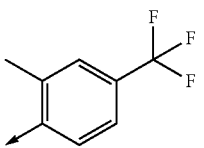 | 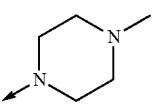 | ¹H-NMR (CDCl₃) δ: 8.14-8.09 (2H, m), 7.67-7.57 (2H, m), 7.52 (1H, s), 7.48 (1H, d, J = 8.0 Hz), 7.38 (1H, d, J = 8.0 Hz), 3.58 (3H, s), 3.36 (3H, s), 2.28 (3H, s). R.T. 1.22 min, m/z 384 (M + 1) |
| 24 | 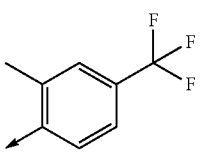 | 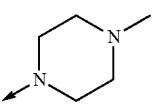 | ¹H-NMR (CDCl₃) δ: 8.14-8.07 (2H, m), 7.67-7.57 (2H, m), 7.52 (1H, s), 7.48 (1H, d, J = 8.3 Hz), 7.37 (1H, d, J = 8.3 Hz), 4.24-4.19 (2H, m), 3.99-3.95 (2H, m), 2.61-2.57 (2H, m), 2.56-2.51 (2H, m), 2.36 (3H, s), 2.28 (3H, s). R.T. 0.77 min, m/z 439 (M + 1) |

TABLE 3-continued

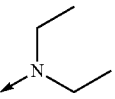

| Example | R | R' | NMR, LCMS |
|---|---|---|---|
| 25 | 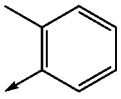 |  | $^1$H-NMR (CDCl$_3$) δ: 8.12-8.08 (2H, m), 7.62-7.57 (2H, m), 7.28-7.23 (4H, m), 4.05-4.01 (1H, m), 3.89-3.83 (2H, m), 3.67-3.63 (1H, m), 2.24 (3H, s), 1.35 (3H, t, J = 7.3 Hz), 1.28 (3H, t, J = 7.1 Hz). R.T. 1.17 min, m/z 344 (M + 1) |
| 26 | 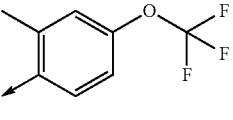 | 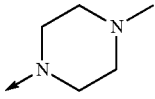 | $^1$H-NMR (CDCl$_3$) δ: 8.12-8.09 (2H, m), 7.63-7.58 (2H, m), 7.29 (1H, d, J = 8.3 Hz), 7.10-7.08 (2H, m), 3.57 (3H, s), 3.37 (3H, s), 2.24 (3H, s). R.T. 1.23 min, m/z 400 (M + 1) |
| 27 | 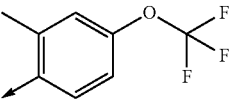 |  | $^1$H-NMR (CDCl$_3$) δ: 8.11-8.09 (2H, m), 7.65-7.57 (2H, m), 7.28 (1H, d, J = 8.3 Hz), 7.10-7.08 (2H, m), 4.22-4.21 (2H, m), 3.98-3.98 (2H, m), 2.59 (2H, t, J = 5.0 Hz), 2.54 (2H, t, J = 5.0 Hz), 2.36 (3H, s), 2.24 (3H, s). R.T. 0.82 min, m/z 455 (M + 1) |
| 28 | 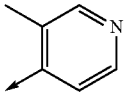 | 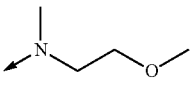 | $^1$H-NMR (CDCl$_3$) δ: 8.52 (1H, s), 8.47 (1H, d, J = 5.0 Hz), 8.12-8.11 (2H, m), 7.67-7.59 (2H, m), 7.20 (1H, d, J = 5.0 Hz), 3.59 (3H, s), 3.37 (3H, s), 2.22 (3H, s). R.T. 0.91 min, m/z 317 (M + 1) |
| 29 | 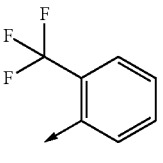 | 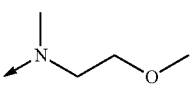 | $^1$H-NMR (CDCl$_3$) δ: 8.12-8.07 (2H, m), 7.77-7.72 (1H, m), 7.65-7.55 (3H, m), 7.52-7.46 (1H, m), 7.35 (1H, dd, J = 17.2, 7.6 Hz), 4.23-4.16 (0.57H, m), 4.04-3.97 (0.57H, m), 3.94-3.89 (0.43H, m), 3.78-3.72 (0.43H, m), 3.71-3.67 (2H, m), 3.62 (1.3H, s), 3.38 (1.7H, s), 3.37 (1.7H, s), 3.32 (1.3H, s). R.T. 1.09 min, m/z 414 (M + 1) |
| 30 | 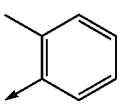 |  | $^1$H-NMR (CDCl$_3$) δ: 8.10-8.08 (2H, m), 7.60-7.58 (2H, m), 7.26-7.24 (4H, m), 4.17-4.14 (0.57H, m), 4.06-4.04 (0.57H, m), 3.95-3.90 (0.43H, m), 3.83-3.78 (0.43H, m), 3.70-3.65 (2H, m), 3.62 (1.29H, s), 3.39 (1.71H, s), 3.38 (1.71H, s), 3.35 (1.29H, s), 2.24 (1.71H, s), 2.23 (1.29H, s). R.T. 1.03 min, m/z 360 (M + 1) |
| 31 | 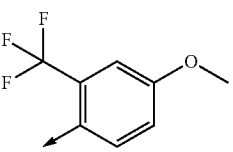 | | $^1$H-NMR (CDCl$_3$) δ: 8.11-8.08 (2H, m), 7.63-7.57 (2H, m), 7.29-7.26 (2H, m), 7.11 (1H, dd, J = 8.5, 2.5 Hz), 3.88 (3H, s), 3.55 (3H, s), 3.33 (3H, s). R.T. 1.02 min, m/z 400 (M + 1) |

TABLE 3-continued

| Example | R | R' | NMR, LCMS |
|---|---|---|---|
| 32 | 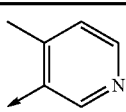 |  | ¹H-NMR (CDCl₃) δ: 8.48 (1H, s), 8.44 (1H, d, J = 5.1 Hz), 8.13-8.10 (2H, m), 7.66-7.58 (2H, m), 7.19 (1H, d, J = 5.1 Hz), 3.58 (3H, s), 3.36 (3H, s), 2.24 (3H, s). R.T. 0.58 min, m/z 317 (M + 1) |
| 33 | 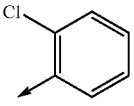 |  | ¹H-NMR (CDCl₃) δ: 8.13-8.09 (2H, m), 7.62-7.59 (2H, m), 7.47-7.46 (1H, m), 7.39-7.37 (1H, m), 7.33-7.31 (2H, m), 3.57 (3H, s), 3.36 (3H, s). R.T. 0.98 min, m/z 336 (M + 1) |
| 34 | 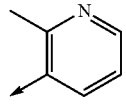 |  | ¹H-NMR (CDCl₃) δ: 8.51-8.50 (1H, m), 8.12-8.11 (2H, m), 7.64-7.61 (3H, m), 7.19 (1H, dd, J = 7.8, 5.0 Hz), 3.59 (3H, s), 3.37 (3H, s), 2.47 (3H, s). R.T. 0.56 min, m/z 317 (M + 1) |
| 35 | 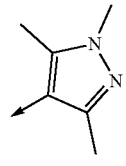 |  | ¹H-NMR (CDCl₃) δ: 8.11-8.09 (1H, m), 8.07-8.05 (1H, m), 7.61-7.54 (2H, m), 3.75 (3H, s), 3.56 (3H, s), 3.38 (3H, s), 2.19 (3H, s), 2.17 (3H, s). R.T. 0.69 min, m/z 334 (M + 1) |
| 36 | 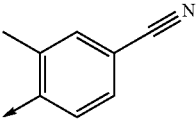 | 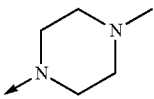 | ¹H-NMR (CDCl₃) δ: 8.11 (2H, dd, J = 7.6, 1.5 Hz), 7.65-7.61 (2H, m), 7.56 (1H, s), 7.52 (1H, d, J = 8.0 Hz), 7.37 (1H, d, J = 8.0 Hz), 3.59 (3H, s), 3.37 (3H, s), 2.26 (3H, s). R.T. 1.02 min, m/z 341 (M + 1) |
| 37 | 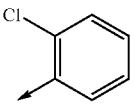 |  | ¹H-NMR (Acetone-D6) δ: 8.14-8.11 (1H, m), 8.06-8.04 (1H, m), 7.77-7.71 (2H, m), 7.49-7.47 (1H, m), 7.41-7.35 (3H, m), 4.22-4.18 (2H, m), 3.91-3.87 (2H, m), 2.60-2.57 (2H, m), 2.52-2.49 (2H, m), 2.30 (3H, s). R.T. 0.65 min, m/z 391 (M + 1) |
| 38 | 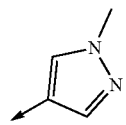 |  | ¹H-NMR (CDCl₃) δ: 8.68 (1H, s), 8.55 (1H, s), 8.06-8.05 (1H, m), 7.99-7.97 (1H, m), 7.56-7.53 (2H, m), 3.96 (3H, s), 3.57 (3H, s), 3.49 (3H, s). R.T. 0.92 min, m/z 306 (M + 1) |
| 39 | 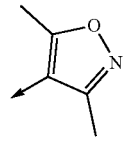 | | ¹H-NMR (CDCl₃) δ: 8.12-8.08 (2H, m), 7.65-7.57 (2H, m), 3.59 (3H, s), 3.40 (3H, s), 2.37 (3H, s), 2.24 (3H, s). R.T. 0.91 min, m/z 321 (M + 1) |

TABLE 3-continued

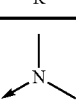

| Example | R | R' | NMR, LCMS |
|---|---|---|---|
| 40 | 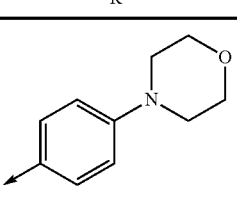 | 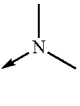 | $^1$H-NMR (CDCl$_3$) δ: 8.11-8.09 (1H, m), 8.04-8.02 (1H, m), 7.92 (2H, d, J = 9.0 Hz), 7.59-7.52 (2H, m), 6.95 (2H, d, J = 9.0 Hz), 3.87 (4H, t, J = 4.8 Hz), 3.55 (3H, s), 3.43 (3H, s), 3.25 (4H, t, J = 4.9 Hz).<br>R.T. 0.90 min, m/z 387 (M + 1) |
| 41 | 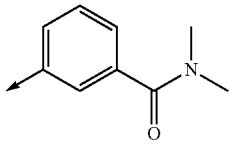 |  | $^1$H-NMR (CDCl$_3$) δ: 8.14-8.11 (1H, m), 8.08-8.06 (1H, m), 7.90-7.88 (2H, m), 7.64-7.56 (2H, m), 7.47-7.45 (2H, m), 3.58 (3H, s), 3.42 (3H, s), 3.12 (6H, s).<br>R.T. 0.83 min, m/z 373 (M + 1) |
| 42 | 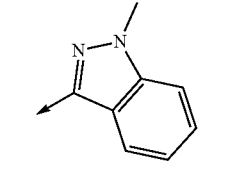 |  | $^1$H-NMR (CDCl$_3$) δ: 8.20-8.18 (1H, m), 8.11-8.10 (1H, m), 7.82 (1H, d, J = 8.3 Hz), 7.64-7.60 (2H, m), 7.40-7.38 (2H, m), 7.17-7.13 (1H, m), 4.18 (3H, s), 3.59 (3H, s), 3.42 (3H, s).<br>R.T. 0.81 min, m/z 356 (M + 1) |
| 43 | 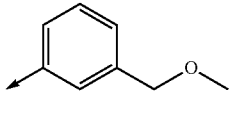 | 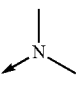 | $^1$H-NMR (CDCl$_3$) δ: 8.12-8.08 (2H, m), 7.64-7.53 (3H, m), 7.41-7.27 (3H, m), 4.50 (1H, d, J = 13.2 Hz), 4.41 (1H, d, J = 13.2 Hz), 3.56 (3H, s), 3.33 (3H, s), 3.23 (3H, s).<br>R.T. 0.90 min, m/z 346 (M + 1) |
| 44 | 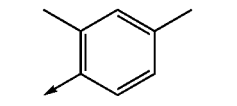 | 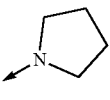 | $^1$H-NMR (CDCl$_3$) δ: 8.10-8.09 (2H, m), 7.61-7.57 (2H, m), 7.15 (1H, d, J = 7.6 Hz), 7.08 (2H, d, J = 7.6 Hz), 3.55 (3H, s), 3.35 (3H, s), 2.33 (3H, s), 2.18 (3H, s).<br>R.T. 1.06 min, m/z 330 (M + 1) |
| 45 | 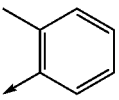 | 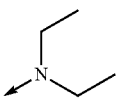 | $^1$H-NMR (CDCl$_3$) δ: 8.12-8.08 (2H, m), 7.61-7.58 (2H, m), 7.29-7.23 (4H, m), 4.06-4.05 (2H, m), 3.77-3.76 (2H, m), 2.23 (3H, s), 2.04-2.02 (4H, m).<br>R.T. 0.92 min, m/z 342 (M + 1) |
| 46 | 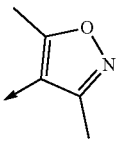 | 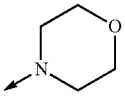 | $^1$H-NMR (CDCl$_3$) δ: 8.11-8.09 (2H, m), 7.64-7.56 (2H, m), 3.99 (2H, q, J = 7.2 Hz), 3.79 (2H, q, J = 7.2 Hz), 2.37 (3H, s), 2.25 (3H, s), 1.39-1.32 (6H, m).<br>R.T. 1.22 min, m/z 349 (M + 1) |
| 47 | 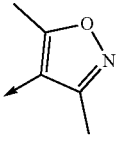 | | $^1$H-NMR (CDCl$_3$) δ: 8.12-8.11 (1H, m), 8.07-8.06 (1H, m), 7.64-7.60 (2H, m), 4.21 (2H, t, J = 4.9 Hz), 4.00 (2H, t, J = 4.9 Hz), 3.88-3.84 (4H, m), 2.36 (3H, s), 2.23 (3H, s).<br>R.T. 0.94 min, m/z 363 (M + 1) |

TABLE 3-continued

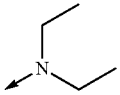

| Example | R | R' | NMR, LCMS |
|---|---|---|---|
| 48 | 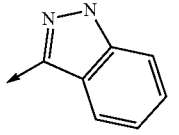 | 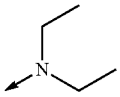 | $^1$H-NMR (CDCl$_3$) δ: 8.18 (1H, d, J = 7.3 Hz), 8.11 (1H, d, J = 7.3 Hz), 7.86 (1H, d, J = 8.3 Hz), 7.64-7.57 (2H, m), 7.40-7.36 (2H, m), 7.16-7.11 (1H, m), 4.18 (3H, s), 4.00 (2H, q, J = 7.3 Hz), 3.82 (2H, q, J = 7.3 Hz), 1.35 (3H, t, J = 7.3 Hz), 1.32 (3H, t, J = 7.3 Hz). R.T. 0.97 min, m/z 384 (M + 1) |
| 49 | 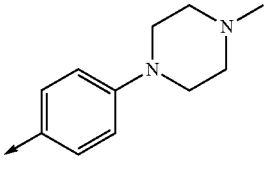 | 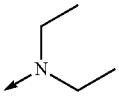 | $^1$H-NMR (CDCl$_3$) δ: 8.10-8.08 (1H, m), 8.03-8.01 (1H, m), 7.95-7.92 (2H, m), 7.56-7.53 (2H, m), 7.00-6.95 (2H, m), 3.96 (2H, q, J = 7.1 Hz), 3.83 (2H, q, J = 7.2 Hz), 3.32 (4H, t, J = 5.0 Hz), 2.57 (4H, t, J = 5.1 Hz), 2.36 (3H, s), 1.37-1.32 (6H, m). R.T. 0.71 min, m/z 428 (M + 1) |
| 50 | 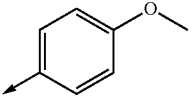 | 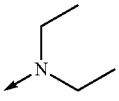 | $^1$H-NMR (CDCl$_3$) δ: 8.13-8.10 (1H, m), 8.06-8.03 (1H, m), 7.90 (2H, d, J = 8.7 Hz), 7.60-7.52 (2H, m), 6.97 (2H, d, J = 8.7 Hz), 3.97 (2H, q, J = 7.2 Hz), 3.85-3.81 (5H, m), 1.39-1.33 (6H, m). R.T. 1.25 min, m/z 360 (M + 1) |
| 51 | 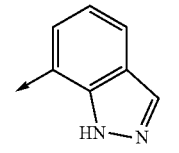 | 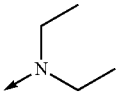 | $^1$H-NMR (CDCl$_3$) δ: 8.20-8.12 (3H, m), 7.84 (2H, t, J = 7.6 Hz), 7.69-7.59 (2H, m), 7.30-7.27 (1H, m), 4.04 (2H, q, J = 7.2 Hz), 3.83 (2H, q, J = 7.2 Hz), 1.41 (6H, t, J = 7.3 Hz). R.T. 1.10 min, m/z 370 (M + 1) |
| 52 | 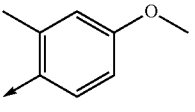 | 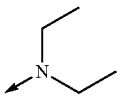 | $^1$H-NMR (CDCl$_3$) δ: 8.11-8.07 (2H, m), 7.61-7.54 (2H, m), 7.21 (1H, d, J = 8.3 Hz), 6.84-6.77 (2H, m), 4.06-3.97 (1H, m), 3.94-3.79 (5H, m), 3.72-3.60 (1H, m), 2.23 (3H, s), 1.34 (3H, t, J = 7.1 Hz), 1.29 (3H, t, J = 7.1 Hz). R.T. 1.14 min, m/z 374 (M + 1) |
| 53 | 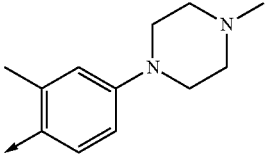 | 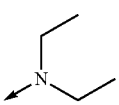 | $^1$H-NMR (CDCl$_3$) δ: 8.08-8.03 (2H, m), 7.57-7.51 (2H, m), 7.17 (1H, d, J = 8.3 Hz), 6.80-6.77 (2H, m), 4.02-3.95 (1H, m), 3.90-3.77 (2H, m), 3.68-3.60 (1H, m), 3.31 (4H, t, J = 4.6 Hz), 2.65 (4H, brs), 2.40 (3H, s), 2.20 (3H, s), 1.32 (3H, t, J = 7.3 Hz), 1.26 (3H, t, J = 7.3 Hz). R.T. 0.75 min, m/z 442 (M + 1) |
| 54 | 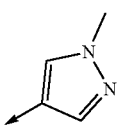 | | $^1$H-NMR (CDCl$_3$) δ: 8.71 (1H, s), 8.55 (1H, s), 8.07-8.03 (1H, m), 8.00-7.97 (1H, m), 7.58-7.48 (2H, m), 4.01-3.94 (5H, m), 3.89 (2H, q, J = 7.2 Hz), 1.41 (3H, t, J = 7.1 Hz), 1.36 (3H, t, J = 7.1 Hz). R.T. 1.16 min, m/z 334 (M + 1) |

TABLE 3-continued

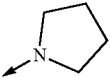

| Example | R | R' | NMR, LCMS |
|---|---|---|---|
| 55 | 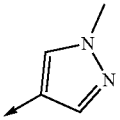 |  | $^1$H-NMR (CDCl$_3$) δ: 8.69 (1H, s), 8.56 (1H, s), 8.06-8.04 (1H, m), 7.99-7.96 (1H, m), 7.57-7.49 (2H, m), 4.05 (2H, t, J = 6.2 Hz), 3.96 (3H, s), 3.93 (2H, t, J = 6.4 Hz), 2.13-2.07 (4H, m). R.T. 0.94 min, m/z 332 (M + 1) |
| 56 | 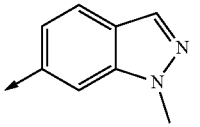 | 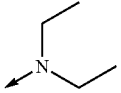 | $^1$H-NMR (CDCl$_3$) δ: 8.17-8.15 (1H, m), 8.10-8.08 (1H, m), 7.96 (1H, d, J = 0.9 Hz), 7.93 (1H, d, J = 0.9 Hz), 7.76-7.73 (1H, m), 7.66-7.57 (3H, m), 4.11 (3H, s), 3.59 (3H, s), 3.44 (3H, s). R.T. 0.95 min, m/z 356 (M + 1) |
| 57 | 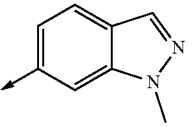 | 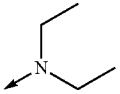 | $^1$H-NMR (CDCl$_3$) δ: 8.17-8.14 (1H, m), 8.11-8.07 (1H, m), 7.98 (1H, s), 7.97 (1H, s), 7.74 (1H, d, J = 8.5 Hz), 7.67-7.56 (3H, m), 4.10 (3H, s), 4.00 (2H, q, J = 7.1 Hz), 3.83 (2H, q, J = 7.1 Hz), 1.38 (3H, t, J = 7.1 Hz), 1.37 (3H, t, J = 7.1 Hz). R.T. 1.16 min, m/z 384 (M + 1) |
| 58 | 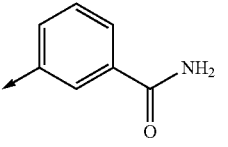 |  | $^1$H-NMR (CDCl$_3$) δ: 8.32 (1H, t, J = 1.7 Hz), 8.13 (1H, dd, J = 7.4, 1.3 Hz), 8.09-8.04 (2H, m), 7.87-7.84 (1H, m), 7.65-7.56 (2H, m), 7.52 (1H, t, J = 7.8 Hz), 6.19 (1H, br s), 5.53 (1H, br s), 4.00 (2H, q, J = 7.2 Hz), 3.83 (2H, q, J = 7.2 Hz), 1.373 (3H, t, J = 7.2 Hz), 1.370 (3H, t, J = 7.2 Hz). R.T. 0.91 min, m/z 373 (M + 1) |
| 59 | 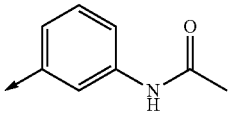 | 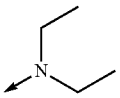 | $^1$H-NMR (CDCl$_3$) δ: 8.10 (1H, dd, J = 7.3, 1.4 Hz), 8.05 (1H, dd, J = 6.9, 1.4 Hz), 7.75-7.72 (2H, m), 7.62-7.54 (3H, m), 7.42-7.34 (2H, m), 3.56 (3H, s), 3.44 (3H, s), 2.13 (3H, s). R.T. 0.60 min, m/z 359 (M + 1) |
| 60 | 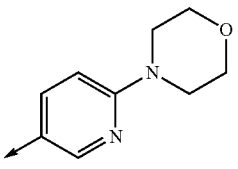 | 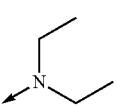 | $^1$H-NMR (CDCl$_3$) δ: 8.89 (1H, d, J = 1.8 Hz), 8.14 (1H, dd, J = 8.7, 1.8 Hz), 8.08-8.06 (1H, m), 8.03-8.00 (1H, m), 7.57-7.50 (2H, m), 6.68 (1H, d, J = 9.2 Hz), 3.95 (2H, q, J = 7.3 Hz ), 3.85-3.79 (6H, m), 3.59-3.57 (4H, m), 1.33 (3H, t, J = 7.3 Hz), 1.32 (3H, t, J = 7.3 Hz). R.T. 0.96 min, m/z 416 (M + 1) |
| 61 | 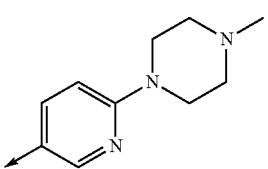 | | $^1$H-NMR (CDCl$_3$) δ: 8.88 (1H, d, J = 2.3 Hz), 8.13 (1H, dd, J = 8.7, 2.3 Hz), 8.08-8.06 (1H, m), 8.03-8.00 (1H, m), 7.57-7.50 (2H, m), 6.70 (1H, d, J = 9.2 Hz), 3.95 (2H, q, J = 7.3 Hz), 3.82 (2H, q, J = 7.3 Hz), 3.75 (4H, brs), 2.64 |

TABLE 3-continued

| Example | R | R' | NMR, LCMS |
|---|---|---|---|
|  |  |  | (4H, brs), 2.43 (3H, s), 1.33 (3H, t, J = 7.3 Hz), 1.32 (3H, t, J = 7.3 Hz).<br>R.T. 0.76 min, m/z 429 (M + 1) |
| 62 | dimethylamino | 4-methyl-3-(4-methylpiperazin-1-yl)phenyl | $^1$H-NMR (CDCl$_3$) δ: 8.08-8.03 (2H, m), 7.59-7.52 (2H, m), 7.17 (1H, d, J = 8.7 Hz), 6.80-6.77 (2H, m), 3.52 (3H, s), 3.32 (3H, s), 3.27 (4H, t, J = 4.6 Hz), 2.59 (4H, t, J = 4.6 Hz), 2.36 (3H, s), 2.18 (3H, s).<br>R.T. 0.63 min, m/z 414 (M + 1) |
| 63 | dimethylamino | 3-ethoxy-4-methylphenyl | $^1$H-NMR (CDCl$_3$) δ: 8.09-8.04 (2H, m), 7.60-7.53 (2H, m), 7.17 (1H, d, J = 8.3 Hz), 6.79-6.75 (2H, m), 4.04 (2H, q, J = 6.9 Hz), 3.53 (3H, s), 3.33 (3H, s), 2.19 (3H, s), 1.40 (3H, t, J = 6.9 Hz).<br>R.T. 1.01 min, m/z 360 (M + 1) |
| 64 | diethylamino | 3-ethoxy-4-methylphenyl | $^1$H-NMR (CDCl$_3$) δ: 8.09-8.03 (2H, m), 7.59-7.50 (2H, m), 7.17 (1H, d, J = 8.3 Hz), 6.79-6.75 (2H, m), 4.07-3.96 (3H, m), 3.91-3.78 (2H, m), 3.69-3.62 (1H, m), 2.20 (3H, s), 1.40 (3H, t, J = 6.9 Hz), 1.32 (3H, t, J = 6.9 Hz), 1.27 (3H, t, J = 6.9 Hz).<br>R.T. 1.21 min, m/z 388 (M + 1) |
| 65 | diethylamino | 2-methylpyridin-3-yl | $^1$H-NMR (CDCl$_3$) δ: 8.48 (1H, dd, J = 4.9, 2.0 Hz), 8.11-8.08 (2H, m), 7.63-7.55 (3H, m), 7.18 (1H, dd, J = 7.6, 4.9 Hz), 4.08-3.99 (1H, m), 3.93-3.78 (2H, m), 3.68-3.59 (1H, m), 2.47 (3H, s), 1.34 (3H, t, J = 7.3 Hz), 1.27 (3H, t, J = 7.3 Hz).<br>R.T. 0.70 min, m/z 345 (M + 1) |
| 66 | diethylamino | 3-acetamidophenyl | $^1$H-NMR (CDCl$_3$) δ: 8.10-8.04 (2H, m), 7.76 (1H, d, J = 7.8 Hz), 7.69 (1H, s), 7.61-7.50 (3H, m), 7.36 (1H, t, J = 7.8 Hz), 3.96 (2H, q, J = 7.1 Hz), 3.83 (2H, q, J = 7.1 Hz), 2.10 (3H, s), 1.36-1.30 (6H, m).<br>R.T. 0.93 min, m/z 387 (M + 1) |
| 67 | diethylamino | 4-methyl-3-(morpholinosulfonyl)phenyl | $^1$H-NMR (CDCl$_3$) δ: 8.10-8.08 (2H, m), 7.68-7.56 (4H, m), 7.42 (1H, d, J = 8.0 Hz), 4.01-3.91 (2H, m), 3.76-3.69 (6H, m), 3.06 (4H, t, J = 4.4 Hz), 2.30 (3H, s), 1.35 (3H, t, J = 7.1 Hz), 1.27 (3H, t, J = 7.1 Hz).<br>R.T. 0.70 min, m/z 493 (M + 1) |

TABLE 3-continued

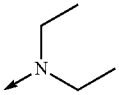

| Example | R | R' | NMR, LCMS |
|---|---|---|---|
| 68 | 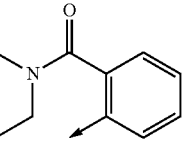 | 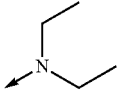 | $^1$H-NMR (CDCl$_3$) δ: 8.05-7.98 (2H, m), 7.61-7.32 (6H, m), 3.95-3.90 (2H, m), 3.79-3.77 (2H, m), 3.45 (4H, brs), 1.32-1.26 (6H, m), 1.16 (3H, t, J = 7.1 Hz), 0.93 (3H, t, J = 7.1 Hz). R.T. 1.13 min, m/z 429 (M + 1) |
| 69 | 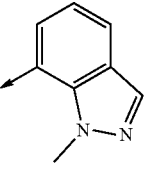 | 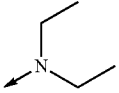 | $^1$H-NMR (CDCl$_3$) δ: 8.14-8.11 (2H, m), 7.97 (1H, d, J = 0.7 Hz), 7.72 (1H, dd, J = 8.0, 1.0 Hz), 7.64-7.58 (2H, m), 7.32-7.30 (1H, m), 7.19-7.15 (1H, m), 4.07-3.82 (5H, m), 3.78-3.61 (2H, m), 1.34 (3H, t, J = 7.1 Hz), 1.23 (3H, t, J = 7.1 Hz). R.T. 1.08 min, m/z 384 (M + 1) |
| 70 | 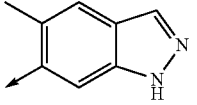 | 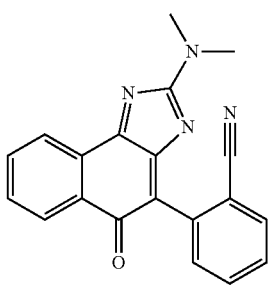 | $^1$H-NMR (CDCl$_3$) δ: 8.15-8.06 (2H, m), 7.64-7.56 (3H, m), 7.34 (1H, s), 7.17 (1H, s), 4.03-3.89 (2H, m), 3.80-3.71 (1H, m), 3.67-3.59 (1H, m), 2.26 (3H, s), 1.35 (3H, t, J = 7.3 Hz), 1.19 (3H, t, J = 7.1 Hz). R.T. 0.97 min, m/z 384 (M + 1) |

The points of the arrows represent the position of bonding with the main skeleton.

Example 71

2-[(2-dimethylamino)-5-oxo-5H-naphth[1,2-d]imidazol-4-yl]benzonitrile

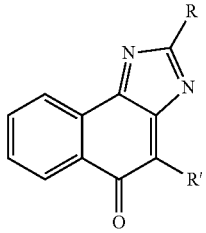

4-Chloro-2-(dimethylamino)-5H-naphth[1,2-d]imidazol-5-one (200 mg), 2-(2-cyanophenyl)-4,4,5,5,5-tetramethyl-1,3,2-dioxaborolane (353 mg), and bis(tri-tert-butylphosphine)palladium (0) (39 mg) were added to a mixed solution of 1,2-dimethoxyethane (12 mL) and aqueous saturated sodium carbonate solution (2 mL), and the reaction mixture was stirred at 120° C. for 30 minutes under microwave irradiation. The reaction solution was cooled to room temperature, and then water and chloroform were added to the reaction solution, and the target substance was extracted into the organic layer. The resulting organic layer was washed with saturated brine, and then dried over anhydrous sodium sulfate, and concentrated under reduced pressure. The residue was purified by silica gel column chromatography, and then the resulting solid was washed with ethyl acetate to yield Example 71 (15.5 mg). $^1$H-NMR (CDCl$_3$) δ: 8.17-8.15 (1H, m), 8.11-8.09 (1H, m), 7.76-7.74 (1H, m), 7.67-7.58 (4H, m), 7.45-7.43 (1H, m), 3.60 (3H, s), 3.41 (3H, s).

LC-MS: R.T. 0.93, 327.5 (M+1)

Examples 72 to 81

In accordance with the method described in Example 71, compounds of Examples 72 to 81 shown in the following table were obtained using compounds of Reference examples 1 to 6 and corresponding raw materials.

TABLE 4

| Example | R | R' | NMR, LCMS |
|---|---|---|---|
| 72 |  | 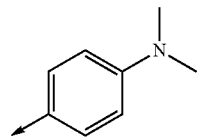 | ¹H-NMR (CDCl₃) δ: 8.09-8.08 (1H, m), 8.01-8.00 (1H, m), 7.98-7.94 (2H, m), 7.55-7.52 (2H, m), 6.79-6.75 (2H, m), 3.53 (3H, s), 3.42 (3H, s), 3.02 (6H, s). R.T. 0.92 min, m/z 345 (M + 1) |
| 73 |  | 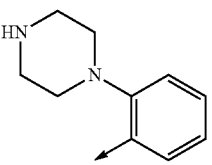 | ¹H-NMR (CDCl₃) δ: 8.11-8.06 (2H, m), 7.64-7.54 (2H, m), 7.40-7.33 (2H m) 7.19-7.11 (2H, m), 3.55 (3H, s), 3.34 (3H, s), 2.93-2.86 (2H, m), 2.83-2.75 (2H, m), 2.67 (4H, t, J = 4.6 Hz). R.T. 0.55 min, m/z 386 (M + 1) |
| 74 |  | 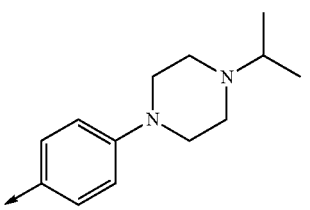 | 1H-NMR (CDCl₃) δ: 8.11-8.08 (1H, m), 8.03-8.01 (1H, m), 7.91 (2H, d, J = 9.2 Hz), 7.56-7.54 (2H, m), 6.96 (2H, d, J = 8.7 Hz), 3.55 (3H, s), 3.42 (3H, s), 3.31 (4H, t, J = 5.3 Hz), 2.72-2.69 (5H, m), 1.10 (6H, d, J = 6.4 Hz). R.T. 0.65 min, m/z 428 (M + 1) |
| 75 |  | 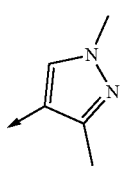 | ¹H-NMR (CDCl₃) δ: 8.09-8.06 (1H, m), 8.04-8.03 (1H, m), 7.73 (1H, s), 7.58-7.55 (2H, m), 3.88 (3H, s), 3.56 (3H, s), 3.40 (3H, s), 2.36 (3H, s). R.T. 0.71 min, m/z 320 (M + 1) |
| 76 |  | 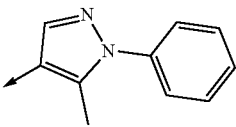 | 1H-NMR (CDCl₃) δ: 8.12 (1H, d, J = 7.1 Hz), 8.07-8.05 (2H, m), 7.60-7.46 (6H, m), 7.40-7.38 (1H, m), 3.58 (3H, s), 3.44 (3H, s), 2.38 (3H, s). R.T. 1.00 min, m/z 382 (M + 1) |
| 77 |  | 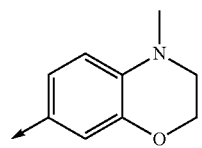 | ¹H-NMR (CDCl₃) δ: 8.11-8.06 (1H, m), 8.03-7.97 (1H, m), 7.58-7.51 (4H, m), 6.71 (1H, d, J = 8.5 Hz), 4.29 (2H, t, J = 4.4 Hz), 3.53 (3H, s), 3.43 (3H, s), 3.33 (2H, t, J = 4.5 Hz), 2.95 (3H, s). R.T. 0.89 min, m/z 373 (M + 1) |
| 78 |  | 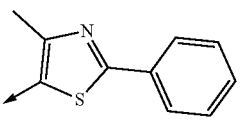 | ¹H-NMR (CDCl₃) δ: 8.14 (1H, dd, J = 7.4, 1.6 Hz), 8.08 (1H, dd, J = 7.3, 1.5 Hz), 7.97 (2H, dd, J = 7.8, 1.7 Hz), 7.65-7.57 (2H, m), 7.44-7.42 (3H, m), 3.61 (3H, s), 3.45 (3H, s), 2.51 (3H, s). R.T. 1.25 min, m/z 399 (M + 1) |
| 79 |  | 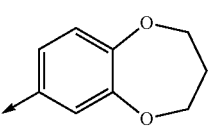 | ¹H-NMR (CDCl₃) δ: 8.12-8.10 (1H, m), 8.05-8.04 (1H, m), 7.59-7.56 (3H, m), 7.49 (1H, dd, J = 8.4, 2.1 Hz), 7.00 (1H, d, J = 8.5 Hz), 4.26 (4H, dd, J = 10.7, 5.1 Hz), 3.56 (3H, s), 3.44 (3H, s), 2.24-2.18 (2H, m). R.T. 1.03 min, m/z 374 (M + 1) |
| 80 |  | 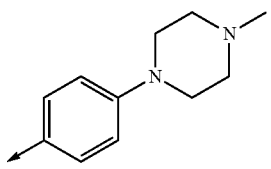 | ¹H-NMR (CDCl₃) δ: 8.11-8.08 (1H, m), 8.03-8.01 (1H, m), 7.91 (2H, d, J = 9.3 Hz), 7.58-7.52 (2H, m), 6.96 (2H, d, J = 9.3 Hz), 3.54 (3H, s), 3.42 (3H, s), 3.31 (4H, t, J = 5.1 Hz), 2.57 (4H, t, J = 5.1 Hz), 2.35 (3H, s). R.T. 0.61 min, m/z 400 (M + 1) |

TABLE 4-continued

| Example | R | R' | NMR, LCMS |
|---|---|---|---|
| 81 | morpholine (N-linked) | 2-(trifluoromethyl)phenyl | ¹H-NMR (CDCl$_3$) δ: 8.12-8.07 (2H, m), 7.75 (1H, d, J = 7.8 Hz), 7.62-7.60 (3H, m), 7.51-7.49 (1H, m), 7.35 (1H, d, J = 7.6 Hz), 4.21-4.16 (2H, m), 3.94-3.91 (2H, m), 3.85 (2H, t, J = 4.9 Hz), 3.79-3.77 (2H, m). R.T. 1.08 min, m/z 412 (M + 1) |

The points of the arrows represent the position of bonding with the main skeleton.

Examples 82 to 96

In accordance with the method described in Example 1, compounds of Examples 82 to 96 shown in the following table were synthesized using the compounds of Reference examples 1 and 2 and corresponding raw materials.

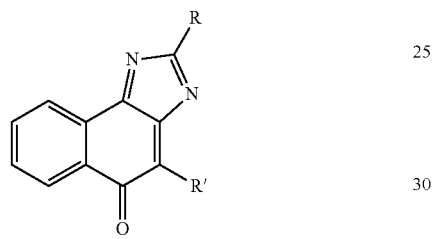

TABLE 5

| Example | R | R' | NMR, LCMS |
|---|---|---|---|
| 82 | N,N-dimethylamino | 2-chloro-4-methoxyphenyl | ¹H-NMR (CDCl$_3$) δ: 8.11-8.09 (2H, m), 7.62-7.54 (2H, m), 7.29 (1H, d, J = 8.7 Hz), 7.07 (1H, d, J = 2.8 Hz), 6.86 (1H, dd, J = 8.7, 2.7 Hz), 3.81 (3H, s), 3.54 (3H, s), 3.36 (3H, s). R.T. 1.02 min, m/z 367 (M + 1) |
| 83 | N,N-dimethylamino | 2-methyl-4-methoxyphenyl | ¹H-NMR (CDCl$_3$) δ: 8.13-8.04 (2H, m), 7.64-7.54 (2H, m), 7.15 (1H, d, J = 8.3 Hz), 6.84-6.81 (2H, m), 3.77 (3H, s), 3.54 (3H, s), 3.34 (3H, s), 2.13 (3H, s). R.T. 0.97 min, m/z 346 (M + 1) |
| 84 | N,N-diethylamino | 2-chloro-4-methoxyphenyl | ¹H-NMR (CDCl$_3$) δ: 8.11-8.06 (2H, m), 7.61-7.50 (2H, m), 7.29 (1H, d, J = 8.7 Hz), 7.01 (1H, d, J = 2.8 Hz), 6.86 (1H, dd, J = 8.7, 2.8 Hz), 4.03-3.68 (7H, m), 1.33 (3H, t, J = 7.3 Hz), 1.28 (3H, t, J = 7.3 Hz). R.T. 1.22 min, m/z 395 (M + 1) |
| 85 | N,N-diethylamino | 2-methyl-4-methoxyphenyl | ¹H-NMR (CDCl$_3$) δ: 8.10-8.07 (2H, m), 7.62-7.54 (2H, m), 7.15 (1H, d, J = 8.0 Hz), 6.84-6.80 (2H, m), 4.04-3.70 (7H, m), 2.14 (3H, s), 1.33 (3H, t, J = 7.1 Hz), 1.27 (3H, t, J = 7.1 Hz). R.T. 1.18 min, m/z 374 (M + 1) |
| 86 | N,N-dimethylamino | 2-chloro-5-methoxyphenyl | ¹H-NMR (CDCl$_3$) δ: 8.12-8.06 (2H, m), 7.63-7.54 (2H, m), 7.33 (1H, d, J = 8.7 Hz), 6.91 (1H. d, J = 2.8 Hz), 6.85 (1H, dd, J = 8.7, 2.8 Hz), 3.78 (3H, s), 3.55 (3H, s), 3.35 (3H, s). R.T. 1.04 min, m/z 367 (M + 1) |

TABLE 5-continued

| Example | R | R' | NMR, LCMS |
|---|---|---|---|
| 87 |  | 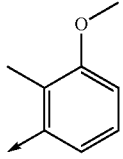 | ¹H-NMR (CDCl₃) δ: 8.10-8.05 (2H, m), 7.61-7.53 (2H, m), 7.19 (1H, t, J = 7.8 Hz), 6.87-6.84 (2H, m), 3.84 (3H, s), 3.53 (3H, s), 3.32 (3H, s), 2.05 (3H, s). R.T. 0.98 min, m/z 346 (M + 1) |
| 88 | 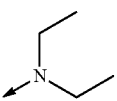 | 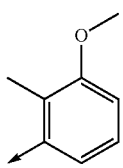 | ¹H-NMR (CDCl₃) δ: 8.10-8.06 (2H, m), 7.60-7.53 (2H, m), 7.19 (1H, t, J = 7.8 Hz), 6.87-6.84 (2H, m), 4.05-3.59 (7H, m), 2.06 (3H, s), 1.32 (3H, t, J = 7.1 Hz), 1.25 (3H, t, J = 7.1 Hz). R.T. 1.20 min, m/z 374 (M + 1) |
| 89 |  | 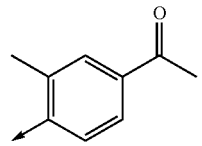 | ¹H-NMR (CDCl₃) δ: 8.10-8.05 (2H, m), 7.85-7.79 (2H, m), 7.63-7.55 (2H, m), 7.35 (1H, d, J = 7.3 Hz), 3.55 (3H, s), 3.33 (3H, s), 2.60 (3H, s), 2.27 (3H, s). R.T. 0.97 min, m/z 358 (M + 1) |
| 90 |  | 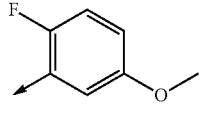 | ¹H-NMR (CDCl₃) δ: 8.12-8.05 (2H, m), 7.62-7.54 (2H, m), 7.05-7.00 (2H, m), 6.88-6.84 (1H, m), 3.78 (3H, s), 3.56 (3H, s), 3.38 (3H, s). R.T. 0.99 min, m/z 350 (M + 1) |
| 91 | 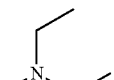 | 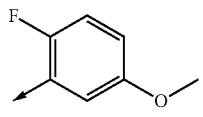 | ¹H-NMR (CDCl₃) δ: 8.14-8.08 (2H, m), 7.63-7.55 (2H, m), 7.07-7.02 (2H, m), 6.90-6.85 (1H, m), 3.98 (2H, q, J = 7.1 Hz), 3.83-3.76 (5H, m), 1.36 (3H, t, J = 7.1 Hz), 1.33 (3H, t, J = 7.1 Hz). R.T. 1.20 min, m/z 378 (M + 1) |
| 92 |  | 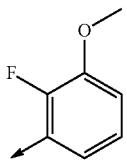 | ¹H-NMR (CDCl₃) δ: 8.14-8.07 (2H, m), 7.64-7.56 (2H, m), 7.14-7.10 (1H, m), 7.06-6.97 (2H, m), 3.91 (3H, s), 3.57 (3H, s), 3.39 (3H, s). R.T. 0.97 min, m/z 350 (M + 1) |
| 93 | 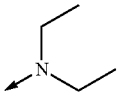 | 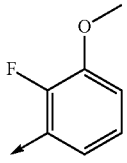 | ¹H-NMR (CDCl₃) δ: 8.14-8.08 (2H, m), 7.63-7.55 (2H, m), 7.14-7.10 (1H, m), 7.06-6.96 (2H, m), 3.97 (2H, q, J = 7.1 Hz), 3.91 (3H, s), 3.78 (2H, q, J = 7.1 Hz), 1.35 (3H, t, J = 7.1 Hz), 1.31 (3H, t, J = 7.1 Hz). R.T. 1.17 min, m/z 378 (M + 1) |
| 94 |  | 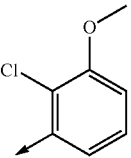 | ¹H-NMR (CDCl₃) δ: 8.11-8.06 (2H, m), 7.62-7.54 (2H, m), 7.29-7.25 (1H, m), 6.97-6.94 (2H, m), 3.91 (3H, s), 3.54 (3H, s), 3.33 (3H, s). R.T. 0.98 min, m/z 367 (M + 1) |
| 95 | 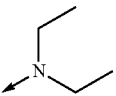 | 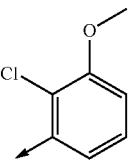 | ¹H-NMR (CDCl₃) δ: 8.11-8.07 (2H, m), 7.61-7.53 (2H, m), 7.29-7.25 (1H, m), 6.97-6.93 (2H, m), 4.04-3.65 (7H, m), 1.33 (3H, t, J = 7.3 Hz), 1.26 (3H, t, J = 7.3 Hz). R.T. 1.18 min, m/z 395 (M + 1) |

TABLE 5-continued

| Example | R | R' | NMR, LCMS |
|---|---|---|---|
| 96 | 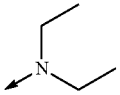 | 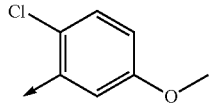 | $^1$H-NMR (CDCl$_3$) δ: 8.12-8.08 (2H, m), 7.63-7.55 (2H, m), 7.33 (1H, d, J = 8.7 Hz), 6.91 (1H, d, J = 3.2 Hz), 6.85 (1H, dd, J = 8.7, 3.2 Hz), 4.04-3.78 (7H, m), 1.34 (3H, t, J = 7.3 Hz), 1.29 (3H, t, J = 7.3 Hz). R.T. 1.23 min, m/z 395 (M + 1) |

The points of the arrows represent the position of bonding with the main skeleton.

Test Example 1

Cell Viability Evaluation Test Using Human Dermal Fibroblasts Derived from a Friedreich Ataxia Patient Compounds described herein were tested for their ability to rescue Friedreich ataxia patient-derived dermal fibroblasts stressed by the addition of L-buthionine-(S,R)-sulfoximine (BSO).

A MEMα medium and a Medium 199 medium were obtained from Thermo Scientific, and fetal bovine serum was obtained from DS Pharma. Basic fibroblast growth factor (b-FGF) was purchased from Funakoshi Co., Ltd. and epidermal growth factor (EGF) was purchased from PeproTech Inc. L-Buthionine-(S,R)-sulfoximine and bovine pancreas-derived insulin were purchased from Sigma. Calcein-AM was purchased from DOJINDO. An assay medium is a medium of 64% MEMα medium and 25% Medium 199 medium, and contains 10% fetal bovine serum, EGF whose final concentration is 10 ng/ml, 10 ng/ml of bFGF, and 10 µg/mL insulin. Cells were purchased from Coriell Institute.

A test compound was dissolved in DMSO to make a 1 mM or 10 mM stock solution. From this stock solution, serially diluted solutions were further prepared using DMSO and used in an assay.

Friedreich ataxia patient-derived human dermal fibroblasts were suspended in an assay medium, seeded into a 384-well plate at 650 cells/well/20 µl, and incubated at 37° C. in a 5% carbon dioxide incubator overnight. A test compound solution prepared in an assay medium from the serially diluted solution (DMSO) at 5 times higher than the final concentration was added in 10 µL per well of the cell-seeded plate. Then, 10 µL of 150 µM BSO solution was added. The amount of a reaction solution was adjusted to be finally 50 µL, and the final BSO concentration was made at 30 µM. The plate was incubated at 37° C. in 5% CO$_2$ for 48 hours, and then media were removed from all wells, and 20 µl of a Calcein-AM solution, which had been 550-fold diluted by PBS, was added to each well. The plate was incubated at 37° C. for 20 to 30 minutes, and then fluorescence (485 nm/525 nm of excitation/radiation wavelength) was measured by a fluorescence plate reader.

The degree of the viability of fibroblasts that were not treated with BSO was regarded as 100%, the degree of the viability of cells that were treated with BSO only (without a compound) was regarded as 0%, and the viability of cells that were treated with a compound was calculated. Results are shown in Table 6.

TABLE 6

| Example | EC$_{50}$ (nmol/L) |
|---|---|
| 1 | 20-100 |
| 2 | 17 |
| 3 | <20 |
| 4 | 3.7 |
| 5 | 14 |
| 6 | <20 |
| 7 | 3 |
| 8 | 10 |
| 9 | 2 |
| 10 | 5.1 |
| 11 | 6.4 |
| 12 | 6.4 |
| 13 | 5.4 |
| 14 | 41 |
| 15 | 6 |
| 16 | 9.1 |
| 17 | 8.5 |
| 18 | 10.5 |
| 19 | 3 |
| 20 | <3 |
| 21 | 7.9 |
| 22 | 1.9 |
| 23 | 5.9 |
| 24 | 2.4 |
| 25 | 21 |
| 26 | 7.2 |
| 27 | 4 |
| 28 | 4.8 |
| 29 | 12 |
| 30 | 10 |
| 31 | 15 |
| 32 | 6 |
| 33 | 16 |
| 34 | 7 |
| 35 | 2.5 |
| 36 | 9.5 |
| 37 | <3 |
| 38 | 18.8 |
| 39 | 6.1 |
| 40 | 11.6 |
| 41 | 12.9 |
| 42 | 5.1 |
| 43 | 20.1 |
| 44 | 17 |
| 45 | 8.4 |
| 46 | 14.9 |
| 47 | 4.9 |
| 48 | 4.1 |
| 49 | 4.3 |
| 50 | 16.8 |
| 51 | 11.8 |
| 52 | 19.1 |
| 53 | 11.4 |
| 54 | 12.1 |
| 55 | 21.1 |
| 56 | 14.5 |
| 57 | 18 |
| 58 | 0.9 |
| 59 | 4 |
| 60 | 17.4 |
| 61 | 4.2 |
| 62 | 5.5 |
| 63 | 18.4 |
| 64 | 47.7 |

TABLE 6-continued

| Example | EC$_{50}$ (nmol/L) |
|---|---|
| 65 | 9 |
| 66 | 6.7 |
| 67 | >100 |
| 68 | 40.5 |
| 69 | 14.2 |
| 70 | 6.7 |
| 71 | 15 |
| 72 | 20-100 |
| 73 | 7.2 |
| 74 | <3 |
| 75 | 12.1 |
| 76 | 20.3 |
| 77 | 17 |
| 78 | >100 |
| 79 | 39.1 |
| 80 | 10 |
| 81 | 14.8 |
| 82 | 16.5 |
| 83 | 18.3 |
| 84 | 25.1 |
| 85 | 22.9 |
| 86 | 14.9 |
| 87 | 17.1 |
| 88 | 17.1 |
| 89 | 14.3 |
| 90 | 14.0 |
| 91 | 19.0 |
| 92 | 30.2 |
| 93 | 29.1 |
| 94 | 22.6 |
| 95 | 34.3 |
| 96 | 18.9 |

As shown in Table 6, the compounds of the present disclosure exhibited activity to rescue Friedreich ataxia patient-derived fibroblasts stressed by addition of BSO in the cell viability evaluation test using human dermal fibroblasts derived from Friedreich ataxia patients. It should be noted that the description "20-100" in Table 6 indicates that an EC$_{50}$ value is a value between 20 nmol/L and 100 nmol/L; the descriptions "<20" and "<3" indicate that an EC$_{50}$ value is a lower concentration than 20 nmol/L and 3 nmol/L, respectively; the description ">100" indicates that an EC$_{50}$ value is a higher concentration than 100 nmol/L; and specific numerical values are omitted.

Test Example 2

A Cell Viability Evaluation Test in No Stress-Induced Cell Death Using Human Dermal Fibroblasts Derived from ALS Patient A compound is evaluated by measuring the degree of rescue of NO stress-induced cell death caused by the addition of SIN-1 and the like to an ALS patient-derived fibroblast (refer to T. Aguirre (1998) Annals of Neurology, 43(4): 452-457).

Test Example 3

ALS Animal Model Test

A compound is evaluated by administering the compound to an ALS model mouse that spontaneously develops an ALS-like symptom for a predetermined period and measuring motor functions and the like (refer to Takeo Ishiyama (2004) Brain Research, 1019: 226-236).

As described above, compounds of this disclosure are illustrated by preferable embodiments. However, it will be understood that the scope of the present disclosure should be interpreted only by the claims. It will be understood that the contents of patents, patent applications, and literatures cited in the present specification should be incorporated by reference in their entirety to the present specification as if their contents were specifically described in the present specification.

INDUSTRIAL APPLICABILITY

As described above, the compounds of the present invention are useful as a therapeutic and/or prophylactic drug for cancer, amyotrophic lateral sclerosis, Creutzfeldt-Jakob disease, Machado-Joseph disease, spinocerebellar ataxia, Huntington disease, Parkinson disease, Friedreich ataxia (FRDA), Alzheimer disease, atherosclerosis, myocardial infarction, cerebral infarction, aging-related disease, diabetes, alcoholic liver injury, chronic obstructive pulmonary disease, Leber's hereditary optic neuropathy (LHON), mitochondrial myopathy, encephalopathy, lactic acidosis, and stroke-like episodes (MELAS), Leigh Syndrome, Kearns-Sayre syndrome (KSS), and the like.

What is claimed is:

1. A method of treating a disease caused by or aggravated by oxidative stress or mitochondrial dysfunction, comprising administering to a patient in need of the treatment and/or prevention a therapeutically effective amount of a compound according to formula (1):

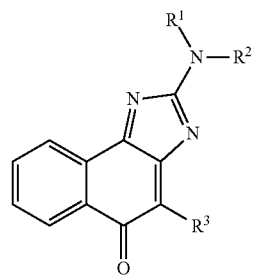

or a reduced form thereof, or a pharmaceutically acceptable salt thereof, wherein
R$^1$ and R$^2$ are each independently
(1) a hydrogen atom,
(2) an optionally substituted C$_{1-6}$alkyl group, an optionally substituted C$_{2-6}$alkenyl group, or an optionally substituted C$_{2-6}$alkynyl group,
(3) an optionally substituted C$_{3-10}$alicyclic hydrocarbon group (wherein the group may contain one or more unsaturated bonds),
(4) an optionally substituted, 3 to 8-membered heterocyclic group (wherein the group may contain one or more unsaturated bonds, and a carbon atom on the ring of the group is bonded with the nitrogen atom to which R$^1$ and R$^2$ are attached),
(5) an optionally substituted C$_{6-10}$aryl group, or
(6) an optionally substituted, 5 to 12-membered monocyclic or polycyclic heteroaryl group (with the proviso that in the group, a carbon atom on its ring is bonded with the nitrogen atom to which R$^1$ and R$^2$ are attached), or
R$^1$ and R$^2$ are taken together with the nitrogen atom to which they are attached to form an optionally substituted, 3 to 8-membered, nitrogen-containing heterocycle (wherein the heterocycle may contain one or more unsaturated bonds), and R³ is
(1) an optionally substituted $C_{6-10}$aryl group, or
(2) an optionally substituted, 5 to 12-membered monocyclic or polycyclic heteroaryl group (with the proviso that in the group, a carbon atom on its ring is bonded with the carbon atom to which R³ is attached); or
administering a pharmaceutical composition comprising the therapeutically effective amount of the compound of formula (1) and a pharmaceutically acceptable carrier, to a patient in need of the treatment;
wherein the disease caused by or aggravated by oxidative stress or mitochondrial dysfunction is selected from the group consisting of: amyotrophic lateral sclerosis (ALS), Huntington disease, Parkinson disease, Friedreich ataxia (FRDA), Alzheimer disease, multiple system atrophy (MS), Creutzfeldt-Jakob disease, Machado-Joseph disease, spinocerebellar ataxia, atherosclerosis, myocardial infarction, cerebral infarction, diabetes, alcoholic liver injury, non-alcoholic steatohepatitis (NASH), pulmonary fibrosis, hearing loss, spinal muscular atrophy (SMA), chronic obstructive pulmonary disease, Leber's hereditary optic neuropathy (LHON), mitochondrial myopathy, encephalopathy, lactic acidosis, and stroke-like episodes (MELAS), Leigh Syndrome and Kearns-Sayre syndrome (KSS), chronic progressive external ophthalmoplegia (CPEO), myoclonic epilepsy with ragged-red fibers (Fukuhara disease, MERRF, myoclonic epilepsy, myoclonic epilepsy syndrome), Pearson's disease (pancytopenia, multiple organ dysfunction syndrome), senile cognition disorder, cancer, and aging-related disease.

2. The method according to claim 1, wherein the compound or a reduced form thereof, or a pharmaceutically acceptable salt thereof, is wherein
R¹ and R² are each independently
(1) a hydrogen atom,
(2) an optionally substituted $C_{1-6}$alkyl group, an optionally substituted $C_{2-6}$alkenyl group, or an optionally substituted $C_{2-6}$alkynyl group (wherein each group is optionally substituted with one to three substituents independently selected from the group consisting of a halogen atom, a $C_{1-6}$alkoxy group, a $C_{3-6}$cycloalkyl group, and a hydroxyl group),
(3) a $C_{3-10}$alicyclic hydrocarbon group (wherein the group may contain one or more unsaturated bonds and the group is optionally substituted with one to three substituents independently selected from the group consisting of a $C_{1-6}$alkyl group, a halogen atom, a $C_{1-6}$alkoxy group, a $C_{3-6}$cycloalkyl group, and a hydroxyl group),
(4) a 3 to 8-membered heterocyclic group (wherein the group may contain one or more unsaturated bonds and the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups),
with the proviso that in the 3 to 8-membered heterocyclic group, when saturated, a carbon atom on its ring is bonded with the nitrogen atom to which R¹ and R² are attached),
(5) a $C_{6-10}$aryl group (wherein the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups)), or
(6) a 5 to 12-membered monocyclic or polycyclic heteroaryl group (wherein the group is optionally substituted with one to four groups independently selected from the group consisting of
(a) a halogen atom,
(b) a $C_{1-6}$alkyl group (wherein the group is optionally substituted with one to three halogen atoms),
(c) a $C_{1-6}$alkoxy group (wherein the group is optionally substituted with one to three halogen atoms), and
(d) an amino group (wherein the group is optionally substituted with one or two $C_{1-6}$alkyl groups),
with the proviso that in the 5 to 12-membered monocyclic or polycyclic heteroaryl group, a carbon atom on its ring is bonded with the nitrogen atom to which R¹ and R² are attached), or R¹ and R² are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a halogen atom, a $C_{1-6}$alkyl group, a $C_{1-6}$alkoxy group, and a hydroxyl group);
R³ is
(1) a $C_{6-10}$aryl group (wherein the group is optionally substituted with one to seven substituents independently selected from the group consisting of
(a) a halogen atom,
(b) a hydroxyl group,
(c) a cyano group,
(d) a $C_{1-6}$alkylsulfonyl group (wherein the $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(f) a $C_{1-6}$alkylcarbonyl group (wherein the $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group), (j) —N($R^4$)$COR^5$,
(k) —$CONR^6R^7$,
(l) —$S(O)_2NR^8R^9$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or two or more substituents on the $C_{6-10}$aryl group are joined to form a 5 to 8-membered non-aromatic carbocyclic or heterocyclic ring (wherein the 9 to 16-membered ring, which is formed when the $C_{6-10}$aryl group is joined with the 5 to 8-membered non-aromatic carbocyclic or heterocyclic ring, is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of
(a) a halogen atom,
(b) a hydroxyl group,
(c) a cyano group,
(d) a $C_{1-6}$alkylsulfonyl group (wherein the $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(e) a $C_{1-6}$alkylaminosulfonyl group (wherein each $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(f) a $C_{1-6}$alkylcarbonyl group (wherein the $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(g) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(h) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(i) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(j) a $C_{6-10}$aryl group (wherein the group is optionally substituted with one to three substituents independently selected from the group consisting of a halogen atom, a $C_{1-6}$alkoxy group, a $C_{3-6}$cycloalkyl group, and a hydroxyl group),
(k) —N($R^{10}$) $COR^{11}$,
(l) —$CONR^{12}R^{13}$,
(m) an amino group (wherein the group is optionally substituted with one or two $C_{1-6}$alkyl groups), and
(n) a 4 to 7-membered cyclic amino group (wherein the group is optionally substituted with one or two $C_{1-6}$alkyl groups), or two or more substituents on the 5 to 12-membered monocyclic or polycyclic heteroaryl group are joined to form a 5 to 8-membered non-aromatic carbocyclic or heterocyclic ring (wherein the 8 to 18-membered ring, which is formed when the 5 to 12-membered monocyclic or polycyclic heteroaryl group is joined with the 5 to 8-membered non-aromatic carbocyclic or heterocyclic ring, is optionally substituted with one or two $C_{1-6}$alkyl groups), with the proviso that in the 5 to 12-membered monocyclic or polycyclic heteroaryl group, a carbon atom on its ring is bonded with the carbon atom to which $R^3$ is attached); and $R^4$, $R^5$, $R^6$, $R^7$, $R^8$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$ and $R^{12}$ and $R^{13}$ each independently may be taken together to form a 4 to 10-membered, nitrogen-containing heterocycle.

3. The method according to claim 2, wherein the compound or a reduced form thereof, or a pharmaceutically acceptable salt thereof, is wherein $R^3$ is
(1) a $C_{6-10}$aryl group (wherein the group is optionally substituted with one to seven substituents independently selected from the group consisting of
(a) a halogen atom,
(b) a cyano group,
(c) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{1-6}$alkoxy group (wherein the $C_{1-6}$alkyl group is optionally substituted with one to three substituents independently selected from the group consisting of a halogen atom, a $C_{1-6}$alkoxy group, a $C_{3-6}$cycloalkyl group, and a hydroxyl group),
(e) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(f) —N($R^4$) $COR^5$,
(g) —$CONR^6R^7$,
(h) —$S(O)_2NR^8R^9$,
(i) an amino group (wherein the group is optionally substituted with one or two $C_{1-6}$alkyl groups), and
(j) a 4 to 7-membered cyclic amino group (wherein the group is optionally substituted with one or two $C_{1-6}$alkyl groups), or two substituents on the $C_{6-10}$aryl group are joined to form a 5 to 8-membered non-aromatic carbocyclic or heterocyclic ring (wherein the 9 to 16-membered ring, which is formed when the $C_{6-10}$aryl group is joined with the 5 to 8-membered non-aromatic carbocyclic or heterocyclic ring, is optionally substituted with one or two $C_{1-6}$alkyl groups)), or (2) a 5 to 12-membered monocyclic or polycyclic heteroaryl group (wherein the group is optionally substituted with one to nine substituents independently selected from the group consisting of
(a) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group),
(b) a $C_{1-6}$alkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(c) a $C_{3-10}$cycloalkoxy group (wherein the group is optionally substituted with one to three substituents independently selected from the group consisting of a halogen atom, a $C_{1-6}$alkoxy group, a $C_{3-6}$cycloalkyl group, and a hydroxyl group),
(d) a $C_{6-10}$aryl group (wherein the group is optionally substituted with one to three substituents independently selected from the group consisting of a halogen atom, a $C_{1-6}$alkoxy group, a $C_{3-6}$cycloalkyl group, and a hydroxyl group),
(e) —N($R^{10}$) $COR^{11}$,
(f) —$CONR^{12}R^{13}$,
(g) an amino group (wherein the group is optionally substituted with one or two $C_{1-6}$alkyl groups), and
(h) a 4 to 7-membered cyclic amino group (wherein the group is optionally substituted with one or two $C_{1-6}$alkyl groups), or
two substituents on the 5 to 12-membered monocyclic or polycyclic heteroaryl group are joined to form a 5 to 8-membered non-aromatic carbocyclic or heterocyclic ring (wherein the 8 to 18-membered ring, which is formed when the 5 to 12-membered monocyclic or polycyclic heteroaryl group is joined with the 5 to 8-membered non-aromatic carbocylic or heterocyclic ring, is optionally substituted with one or two $C_{1-6}$alkyl groups),
with the proviso that in the 5 to 12-membered monocyclic or polycyclic heteroaryl group, a carbon atom on its ring is bonded with the carbon atom to which $R^3$ is attached); and
$R^4$, $R^5$, $R^6$, $R^7$, $R^2$, $R^9$, $R^{10}$, $R^{11}$, $R^{12}$, and $R^{13}$ are each independently a hydrogen atom or a $C_{1-10}$alkyl group optionally substituted with one to five fluorine atoms, or $R^6$ and $R^7$, $R^8$ and $R^9$, and $R^{12}$ and $R^{13}$ each independently may be taken together to form a 4 to 10-membered, nitrogen-containing heterocycle.

4. The method according to claim 2, wherein the compound or a reduced form thereof, or a pharmaceutically acceptable salt thereof, is wherein $R^3$ is
(1) a $C_{6-10}$aryl group (wherein the group is optionally substituted with one to seven substituents independently selected from the group consisting of
(a) a halogen atom,
(b) a cyano group,
(c) a $C_{1-6}$alkyl group (wherein the group is optionally substituted with one to three substituents independently selected from the group consisting of a halogen atom and a $C_{1-6}$alkoxy group),
(d) a $C_{1-6}$alkoxy group (wherein the $C_{1-6}$alkyl group is optionally substituted with one to three halogen atoms),
(e) —N($R^4$) $COR^5$,
(f) —$CONR^6R^7$,
(g) —$S(O)_2NR^8R^2$,
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or two substituents on the $C_{6-10}$aryl group are joined to form a 5 to 8-membered non-aromatic heterocycle (wherein the 5 to 8-membered non-aromatic heterocycle is optionally substituted with one or two $C_{1-6}$alkyl groups)), or
(2) a 5 to 12-membered monocyclic or polycyclic heteroaryl group (wherein the group is optionally substituted with one to nine substituents independently selected from the group consisting of
(a) a $C_{1-6}$alkyl group,
(b) a $C_{1-6}$alkoxy group,
(c) a $C_{3-10}$cycloalkoxy group,
(d) a $C_{3-10}$aryl group,
(e) —N($R^{10}$)$COR^{11}$,
(f) —$CONR^{12}R^{13}$,
(g) an amino group (wherein the group is optionally substituted with one or two $C_{1-6}$alkyl groups), and
(h) a 4 to 7-membered cyclic amino group (wherein the group is optionally substituted with one or two $C_{1-6}$alkyl groups), or
two substituents on the 5 to 12-membered monocyclic or polycyclic heteroaryl group are joined to form a 5 to 8-membered non-aromatic heterocycle (wherein the 5 to 8-membered non-aromatic heterocycle is optionally substituted with one or two $C_{1-6}$alkyl groups),
with the proviso that in the 5 to 12-membered monocyclic or polycyclic heteroaryl group, a carbon atom on its ring is bonded with the carbon atom to which $R^3$ is attached); and
$R^4$, $R^5$, $R^6$, $R^7$, $R^2$, $R^9$, $R^{10}$, $R^{11}$, $R^{12}$, and $R^{13}$ are each independently a hydrogen atom or a $C_{1-10}$alkyl group, or $R^6$ and $R^7$, $R^8$ and $R^9$, and $R^{12}$ and $R^{13}$ each independently may be taken together to form a 4 to 10-membered, nitrogen-containing heterocycle.

5. The method according to claim 2, wherein the compound or a reduced form thereof, or a pharmaceutically acceptable salt thereof, is wherein $R^1$ and $R^2$ are each independently
(1) a hydrogen atom,
(2) a $C_{1-6}$alkyl group (wherein the group is optionally substituted with one to three substituents independently selected from the group consisting of a halogen atom, a $C_{1-6}$alkoxy group, a $C_{3-6}$cycloalkyl group, and a hydroxyl group), or
(3) a $C_{3-10}$alicyclic hydrocarbon group (wherein the group may contain one or more unsaturated bonds and the group is optionally substituted with one to three substituents independently selected from the group consisting of a halogen atom, a $C_{1-6}$alkyl group, a $C_{1-6}$alkoxy group, a $C_{3-6}$cycloalkyl group, and a hydroxyl group), or
$R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a halogen atom, a $C_{1-6}$alkyl group, a $C_{1-6}$alkoxy group, and a hydroxyl group).

6. The method according to claim 2, wherein the compound or a reduced form thereof, or a pharmaceutically acceptable salt thereof, is wherein $R^1$ and $R^2$ are each independently a hydrogen atom, or a $C_{1-6}$alkyl group (wherein the group is optionally substituted with one to three $C_{1-6}$alkoxy groups), or
$R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one or two groups independently selected from the group consisting of a $C_{1-6}$alkyl group, a $C_{1-6}$alkoxy group, and a hydroxyl group).

7. The method according to claim 1, wherein the compound or a reduced form thereof, or a pharmaceutically acceptable salt thereof, is wherein
$R^1$ and $R^2$ are each independently an optionally substituted $C_{1-6}$alkyl group, or
$R^1$ and $R^2$ are taken together with the nitrogen atom to which they are attached to form an optionally substituted, 3 to 8-membered, nitrogen-containing heterocycle (the heterocycle may contain one or more unsaturated bonds.

8. The method according to claim 2, wherein the compound or a reduced form thereof, or a pharmaceutically acceptable salt thereof, is wherein
$R^1$ and $R^2$ are each independently
a $C_{1-6}$alkyl group (wherein the group is optionally substituted with one $C_{1-6}$alkoxy group), or
$R^1$ and $R^2$ are taken together with the nitrogen atom to which they are attached to form a 3 to 8-membered, nitrogen-containing heterocycle (wherein the heterocycle may contain one or more unsaturated bonds and the heterocycle is optionally substituted with one $C_{1-6}$alkyl group);
$R^3$ is
(1) a $C_{6-10}$aryl group (wherein the group is optionally substituted with one to seven substituents independently selected from the group consisting of
(a) halogen atom,
(b) cyano group,
(c) a $C_{1-6}$alkyl group (wherein the group is optionally substituted with one to three substituents independently selected from the group consisting of a halogen atom and a $C_{1-6}$alkoxy group),
(d) a $C_{1-6}$alkoxy group (wherein the $C_{1-6}$alkyl group is optionally substituted with one to three halogen atoms),
(e) —N($R^4$)CO$R^5$,
(f) —CON$R^6R^7$,
(g) —S(O)$_2$N$R^8R^9$,
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or
two substituents on the $C_{6-10}$aryl group are joined to form a 5 to 8-membered non-aromatic carbocyclic or heterocyclic ring (wherein the 9 to 16-membered ring, which is formed when the $C_{6-10}$aryl group is joined with the 5 to 8-membered non-aromatic carbocylic or heterocyclic ring, is optionally substituted with one or two $C_{1-6}$alkyl groups; or
(2) a 5 to 12-membered monocyclic or polycyclic heteroaryl group (wherein the group is optionally substituted with one to nine substituents independently selected from the group consisting of
(a) a $C_{1-6}$alkyl group,
(b) a $C_{1-6}$alkoxy group,
(c) a $C_{6-10}$aryl group, and
(d) a 4 to 7-membered cyclic amino group (wherein the group is optionally substituted with one or two $C_{1-6}$alkyl groups),
with the proviso that in the 5 to 12-membered monocyclic or polycyclic heteroaryl group, a carbon atom on its ring is bonded with the carbon atom to which $R^3$ is attached); and
$R^4$, $R^5$, $R^6$, and $R^7$ are each independently a hydrogen atom or a $C_{1-10}$alkyl group, and R 2 and $R^9$ are taken together to form a 4 to 10-membered, nitrogen-containing heterocycle (wherein the heterocycle may contain one or more unsaturated bonds).

9. The method according to claim 2, wherein the compound or a reduced form thereof, or a pharmaceutically acceptable salt thereof, is wherein $R^1$ and $R^2$ are each independently a $C_{1-6}$alkyl group (wherein the group is optionally substituted with one $C_{1-6}$alkoxy group).

10. The method according to claim 2, wherein the compound or a reduced form thereof, or a pharmaceutically acceptable salt thereof, is wherein $R^1$ and $R^2$ taken together with the nitrogen atom to which they are attached to form a 3 to 8-membered, nitrogen-containing heterocycle (wherein the heterocycle may contain one or more unsaturated bonds and the heterocycle is optionally substituted with one $C_{1-6}$alkyl group).

11. The method according to claim 2, wherein the compound or a reduced form thereof, or a pharmaceutically acceptable salt thereof, wherein
$R^3$ is a $C_{6-10}$aryl group (wherein the group is optionally substituted with one to seven substituents independently selected from the group consisting of
(a) halogen atom,
(b) cyano group,
(c) a $C_{1-6}$alkyl group (wherein the group is optionally substituted with one to three substituents independently selected from the group consisting of a halogen atom and a $C_{1-6}$alkoxy group),
(d) a $C_{1-6}$alkoxy group (wherein the $C_{1-6}$alkyl group is optionally substituted with one to three halogen atoms),
(e) —N($R^4$)CO$R^5$,
(f) —CON$R^6R^7$,
(g) —S(O)$_2$N$R^8R^9$,
(h) an amino group (wherein the group is optionally substituted with one or two $C_{1-6}$alkyl groups), and
(i) a 4 to 7-membered cyclic amino group (wherein the group is optionally substituted with one or two $C_{1-6}$alkyl groups), or
two substituents on the $C_{6-10}$aryl group are joined to form a 5 to 8-membered non-aromatic carbocyclic or heterocyclic ring (wherein the 9 to 16-membered ring, which is formed when the $C_{6-10}$aryl group is joined with the 5 to 8-membered non-aromatic carbocyclic or heterocyclic ring, is optionally substituted with one or two $C_{1-6}$alkyl groups; and
$R^4$, $R^5$, $R^6$, and $R^7$ are each independently a hydrogen atom or a $C_{1-10}$alkyl group, and $R^8$ and $R^9$ are taken together to form a 4 to 10-membered, nitrogen-containing heterocycle (wherein the heterocycle may contain one or more unsaturated bonds).

12. The method according to claim 2, wherein the compound or a reduced form thereof, or a pharmaceutically acceptable salt thereof, is wherein $R^3$ is a 5 to 12-membered monocyclic or polycyclic heteroaryl group (wherein the group is optionally substituted with one to nine substituents independently selected from the group consisting of
(a) a $C_{1-6}$alkyl group,
(b) a $C_{1-6}$alkoxy group,
(c) a $C_{6-10}$aryl group, and
(d) a 4 to 7-membered cyclic amino group (wherein the group is optionally substituted with one or two $C_{1-6}$alkyl groups),
with the proviso that in the 5 to 12-membered monocyclic or polycyclic heteroaryl group, a carbon atom on its ring is bonded with the carbon atom to which $R^3$ is attached).

13. The method according to claim 2, wherein the compound or a reduced form thereof, or a pharmaceutically acceptable salt thereof, is wherein the compound is selected from the group consisting of the following compounds:
Example 1
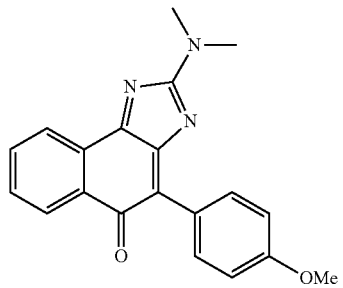
Example 2
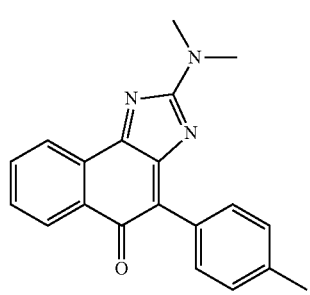
Example 3
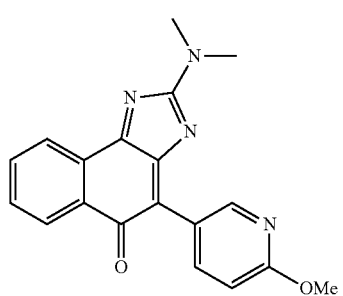
Example 4
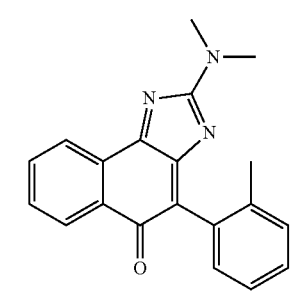
Example 5
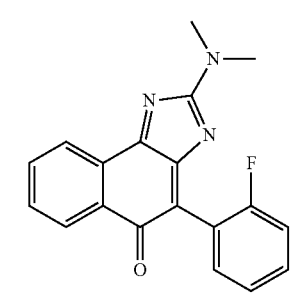
-continued
Example 6
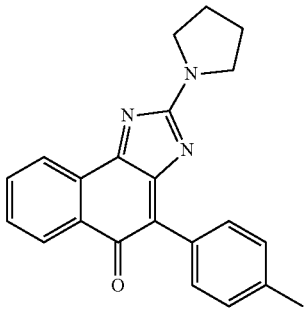
Example 7
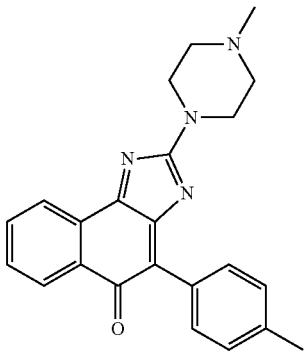
Example 8
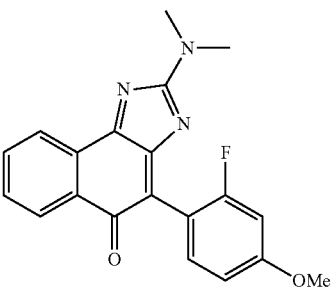
Example 9
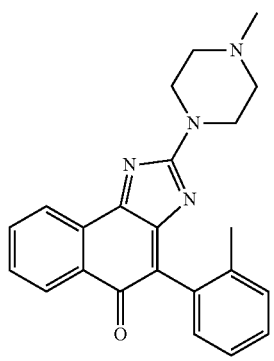
Example 10
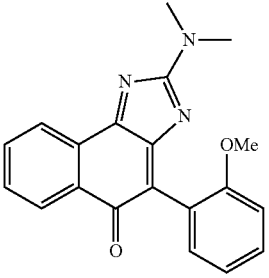

Example 11
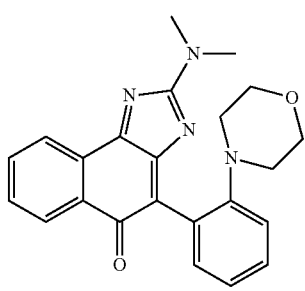
Example 12
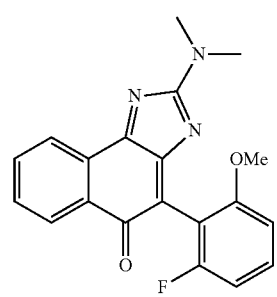
Example 13
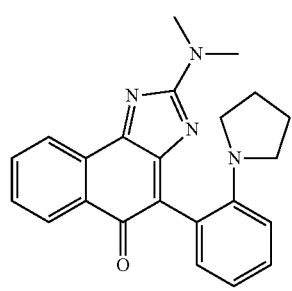
Example 14
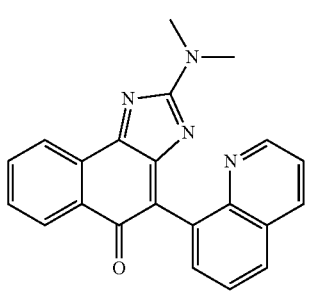
Example 15
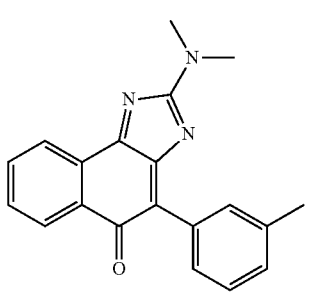
Example 16
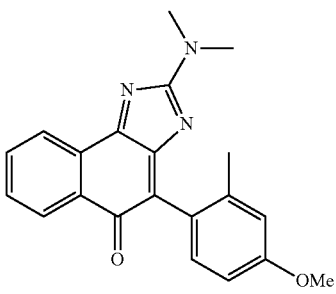
Example 17
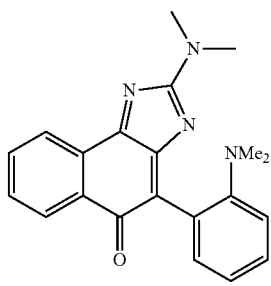
Example 18
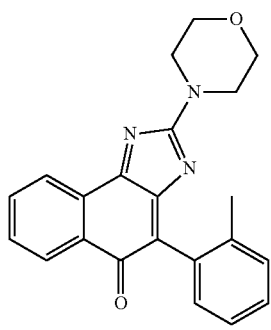
Example 19
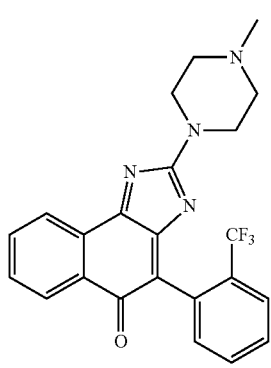
Example 20
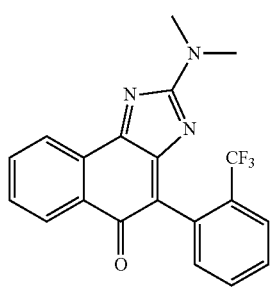

-continued
Example 21
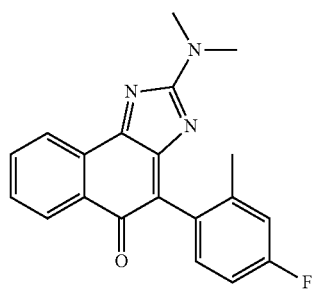
Example 22
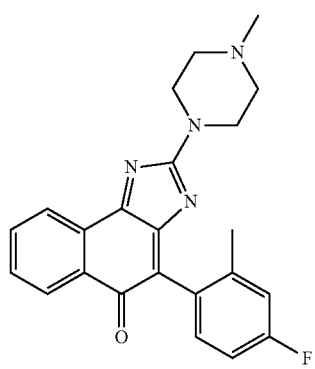
Example 23
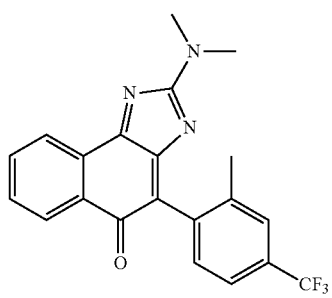
Example 24
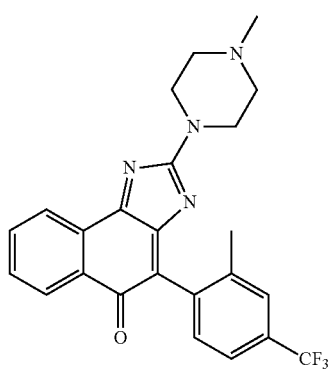
Example 25
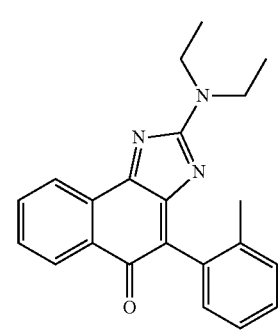
-continued
Example 26
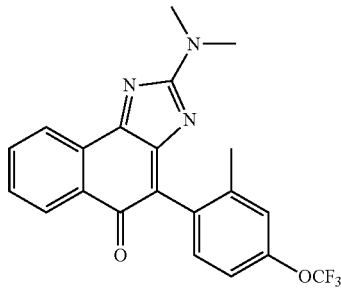
Example 27
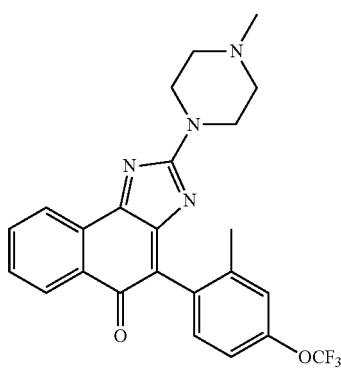
Example 28
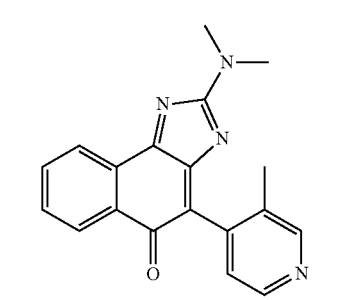
Example 29
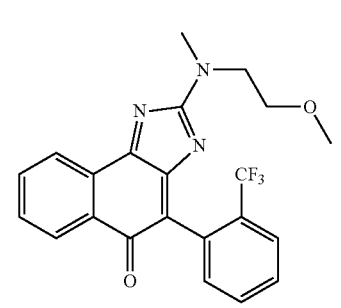
Example 30
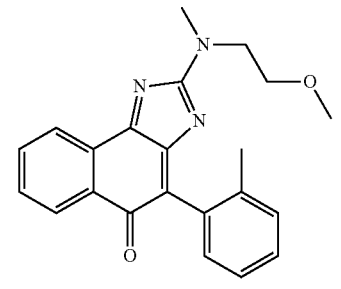

Example 31
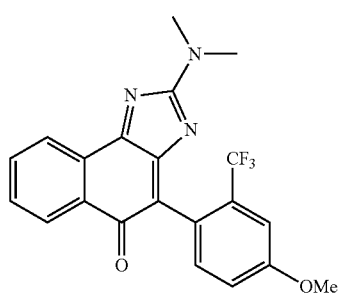
Example 32
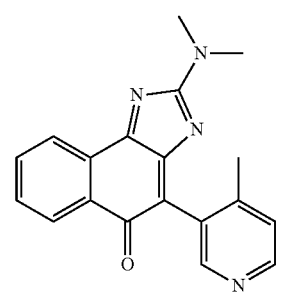
Example 33
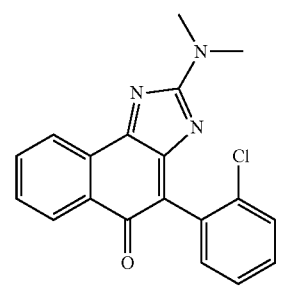
Example 34
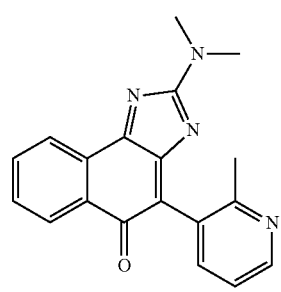
Example 35
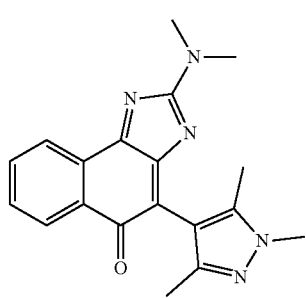
Example 36
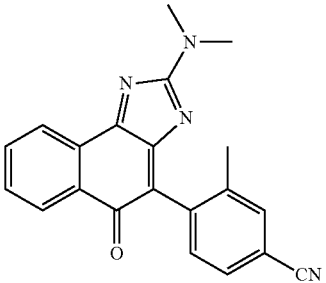
Example 37
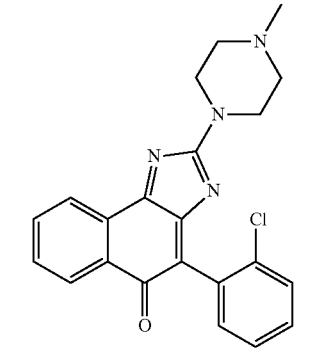
Example 38
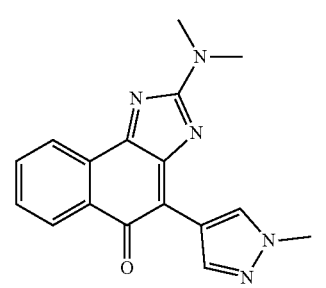
Example 39
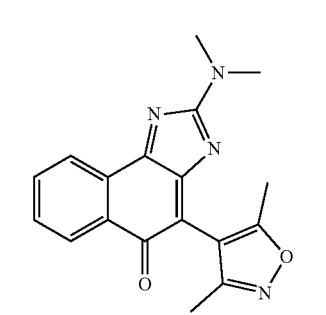
Example 40
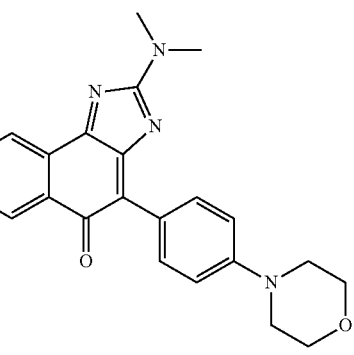

-continued
Example 41
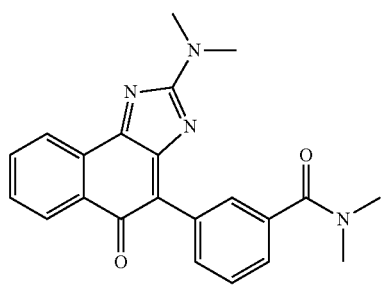
Example 42
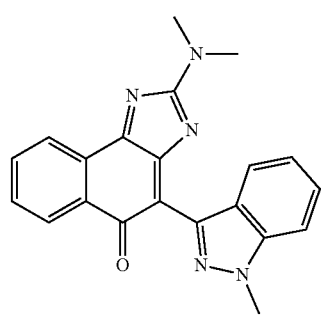
Example 43
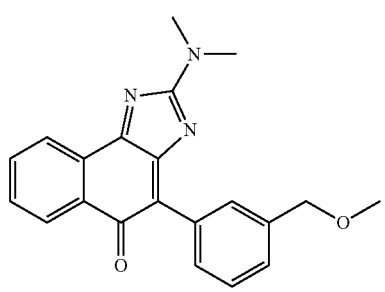
Example 44
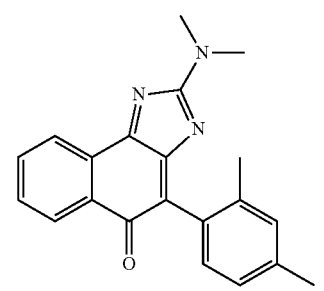
Example 45
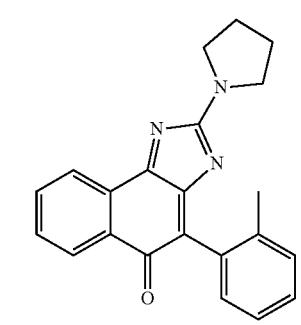
Example 46
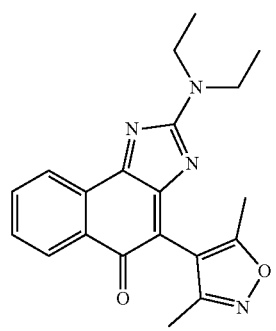
Example 47
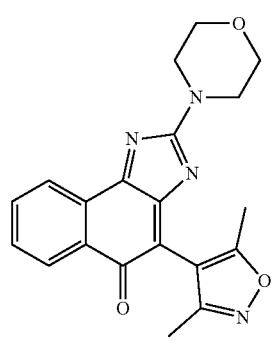
Example 48
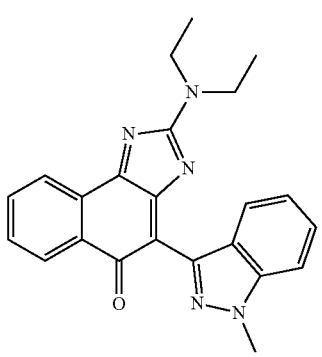
Example 49
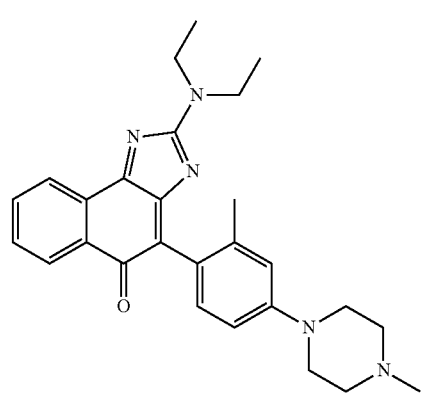

-continued
Example 50
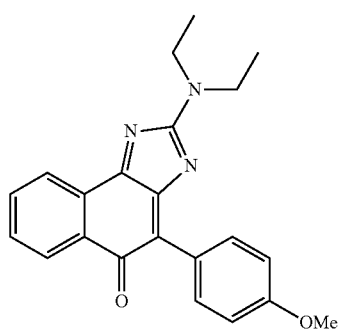
Example 51
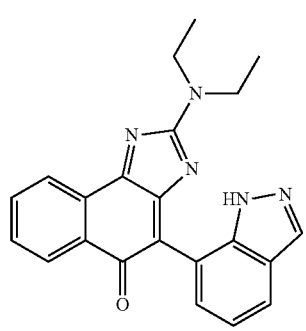
Example 52
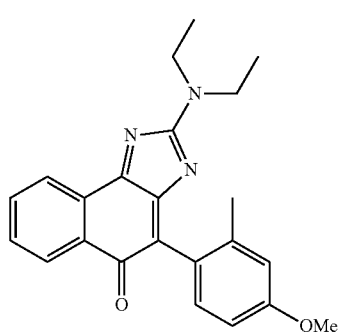
Example 53
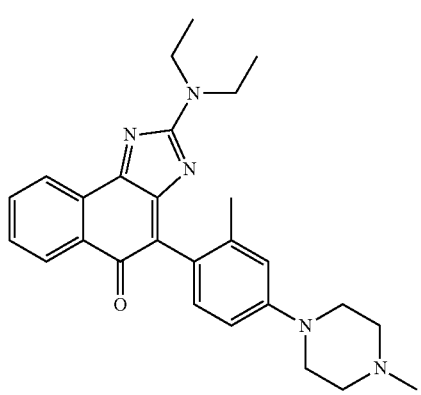
-continued
Example 54
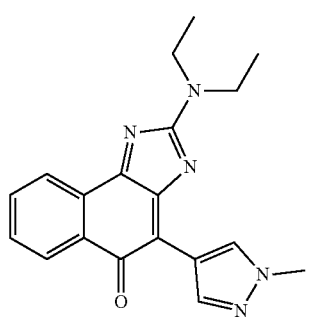
Example 55
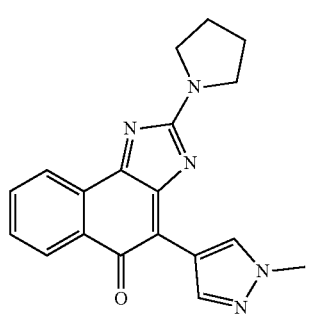
Example 56
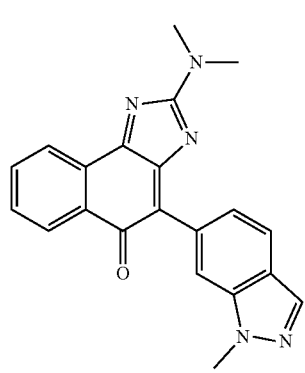
Example 57
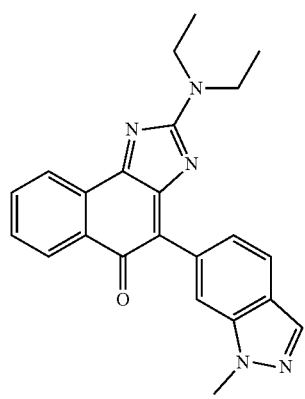

Example 58
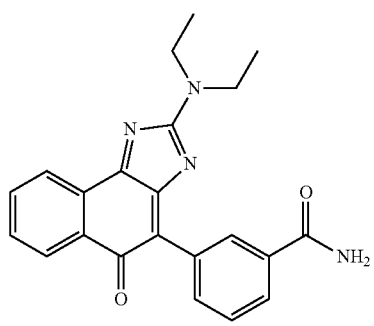
Example 59
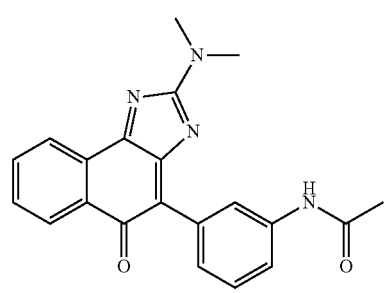
Example 60
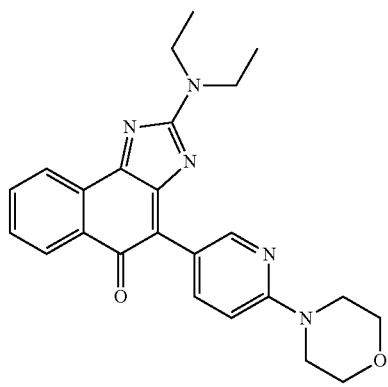
Example 61
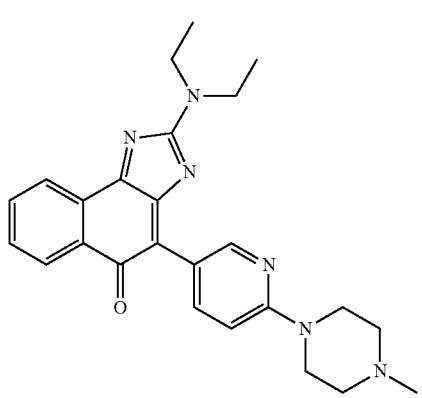
Example 62
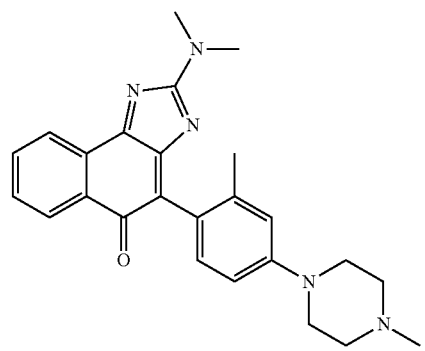
Example 63
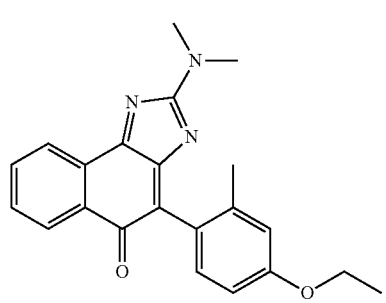
Example 64
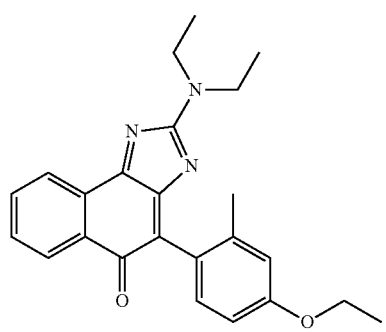
Example 65
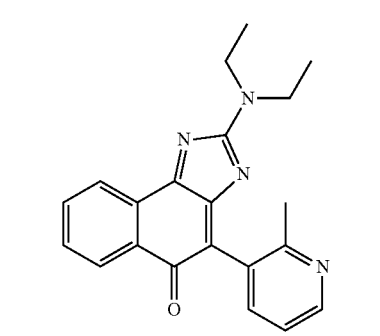
Example 66
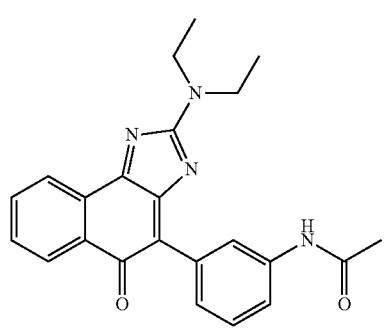

Example 67
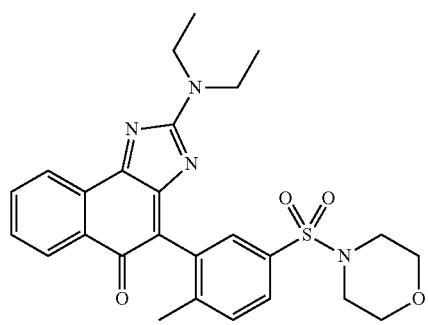
Example 68
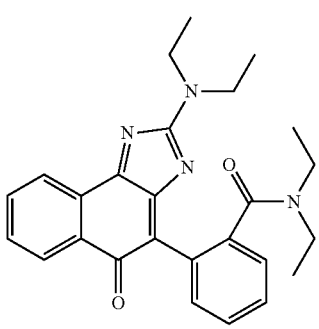
Example 69
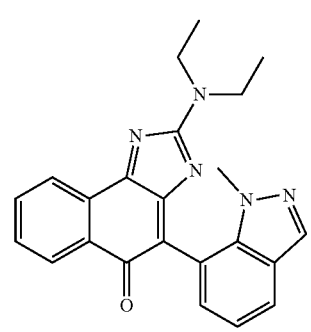
Example 70
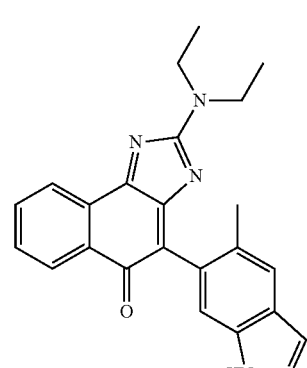
Example 71
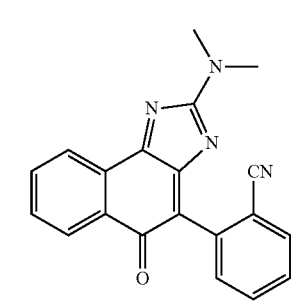
Example 72
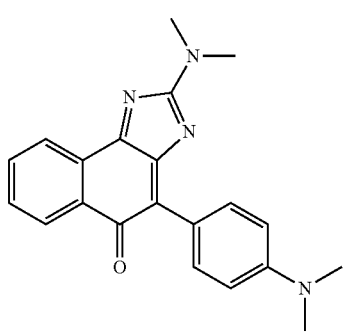
Example 73
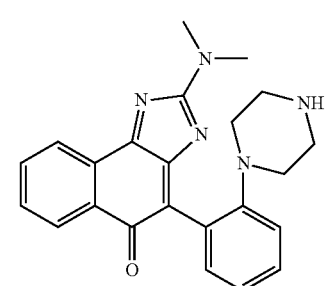
Example 74
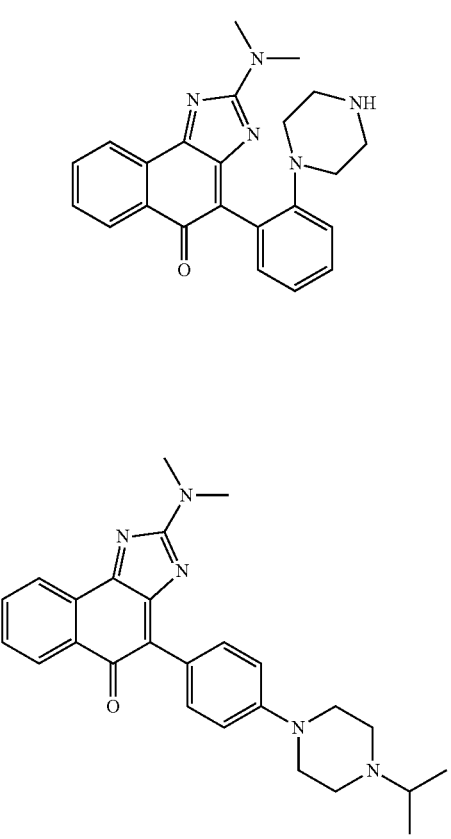
Example 75
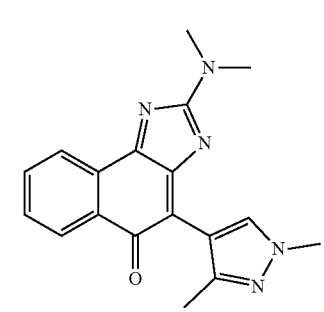

Example 76
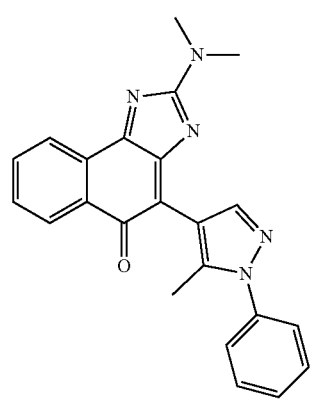
Example 77
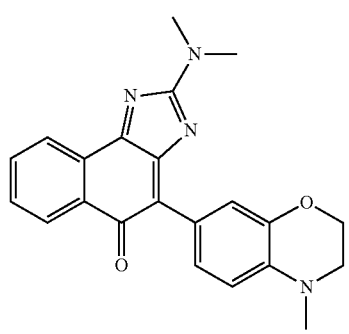
Example 78
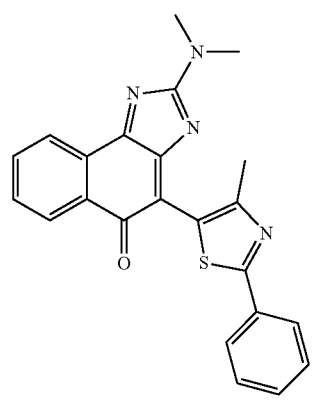
Example 79
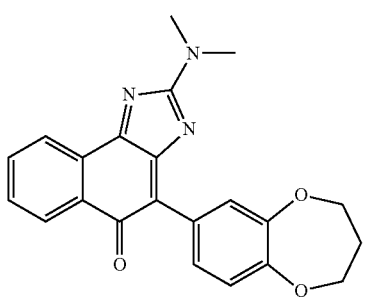
Example 80
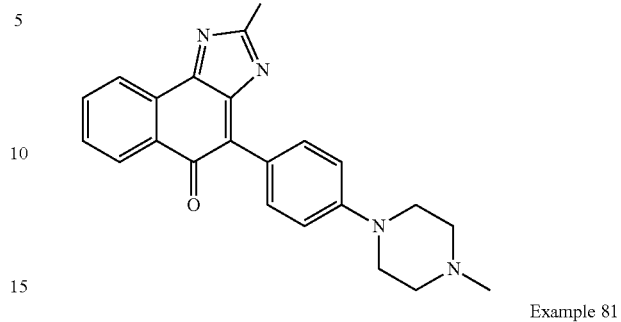
Example 81
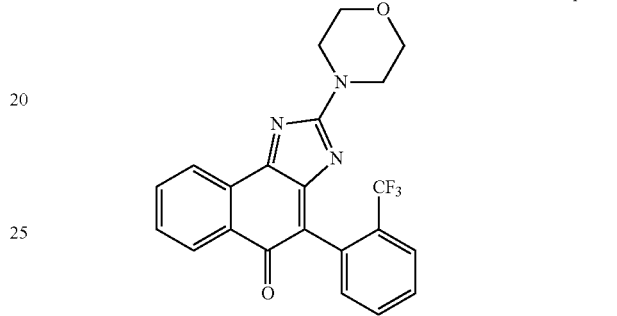
Example 82
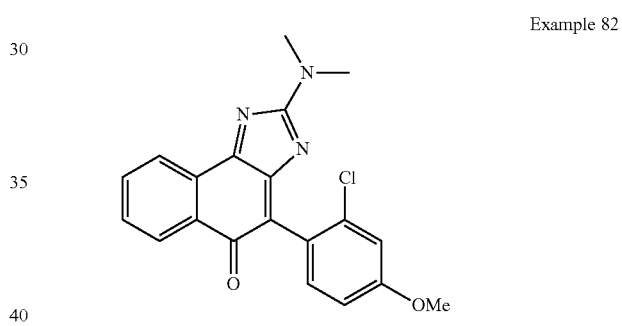
Example 83
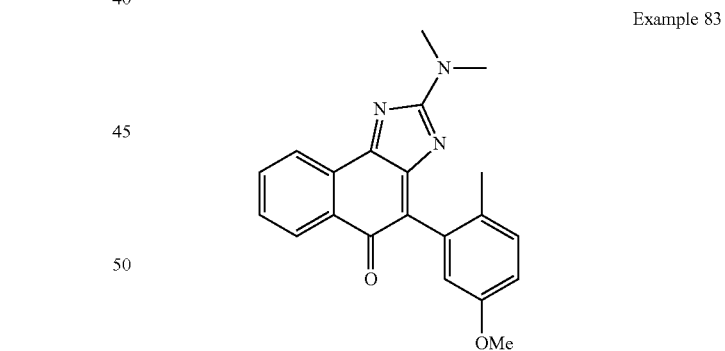
Example 84
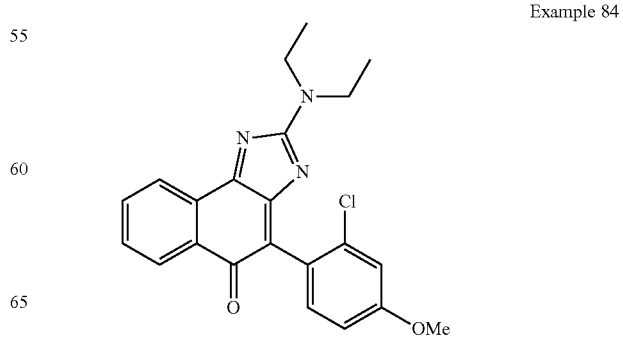

-continued

Example 85
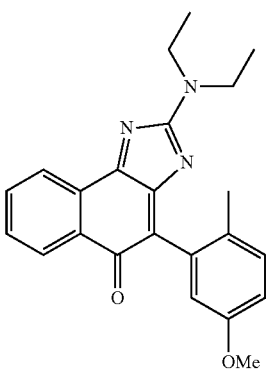

Example 86
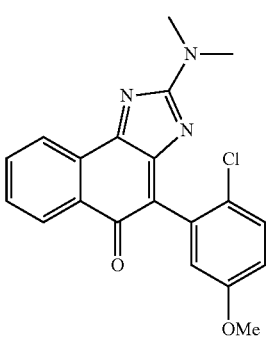

Example 87
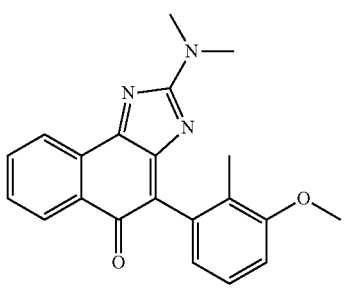

Example 88
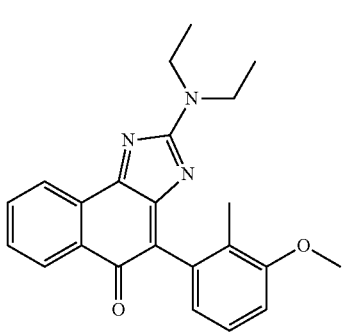

Example 89
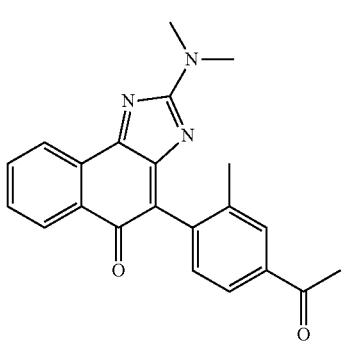

-continued

Example 90
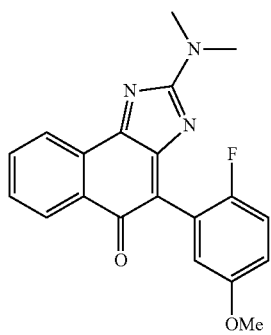

Example 91
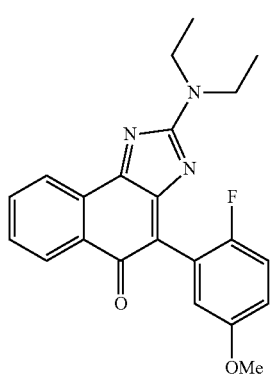

Example 92
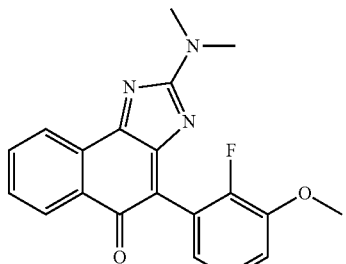

and

Example 93
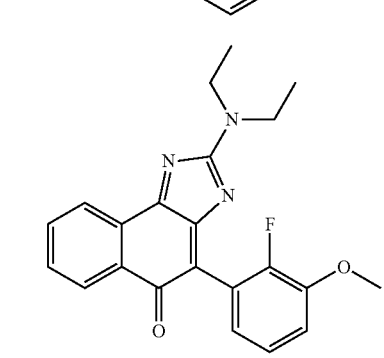

14. The method according to claim 2, wherein the compound or a reduced form thereof, or a pharmaceutically acceptable salt thereof, is wherein the compound is selected from the group consisting of the following compounds:
2-(dimethylamino)-4-(4-methylphenyl)-5H-naphth[1,2-d]imidazol-5-one;
2-(dimethylamino)-4-(2-methylphenyl)-5H-naphth[1,2-d]imidazol-5-one;
4-(2-methylphenyl)-2-(4-methylpiperazin-1-yl)-5H-naphth[1,2-d]imidazol-5-one;
2-(dimethylamino)-4-[2-(morpholin-4-yl)phenyl]-5H-naphth[1,2-d]imidazol-5-one;

2-(dimethylamino)-4-[2-(trifluoromethyl)phenyl]-5H-naphth[1,2-d]imidazol-5-one;
2-(dimethylamino)-4-[2-methyl-4-(trifluoromethyl)phenyl]-5H-naphth[1,2-d]imidazol-5-one;
2-(diethylamino)-4-(2-methylphenyl)-5H-naphth[1,2-d]imidazol-5-one;
2-(dimethylamino)-4-[2-methyl-4-(trifluoromethoxy)phenyl]-5H-naphth[1,2-d]imidazol-5-one;
4-(2-chlorophenyl)-2-(dimethylamino)-5H-naphth[1,2-d]imidazol-5-one;
2-(dimethylamino)-4-(1,3,5-trimethyl-1H-pyrazol-4-yl)-5H-naphth[1,2-d]imidazol-5-one;
2-[(2-dimethylamino)-5-oxo-5H-naphth[1,2-d]imidazol-4-yl]benzonitrile;
4-[(2-dimethylamino)-5-oxo-5H-naphth[1,2-d]imidazol-4-yl]-3-methylbenzonitrile; and
2-(dimethylamino)-4-(2-chloro-4-methoxyphenyl)-5H-naphth[1,2-d]imidazol-5-one.

15. The method of claim 2, wherein the compound is selected from the group consisting of:

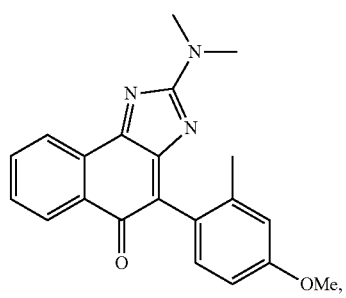

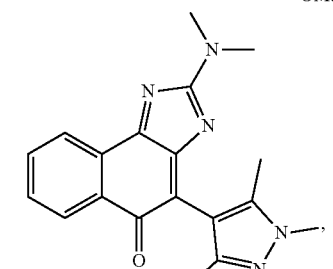

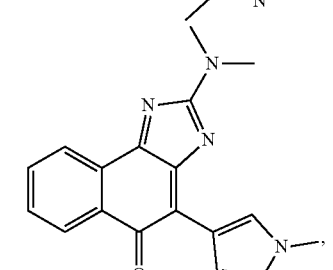

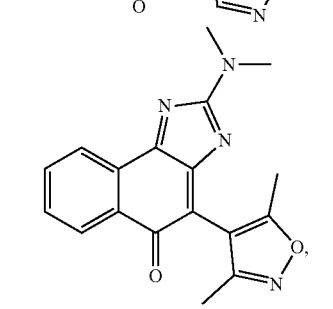

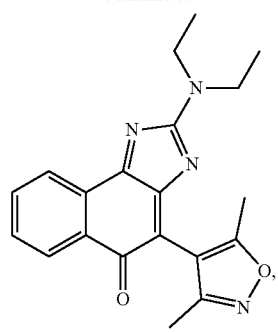

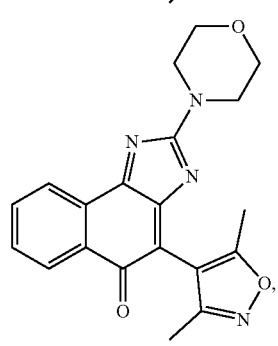

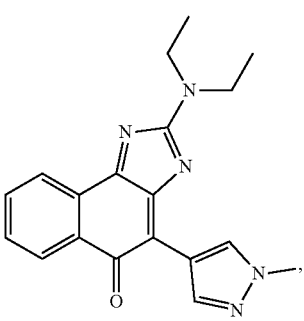

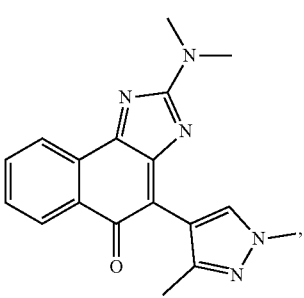

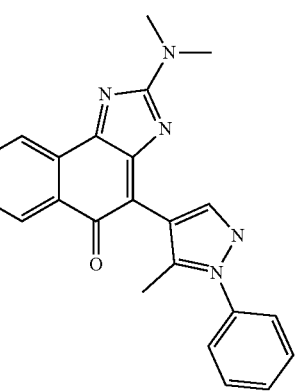

-continued
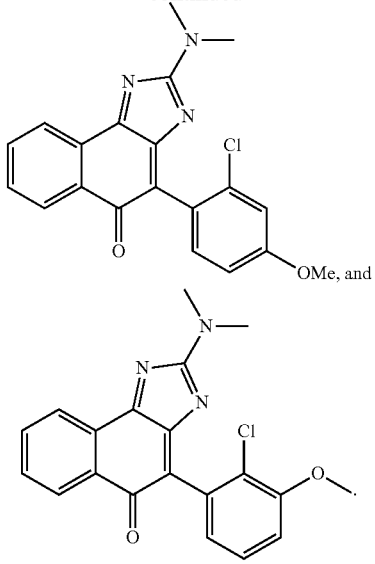
16. The method of claim 2, wherein the compound is
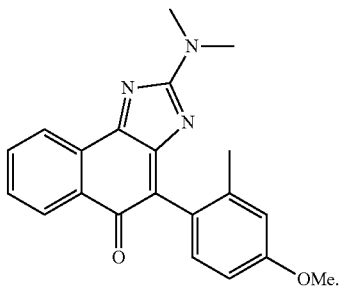 [SMILES: COc1ccc(C2=C3N=C(N(C)C)N=C3c3ccccc3C2=O)c(C)c1]
17. The method of claim 2, wherein the compound is
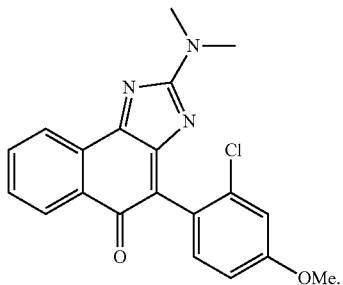 [SMILES: COc1ccc(C2=C3N=C(N(C)C)N=C3c3ccccc3C2=O)c(Cl)c1]
18. The method of claim 2, wherein the compound is
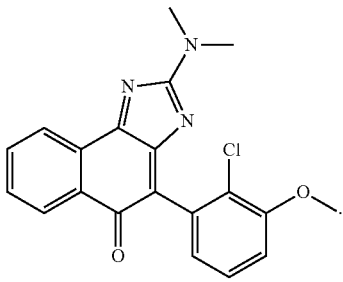
* * * * *